(12) United States Patent
Pendon et al.

(10) Patent No.: US 11,103,492 B2
(45) Date of Patent: *Aug. 31, 2021

(54) COMPOSITIONS AND KITS FOR OMEPRAZOLE SUSPENSION

(71) Applicant: Azurity Pharmaceuticals, Inc., Woburn, MA (US)

(72) Inventors: Zeus Pendon, Woburn, MA (US); Steven Dinh, Burlington, MA (US)

(73) Assignee: Azurity Pharmaceuticals, Inc., Woburn, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/017,295

(22) Filed: Sep. 10, 2020

(65) Prior Publication Data

US 2021/0069167 A1 Mar. 11, 2021

Related U.S. Application Data

(63) Continuation of application No. 16/998,731, filed on Aug. 20, 2020, which is a continuation of application No. 16/513,604, filed on Jul. 16, 2019, now Pat. No. 10,751,333.

(51) Int. Cl.
| | |
|---|---|
| *A61K 31/4439* | (2006.01) |
| *A61K 47/38* | (2006.01) |
| *A61K 47/24* | (2006.01) |
| *A61K 47/10* | (2017.01) |
| *A61K 47/34* | (2017.01) |
| *A61K 9/00* | (2006.01) |
| *A61K 47/26* | (2006.01) |
| *A61K 47/12* | (2006.01) |
| *A61K 31/351* | (2006.01) |

(52) U.S. Cl.
CPC ........ *A61K 31/4439* (2013.01); *A61K 9/0053* (2013.01); *A61K 31/351* (2013.01); *A61K 47/10* (2013.01); *A61K 47/12* (2013.01); *A61K 47/24* (2013.01); *A61K 47/26* (2013.01); *A61K 47/34* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 5,658,919 | A | 8/1997 | Ratnaraj et al. |
| 5,763,449 | A | 6/1998 | Anaebonam et al. |
| 6,645,988 | B2 | 11/2003 | Phillips |
| 7,300,670 | B2 | 11/2007 | Venus et al. |
| 7,815,933 | B2 | 10/2010 | Holmberg |
| 2004/0191276 | A1 | 9/2004 | Muni |
| 2004/0192763 | A1 | 9/2004 | Chenard et al. |
| 2005/0142271 | A1 | 6/2005 | Ojima et al. |
| 2006/0094787 | A1 | 5/2006 | Forenzo et al. |
| 2008/0299211 | A1 | 12/2008 | Chrzan et al. |
| 2010/0015184 | A1 | 1/2010 | Tuel |
| 2010/0323020 | A1 | 12/2010 | Gokhale et al. |
| 2013/0079311 | A1 | 3/2013 | Muni |
| 2014/0371242 | A1 | 12/2014 | Wang |
| 2015/0216806 | A1 | 8/2015 | Borody |
| 2015/0238613 | A1 | 8/2015 | Lin et al. |
| 2016/0361320 | A1 | 12/2016 | Zhao et al. |
| 2017/0065671 | A1 | 3/2017 | Maher |
| 2019/0321348 | A1* | 10/2019 | Fallin ................ A61K 47/02 |

FOREIGN PATENT DOCUMENTS

| | | |
|---|---|---|
| WO | WO-0103707 A1 | 1/2001 |
| WO | WO-2004080451 A1 | 9/2004 |
| WO | WO-2004080541 A1 | 9/2004 |
| WO | WO-2008048018 A1 | 4/2008 |
| WO | WO-2017218894 A1 * | 12/2017 ............ A61K 47/36 |

OTHER PUBLICATIONS

CutisPharma; FIRST®—Omeprazole: Safety Data Sheet; Oct. 17, 2017; https://firstkits.com/wp-content/uploads/2019/10/FIRST_Omeprazole_SDS_US_101717_FINAL.pdf; accessed Mar. 24, 2021 (Year: 2017).*

Kittipongpatana et al.; "Development of Suspending Agent from Sodium Carboxymethyl Mungbean Starches"; 2006; Drug Development and Industrial Pharmacyl 32:809-820; DOI: 10.1080/03639040500529978 (Year: 2006).*

International Search Report and Written Opinion dated Oct. 19, 2020, for PCT/US2020/042157.

Anonymous, Process for preparing posaconazole oral suspension, IP.com Journal (2013), 13(5B), 1 (No. IPCOM000227453D), May 8, 2013, 2 pages, second page.

Bogman et al., P-glycoprotein and surfactants: effect on intestinal talinolol absorption. Clin Pharmacol Ther. Jan. 2005;77(1):24-32.

Castell, D., Review of immediate-release omeprazole for the treatment of gastric acid-related disorders. Expert Opin Pharmacother. Nov. 2005,6(14).2501-10.

Chuong, M.C., et al., To Flavor or Not to Flavor Extemporaneous Omeprazole Liquid, International Journal of Pharmaceutical Compounding,Oct. 31, 2017, 21(6):500-512.

Cutispharma, Inc., Omeprazole, Omeprazole 2mg/mL in FIRST®-PPI Suspension Compounding Kit, Ingredients, published Dec. 7, 2015 as per Wayback Machine, [retrieved from the internet on Jul. 13, 2017], URL:https://web.archive.org/web/20151207113010/http://www.cutispharma.com:80/products/oral-solutions-suspensions/ppis/omeprazole, Ingredients section.

Extended European Search Report dated Feb. 1, 2020, for EP Application No. 17814171.9.

Extended European Search Report dated Feb. 2, 2020 for EP Application No. 17814171.9.

First Omeprazole Info, http:/www.cutispharma.com/omepinfo.html, Nov. 2012.

(Continued)

*Primary Examiner* — Timothy P Thomas
(74) *Attorney, Agent, or Firm* — Wilson Sonsini Goodrich & Rosati

(57) ABSTRACT

Disclosed herein are liquid diluents, formulations, and kits for preparing reconstituted suspensions of a proton pump inhibitor (e.g., omeprazole). The present disclosure also provides formulations for liquid diluents that do not have a tendency for gel formation following exposure to freeze-thaw cycles.

19 Claims, 13 Drawing Sheets

(56) References Cited

OTHER PUBLICATIONS

Fischer et al., Effect of the non-ionic surfactant Poloxamer 188 on passive permeability of poorly soluble drugs across Caco-2 cell monolayers. Eur J Pharm Biopharm. Oct. 2011;79(2):416-22. doi: 10.1016/j.ejpb.2011.04.010. Epub Apr. 28, 2011.
International Preliminary Report on Patentability for PCT/US2017/037875 dated Dec. 27, 2018.
International Search Report and Written Opinion dated Jul. 19, 2017, for PCT/US17/037875.
Johnson, C.E., et al., Stability of partial doses of omeprazole-sodium bicarbonate oral suspension. Ann Pharmacother. Dec. 2007;41(12):1954-61. Epub Oct. 23, 2007.
Kent F. Burnett, C. Barr Taylor, and W. Stewart Agras; Ambulatory Computer-Assisted Therapy of Obesity: A New Frontier for Behavior Therapy; Journal of Consulting and Clinical Psychology, 1985, vol. 50, No. 5, 698-703; 1985 by the American Psychological Associates, Inc.
Matthew, Mary et al., Stability of Omeprazole Solutions at Various pH Values as Determiend by High Performance Liquid Chromatography, Drug Development and Industrial Pharmacy, (Year 1995).
Moschwitzer,Development of intravenously injectable chemically stable aqueous omeprazole formulation using nano suspension technology, European Journal of Pharmaceutics and Biopharmaceutics, 58, 2004.

[No Author Listed], Metolose® Metolose® SR. ShinEtsu. 20 pages.
[No Author Listed], Carboxymethylcellulose (CMC). CMC Book. 1st edition. 28 pages.
[No Author Listed], CMC for Pharmaceutical Applications. Application Bulletin AB-94. 12 pages.
[No Author Listed], Signet Selection Guide to Excipients. 5th edition. 177 pages.
Non-Final Office Action dated Apr. 3, 2020 for U.S. Appl. No. 16/310,675.
Notice of Allowance dated Jun. 24, 2020 for U.S. Appl. No. 16/513,604.
Sharma, V.K., et al., Oralpharmacokinetics of omeprazole and lansoprazole after single and repeated doses as intact capsules or as suspensions in sodium bicarbonate. Aliment Pharmacol Ther. Jul. 2000; 14(7): 887-92.
Sharma,V.K., Comparison of 24-hour intragastric pH using four liquid formulations of lansoprazole and omeprazole. Am J Health Syst Pharm. Dec. 1, 1999;56(23 Suppl 4):S18-21.
XP-013157146, Process for preparing Posaconazole oral suspension, IP.com, Inc., West Henrietta, NY, US, May 8, 2013, ISSN: 1533-001.
Xu et al., Controllable gelation of methylcellulose by a salt mixture. Langmuir. Jul. 20, 2004; 20(15):6134-8.
U.S. Appl. No. 16/998,731, filed Aug. 20, 2020.

* cited by examiner

COMPOSITIONS AND KITS FOR OMEPRAZOLE SUSPENSION

CROSS REFERENCE

This application is a continuation of U.S. application Ser. No. 16/998,731 filed Aug. 20, 2020, which (i) is a continuation application of U.S. application Ser. No. 16/513,604, filed Jul. 16, 2019, now U.S. Pat. No. 10,751,333 issued Aug. 25, 2020, and (ii) claims priority to International Application No. PCT/US2020/042157, filed Jul. 15, 2020. Each of which is entirely incorporated herein by reference in its entirety.

BACKGROUND OF THE INVENTION

Medications are often prescribed in a solid dosage form which many patients are unable to swallow, requiring these medications to be administered in an oral liquid form. The populations unable to swallow solid dosage forms and are in need of liquid formulations include pediatric patients, older patients with dysphagia, ICU patients and patients on enteral nutrition. Acid-related disorders are one of the most common conditions affecting these populations and as such are associated with significant healthcare resource utilization. Common disorders of acid-related conditions include: gastric ulcers, gastroesophageal reflux disease (GERD), *Helicobactor pylori* infection, non-ulcer related dyspepsia, gastritis, and Zollinger-Ellison syndrome. The prevalence of chronic acid-related disorders in the US is on the rise, with GERD and peptic ulcer disease (PUD) responsible for the majority of occurrences. GERD is reported as afflicting more than 60 million Americans, showing 20% of the population having symptoms at least twice a week.

In order to successfully manage acid-related disorders, gastric acid production must be suppressed with the use of a Proton Pump inhibitor (PPI). PPIs are a critical group of medications that treat and prevent a range of diseases and pathologies that relate to the production of excess stomach acid and consequent damage to the GI tract (e.g., gastroesophageoal reflux disease, gastroesophageoal disorders). Several PPIs are approved for use, but are generally limited to solid dosage forms.

SUMMARY OF THE INVENTION

The present disclosure is based, inter alia, on liquid formulations for preparing an Omeprazole Powder for Oral Suspension Kit (e.g., 2 mg/ml). The oral suspension kits of the present disclosure contain bottled active pharmaceutical ingredient (API; e.g., PPI; e.g., omeprazole) and pre-measured diluent, which can be reconstituted to form an oral omeprazole suspension. These kits containing the omeprazole are stable (e.g., under refrigerated conditions, e.g., 2-8° C.). The diluents are freeze-thaw stable. The API and the diluent of the present disclosure have long term stability (e.g., up to 24 months). Once reconstituted, the suspension stability can be, for example, up to and greater than 30 days. The liquid formulations (e.g., reconstituted suspensions) are homogenous and stable for at least 30 days at refrigerated temperatures. Additionally, the diluents are freeze-thaw stable.

Accordingly, one aspect of the present disclosure provides a liquid diluent for the reconstitution of omeprazole, consisting essentially of:
  about 0.5%-4% w/v poloxamer (e.g., poloxamer 188) (preferably about 1.0%-4.0% w/v poloxamer);
  about 1.0%-2.5% w/v sodium carboxymethylcellulose (sodium CMC) (preferably about 1.0%-2.0% w/v sodium CMC);
  about 8.0%-8.8% w/v sodium bicarbonate;
  about 0.5%-1.5% w/v sodium citrate;
  about 0.1%-0.3% w/v simethicone emulsion;
  about 2.0%-3.0% w/v sorbitol solution (70%);
  about 0.35%-0.5% w/v sucralose;
  about 0.4%-0.6% w/v benzyl alcohol; and
  water;
wherein the liquid diluent is stable for at least 30 days.

In some embodiments, the poloxamer (e.g., poloxamer 188) is about 1% w/v. In some embodiments, the poloxamer (e.g., poloxamer 188) is about 2% w/v. In some embodiments, the poloxamer (e.g., poloxamer 188) is about 4% w/v. In some embodiments, the sodium CMC is about 1.2% w/v. In some embodiments, the liquid diluent includes a coloring agent, wherein the coloring agent is about 0.002%-0.005% w/v FD&C Red No. 40. In some embodiments, the FD&C Red No. 40 is about 0.003% w/v. In some embodiments, the liquid diluent includes a flavoring agent, wherein the flavoring agent is about 0.1%-0.2% w/v Strawberry Flavor CW08. In some embodiments, the Strawberry Flavor CW08 is about 0.15% w/v. In some embodiments, the sodium bicarbonate is about 8.4% w/v. In some embodiments, the sodium citrate is about 1% w/v. In some embodiments, the simethicone emulsion is about 0.15% w/v. In some embodiments, the 70% sorbitol solution is about 2.5% w/v and the sucralose is about 0.4% w/v. In some embodiments, the benzyl alcohol is about 0.5% w/v.

Another aspect of the present disclosure provides a suspension of omeprazole consisting essentially of omeprazole, poloxamer (e.g., poloxamer 188), sodium CMC, sodium bicarbonate, sodium citrate, simethicone emulsion, benzyl alcohol, a sweetener, and water, wherein the suspension is homogenous and stable for at least 30 days at ambient conditions and at refrigerated temperature conditions. In some embodiments, the poloxamer (e.g., poloxamer 188) is about 0.5%-4.0% w/v (preferably about 1.0%-4.0% w/v). In some embodiments, the poloxamer (e.g., poloxamer 188) is about 1% w/v. In some embodiments, the sodium CMC is about 1.0%-2.5% w/v (preferably about 1.0%-2.0% w/v). In some embodiments, the sodium CMC is about 1.2% w/v. In some embodiments, the poloxamer (e.g., poloxamer 188) is about 0.5%-4.0% w/v (preferably about 1.0%-4.0%) and the sodium CMC is about 1.0%-2.5% w/v (preferably about 1.0%-2.0% w/v). In some embodiments, the suspension consists essentially of:
  omeprazole;
  about 0.5%-4% w/v poloxamer (e.g., poloxamer 188) (preferably about 1.0%-4.0% w/v poloxamer);
  about 1.0%-2.5% w/v sodium CMC (preferably about 1.0%-2.0% w/v sodium CMC);
  about 8.0%-8.8% w/v sodium bicarbonate;
  about 0.5%-1.5% w/v sodium citrate;
  about 0.1%-0.3% w/v simethicone emulsion;
  about 0.35%-3.5% w/v sweetener;
  about 0.4%-0.6% w/v benzyl alcohol; and
  water.

Another aspect of the present disclosure provides a freeze-thaw stable diluent for the reconstitution of omeprazole, consisting essentially of omeprazole, poloxamer (e.g., poloxamer 188), sodium CMC, sodium bicarbonate, sodium citrate, simethicone emulsion, benzyl alcohol, a sweetener, a flavoring agent, a coloring agent, and water, wherein the freeze-thaw stable diluent is free from gel formation following at least one freeze-thaw cycle. In some embodiments, the poloxamer (e.g., poloxamer 188) is about 0.5%-4.0% w/v (preferably about 1.0%-4.0% w/v poloxamer (e.g., poloxamer 188)) and the sodium CMC is about 1.0%-2.5% w/v (preferably about 1.0%-2.0% w/v sodium CMC).

Another aspect of the present disclosure provides a kit consisting essentially of a first container having a non-sterile 100% w/w omeprazole powder; a second container having a liquid diluent consisting essentially of poloxamer (e.g., poloxamer 188), sodium CMC, sodium bicarbonate, sodium citrate, simethicone emulsion, benzyl alcohol, a sweetener, and water; wherein the first and second containers are of a size such that the omeprazole powder and liquid diluent can be combined in either the first or second container to produce a reconstituted omeprazole suspension; wherein the reconstituted omeprazole suspension is homogenous and stable for at least 30 days at ambient and refrigerated temperature conditions. In some embodiments, the percent of omeprazole powder dissolved to make the reconstituted omeprazole suspension is >80% by dissolution assay after 5 minutes of mixing. In some embodiments, the poloxamer (e.g., poloxamer 188) is about 0.5%-4.0% w/v (preferably about 1.0%-4.0% w/v poloxamer (e.g., poloxamer 188)) and the sodium CMC is about 1.0%-2.5% w/v (preferably about 1.0%-2.0% w/v sodium CMC). In some embodiments, the poloxamer (e.g., poloxamer 188) is about 1% w/v, sodium CMC is about 1.2% w/v; sodium bicarbonate is about 8.4% w/v; sodium citrate is about 1.0% w/v; benzyl alcohol is about 0.5% w/v; and simethicone emulsion is about 0.15% w/v. In some embodiments, the sweetener is about 2.5% w/v sorbitol solution (70%) and about 0.4% w/v sucralose.

In one aspect, described herein is a freeze-thaw stable liquid diluent for reconstitution of a proton pump inhibitor, wherein the liquid diluent comprises: (a) about 1.0%-4.0% w/v surfactant, wherein the surfactant comprises a block copolymer of polyethylene glycol and polypropylene glycol; (b) about 1.0%-2.0% w/v sodium carboxymethylcellulose (CMC); (c) about 8.0%-8.8% w/v acid neutralizing agent, wherein the acid neutralizing agent is sodium bicarbonate; (d) about 0.5%-1.5% w/v citrate buffer; (e) about 0.1%-0.3% w/v simethicone emulsion, wherein the simethicone emulsion comprises about 30% w/w simethicone; (f) about 0.4%-0.6% w/v preservative, wherein the preservative is benzyl alcohol; and (h) water, wherein the liquid diluent is free of gel formation following at least one freeze-thaw cycle. In some embodiments, the surfactant is poloxamer (e.g., poloxamer 188).

In one aspect, described herein is a reconstituted liquid suspension of omeprazole for oral administration, comprising omeprazole powder and a liquid diluent, wherein the liquid diluent comprises: (a) about 1.0%-4.0% w/v surfactant, wherein the surfactant comprises a block copolymer of polyethylene glycol and polypropylene glycol; (b) about 1.0%-2.0% w/v sodium carboxymethylcellulose (CMC); (c) about 8.0%-8.8% w/v acid neutralizing agent, wherein the acid neutralizing agent is sodium bicarbonate; (d) about 0.5%-1.5% w/v citrate buffer; (e) about 0.1%-0.3% w/v simethicone emulsion, wherein the simethicone emulsion comprises about 30% w/w simethicone; (f) about 0.4%-0.6% w/v preservative, wherein the preservative is benzyl alcohol; and (h) water, wherein the liquid diluent is free of gel formation following at least one freeze-thaw cycle, wherein the reconstituted liquid suspension is stable for at least 30 days at 5±3° C. and at 25±5° C., and wherein the stability is measured by having from about 90% w/w to about 110% w/w of the initial omeprazole amount at the end of the given storage period.

In some embodiments, the surfactant is poloxamer (e.g., poloxamer 188). In some embodiments, the omeprazole powder is present in the liquid suspension at about 2 mg/ml. In one aspect, described herein is reconstituted liquid suspension of omeprazole for oral administration, comprising: (a) about 2 mg/ml omeprazole; (b) about 1.0%-4.0% w/v surfactant, wherein the surfactant comprises a block copolymer of polyethylene glycol and polypropylene glycol; (c) about 1.0%-2.0% w/v sodium carboxymethylcellulose (CMC); (d) about 8.0%-8.8% w/v acid neutralizing agent, wherein the acid neutralizing agent is sodium bicarbonate; (e) about 0.5%-1.5% w/v citrate buffer; (f) about 0.1%-0.3% w/v simethicone emulsion, wherein the simethicone emulsion comprises about 30% w/w simethicone; (g) about 0.4%-0.6% w/v preservative, wherein the preservative is benzyl alcohol; and (h) water, wherein the reconstituted liquid suspension is stable for at least 30 days at 5±3° C. and at 25±5° C., and wherein the stability is measured by having from about 90% w/w to about 110% w/w of the initial omeprazole amount at the end of the given storage period.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. For purposes of clarity, not every component may be labeled in every drawing. It is to be understood that the data illustrated in the drawings in no way limit the scope of the disclosure. In the drawings.

DETAILED DESCRIPTION OF THE INVENTION

Figure 1:
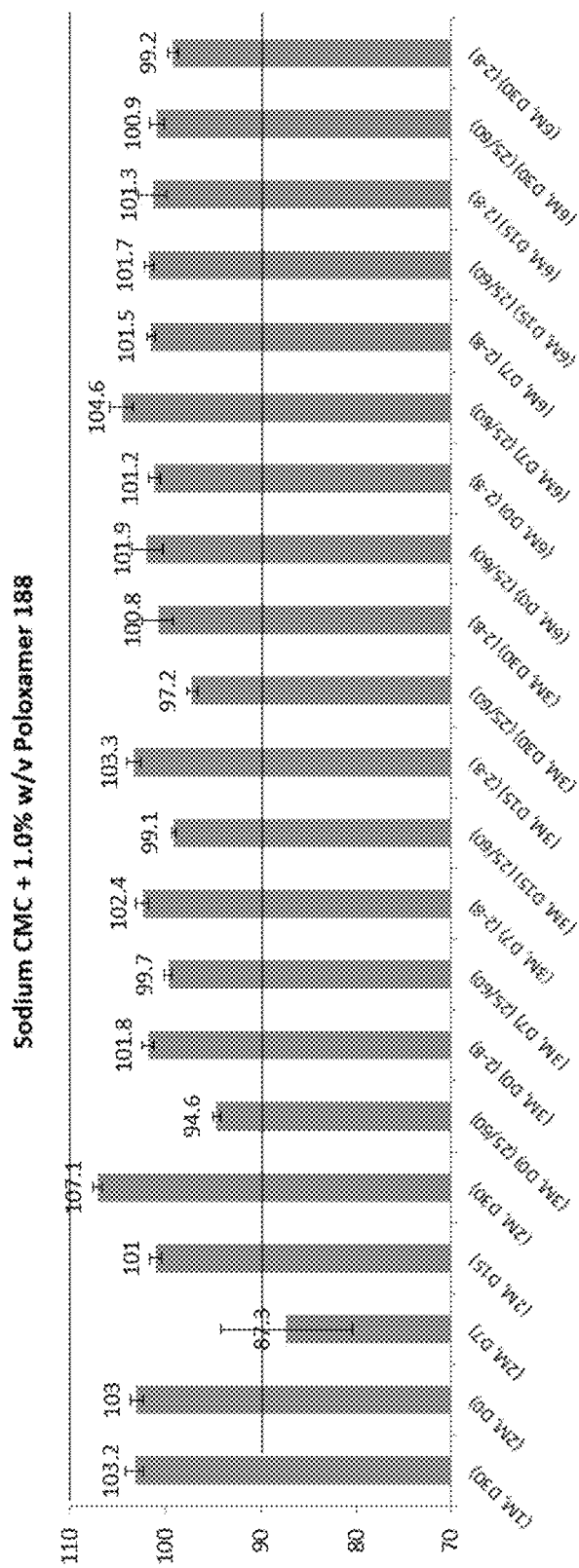
FIG. 1 includes a bar graph showing the assay comparison of the sodium CMC+1% w/v poloxamer reconstituted suspension at different stability time points.

During the preliminary stage of diluent development for an omeprazole powder for oral suspension, a diluent was manufactured using xanthan gum as a polymer/viscosity building agent and stability studies were initiated for an omeprazole powder for an oral suspension kit. During the course of stability studies, gel formation was observed in a xanthan gum formulation upon storage at 2-8° C., which is an undesirable characteristic for a diluent. To identify potential causes for the gelation of the diluent and understand the gel composition, the gel was further characterized. A new diluent (reformulated diluent) which is not associated with gelation but which maintains long term stability properties and can be used for the formulation of omeprazole powder has been developed. The inventive diluent was demonstrated to have useful properties. It does not exhibit the undesirable gelation characteristic of the prior art diluent and maintains stability. Additionally, quite surprisingly, the reformulated diluent when mixed with omeprazole still functions as a diluent with long-term stability, homogeneity, and freeze-thaw stability, as described below. Herein, suspendability studies revealed that sodium carboxymethylcellulose (sodium CMC; optionally 1.0-2.5% w/v) in the diluent formulations showed significantly better suspendability compared to diluents using a different type of suspending agent. Additionally, it was found that diluent formulations with specific co-solvents (e.g., glycerin, propylene glycol) and specific suspending agents (e.g., xanthan gum) have a tendency (or high risk) for gelation after undergoing freeze-thaw cycles. The sodium CMC is particularly effective when used with poloxamer. It was believed that poloxamer would interfere with omeprazole activity. However, surprisingly, it was demonstrated herein that when the poloxamer is combined with sodium CMC the omeprazole activity was preserved.

The present disclosure provides liquid diluents (also referred to as diluent formulations or formulations) for proton pump inhibitors (PPI; e.g., omeprazole) and suspensions of the liquid diluents with the proton pump inhibitors (PPI; e.g., omeprazole), as well as related compounding kits. The diluents have enhanced stability for 30 days, 3 months, 6 months or 24 months at ambient and/or refrigerated conditions with respect to other available diluents. The suspensions are homogenous and have enhanced stability for 30 days at ambient and/or refrigerated conditions with respect to other available suspensions.

The liquid diluents disclosed herein provide a vehicle for the delivery of a suspension of an active pharmaceutical ingredient (API) (herein, a PPI e.g., omeprazole) within a solution comprising a surfactant (e.g., poloxamer, e.g., poloxamer 188) and a suspending agent (e.g., sodium CMC). In some embodiments, an exemplary liquid diluent of the present invention comprises one or more of, or in other embodiments, all of:

a surfactant (e.g., poloxamer (e.g., poloxamer 188))
a viscosity building/suspending agent (e.g., sodium CMC (the product sodium carboxymethylcellulose sold under the trademark CEKOL® 700P))
an acid neutralizing agent (e.g., sodium bicarbonate)
a defoamer (e.g., simethicone emulsion)
a flavoring agent (e.g., strawberry flavor CW08)
a sweetener (e.g., sorbitol solution (e.g., 70%), sucralose)
a buffer system (e.g., sodium bicarbonate and sodium citrate)
a coloring agent (e.g., FD&C Red No. 40)
a preservative (e.g., benzyl alcohol)
water In some embodiments, the liquid diluent of the present disclosure comprises poloxamer (e.g., poloxamer 188), sodium CMC, an acid neutralizing agent, a buffer, a defoamer, a sweetener, and a preservative. In some embodiments of the present disclosure, the diluent comprises the following:

0.5%-4% w/v poloxamer (e.g., poloxamer 188) (preferably 1% w/v);
1.0%-2.5% w/v sodium CMC (preferably 1.2% w/v);
8.0%-8.8% w/v acid neutralizing agent (preferably 8.4% w/v);
0.5%-1.5% w/v buffer (preferably 1% w/v);
0.1%-0.3% w/v defoamer (preferably 0.15% w/v);
2.0%-3.5% w/v sweeteners (preferably 2.9% w/v);
0.4%-0.6% w/v preservative (preferably 0.5% w/v); and
water.

In some embodiments of the present disclosure, the liquid diluent consists essentially of:

0.5%-4% w/v poloxamer (e.g., poloxamer 188) (preferably 1% w/v);
1.0%-2.5% w/v sodium CMC (preferably 1.2% w/v);
8.0%-8.8% w/v acid neutralizing agent (preferably 8.4% w/v);
0.5%-1.5% w/v buffer (preferably 1% w/v);
0.1%-0.3% w/v defoamer (preferably 0.15% w/v);
2.0%-3.5% w/v sweeteners (preferably 2.9% w/v);
0.4%-0.6% w/v preservative (preferably 0.5% w/v); and
water.

In such embodiments, the liquid diluent may contain other ingredients that do not materially affect its long-term stability, homogeneity, and/or freeze-thaw stability, as described herein. Similarly, the long-term stability, homogeneity, and/or freeze-thaw stability of the reconstituted suspension made from said liquid diluent and active pharmaceutical ingredient (API; e.g., a PPI, e.g., omeprazole) is not materially affected.

In some embodiments, neither the suspension nor the diluent comprises xanthan gum. In some embodiments, neither the suspension nor the diluent comprises a co-solvent such as glycerin, propylene glycol or an equivalent thereof.

The reconstituted suspension of the present invention is prepared by mixing the powder active pharmaceutical ingredient (API; e.g., a PPI, e.g., omeprazole) with a liquid solution, also referred to as a diluent or solution component. The diluent imparts improved properties on the reconstituted suspension, such as homogeneity and long term stability (e.g., for 7, 14, 15, or 30 days). The diluent has stability, as defined herein, and is freeze-thaw stable, as defined herein. It was discovered quite surprisingly that the optimal liquid solution displaying these characteristics comprises sodium CMC and poloxamer (e.g., poloxamer 188).

Without being bound by theory, the viscosity of poloxamer (e.g., poloxamer 188) increases and can lead to gelation with increasing temperature. This has to do with the transition of free to micelle formation of poloxamer (e.g., poloxamer 188) as a function of temperature. Sodium CMC can also gel with increasing temperatures. Herein, it was found that a liquid diluent formulated with at least the combination of poloxamer (e.g., poloxamer 188) and sodium CMC is freeze-thaw stable.

Without being bound by theory, the suspending agent contributes to the homogeneity of the reconstituted suspensions. Without being bound by theory, sodium bicarbonate serves to protect the API and provides a buffered solution that promotes the maintenance of a constant pH during liquid storage after formulation, and that promotes the neutralization of stomach acid after dosing in order to minimize the acid digestion or degradation of the API in the patient's stomach. Sodium citrate provides a buffer for the diluent. Thickening agents and sweeteners are included to improve the handling, appearance, and palatability of the finished dosage.

The compositions of the present disclosure can be used in methods of treating acid related disorders comprising administering to a patient, such as a child or an elderly patient an oral liquid formulation reconstituted from proton pump inhibitor (PPI) powder and the diluents disclosed herein.

Solid Oral Doses

Commonly, pediatric and geriatric populations encounter difficulty being administered solid oral dosage forms such as capsules and tablets, which may lead to noncompliance with the solid oral dosage forms and likely results in rendering the therapy ineffective. Solid oral dosage forms are usually not favorable for pediatric and geriatric populations due to the potential risk of choking. Additionally, certain solid oral dosage forms of medications cannot be administered simply by crushing (e.g., patients requiring various types of feeding tubes) because of the coating or drug delivery mechanism by which the drug is released. For most community pharmacies (retail/chain and independent), extemporaneously reconstituted PPIs do not provide the ease of use, flavoring, flexible dosing, or a uniform formulation.

The current method of overcoming the aforementioned drawbacks of the solid oral dosage form of PPIs is emptying multiple capsules and dissolving the granules in sodium bicarbonate to achieve the prescribed concentration. This method of preparation is cumbersome and time-consuming for pharmacists in today's busy pharmacies. Other commonly reconstituted preparations include the product omeprazole with sodium bicarbonate sold under the trademark ZEGERID® powder for oral solution packets and unit does packets, which are reconstituted in water, but do not allow for flexible dosing.

Liquid Oral Doses

Suspensions of proton pump inhibitors (e.g., omeprazole) can be made by reconstituting the active pharmaceutical ingredient (API) with a diluent. In some embodiments, the suspension is made by reconstituting a proton pump inhibitor (PPI; e.g., omeprazole, esomeprazole, lansoprazole, rabeprazole, pantoprazole, and dexlansoprazole) with a diluent described herein. These diluents, which, ideally, would be stable for an extended period of time (e.g., 14 days, 30 days, 3 months, 6 months, 24 months, etc.) at ambient and/or refrigerated temperatures. Yet another challenge presented by these diluents is a tendency for gel formation when stored for long periods of time and/or when the diluent is taken through one or more freeze-thaw cycles.

The liquid formulations of the invention have, for example, 30 day stability at refrigerated storage conditions and ambient temperature. The liquid formulations of the invention have improved palatability compared to commercially available formulations, and when compared to previously described oral formulations or reconstituted formulations. The liquid formulations of the invention have improved homogeneity when compared to commercially available liquid formulations. The liquid formulations of the invention have optimized viscosity to reduce agglomeration and adherence of the product to the container. Importantly, the diluents of the present invention are freeze-thaw stable (i.e. have a significantly reduced risk of forming a gel after undergoing one or more freeze-thaw cycles).

The liquid nature of the formulations disclosed allows the dosing of PPIs to children who are unable to reliably swallow capsules. In addition, the liquid nature of the formulations disclosed allows the dosing of PPIs to elderly patients who are unable to reliably swallow capsules. Furthermore, the liquid nature of the formulations disclosed allows the dosing of PPIs to critical care patients who are otherwise unable to swallow capsules due to intubation or other injuries, pathologies, or interventions that inhibit the ability to receive or take medication in solid format. In addition, the ability of the invention enables the pharmacy to improve the delivery of the drug by nasogastric feeding tube or other device designed, intended, or used to deliver liquids to a patient's stomach or esophagus.

The ability to use the liquid formulations of the invention also offers advantages to physicians, as it provides the ability to prescribe with more flexibility for a range of challenging and otherwise vulnerable patients. In addition, by utilizing the formulations of the present invention, the physician is able to prescribe doses of other PPIs in a format that assures the safe and reliable delivery of drug to patients in a palatable, stable, and homogenous format that can be prepared in a pharmacy, thus minimizing errors of preparation by patients. The palatability of the disclosed formulations improves patient compliance and minimizes patient distress.

The described pharmaceutical composition (such as the suspensions) can be administered by any suitable schedules. In some embodiments, the pharmaceutical composition such as the suspension is administered once daily. In some embodiments, the pharmaceutical composition such as the suspension is administered twice daily. In some embodiments, the pharmaceutical composition such as the suspension is administered 1-4 times daily. In some embodiments, the pharmaceutical composition such as the suspension is administered for about 2 weeks. In some embodiments, the pharmaceutical composition such as the suspension is administered for up to 2 weeks. In some embodiments, the pharmaceutical composition such as the suspension is administered for about 4 weeks. In some embodiments, the pharmaceutical composition such as the suspension is administered for up to 4 weeks. In some embodiments, the pharmaceutical composition such as the suspension is administered for about 4-8 weeks. In some embodiments, the pharmaceutical composition such as the suspension is administered for up to about 12 months. In some embodiments, the pharmaceutical composition such as the suspension is administered for a period from about 1 week to about 1 year.

In further embodiments, the daily dosages appropriate for the suspension described herein are from about 0.01 to about 1.0 mg/kg per body weight. In one embodiment, the daily dosages appropriate for the suspension are from about 0.02 to about 0.8 mg/kg PPI per body weight. In another embodiment, the daily dosages appropriate for the suspension are from about 0.05 to about 0.6 mg/kg PPI per body weight. In some embodiments, the daily dosage for the suspension is equivalent to about 20 mg of PPI. In some embodiments, the daily dosage for the suspension is equivalent to about 40 mg of PPI. In some embodiments, the daily dosage for the suspension is equivalent to from about 5 mg to about 100 mg of PPI.

Proton Pump Inhibitors

Proton pump inhibitors (PPIs) are medicines that work by reducing the amount of stomach acid made by glands in the lining of the stomach. PPIs are used to relieve symptoms of acid reflux or gastroesophageal reflux disease (GERD), a condition in which food or liquid moves up from the stomach to the esophagus. PPIs can be used to treat a peptic or stomach ulcer, and to treat damage to the lower esophagus caused by acid reflux. PPIs can be used to treat a variety of other diseases characterized by excessive acid secretion in the stomach, and can also be used prophylactically to manage the risk of ulceration and upper gastrointestinal tract bleeding in critical care patients. PPIs are among the most widely sold drugs in the world, and one of them, omeprazole, is on the World Health Organization's List of Essential Medicines. There are many types (and brands) of PPIs, including the product omeprazole sold under the trademark PRILOSEC®, the product esomeprazole sold under the trademark NEXIUM®, the product lansoprazole sold under the trademark PREVACID®, the product rabeprazole sold under the trademark ACIPHEX®, pantoprazole, and the product dexlansoprazole sold under the trademark DEXILANT®, all of which are available in capsule format. Some PPIs are formulated for extended release, while others are formulated for immediate release. The product omeprazole with sodium bicarbonate sold under the trademark ZEGERID® is formulated for immediate release and available as a capsule and a powder. PPIs are taken by mouth. Commonly, PPIs are taken without food, 30 minutes or more prior to the first meal of the day.

Due to the lack of alternative formulations, PPIs have been of limited use in patients who are incapable of, or have difficulty, swallowing capsules or tablets. Most PPIs are available only as enteric coated granules contained in a gelatin capsule. After dissolution of the gelatin capsule in the stomach acid, the enteric coating protects the granules from dissolution during passage through the stomach until they reach the small intestine where absorption occurs. Subsequently, one PPI, omeprazole, has become commercially available in an alternate formulation that includes omeprazole (active ingredient) with sodium bicarbonate (to protect the active ingredient from stomach acid during passage to the small intestine). This drug, the product omeprazole with sodium bicarbonate sold under the trademark ZEGERID®, may only be administered with water and, once dissolved in water from the dry powder, is supposed to be consumed immediately (i.e. not formulated for long term stability or storage). Other formulations containing PPI active ingredients are currently not available in a liquid form or are reconstitutable as a liquid.

The liquid formulations of the current invention are more palatable than the product omeprazole with sodium bicarbonate sold under the trademark ZEGERID® suspension and extemporaneously reconstituted PPIs and have enhanced stability at refrigerated conditions, ideal viscosity and significantly improved homogeneity properties. In addition, the disclosed formulations may be used to stabilize and dose PPIs other than omeprazole and lansoprazole. Non-limiting examples of the PPIs that the disclosed formulations may be used to stabilize and dose include lansoprazole, dexlansoprazole, esomeprazole, rabeprazole, and ilaprazole. In addition, as PPIs are typically dosed daily, the liquid formulations of the current invention allow a compounding pharmacy to prepare doses for many days at a consistent concentration in a convenient presentation that provides reliable delivery of API per unit dose. This provides enhanced compliance in patients over the alternate methods of making daily doses from powder packets which, in contrast, does not allow for flexible dosing. The product omeprazole with sodium bicarbonate sold under the trademark ZEGERID®, the only PPI currently available commercially as a powder for liquid dosing is labeled as requiring immediate consumption after reconstitution in water. The product omeprazole with sodium bicarbonate sold under the trademark ZEGERID® also lacks features of the current invention, such as improving the taste of the dose, while other PPI active molecules are commercially unavailable in any liquid dosage form.

Omeprazole

Omeprazole is a proton pump inhibitor that suppresses gastric acid secretion by specific inhibition of the H+/K+-ATPase in the gastric parietal cell. By acting specifically on the proton pump, omeprazole blocks the final step in acid production, thus reducing gastric acidity. It is used to treat symptoms of gastro esophageal reflux disease (GERD), esophagitis (EE), and other conditions caused by excess stomach acid. It is also used to promote healing of erosive esophagitis (damage to your esophagus caused by stomach acid). Table 1 provides the structure and general properties of omeprazole.

As used, "BCS" refers to the biopharmaceutical classification system, which classifies drugs based on their solubility and permeability. Omeprazole is a BCS Class II molecule, which means it has low solubility and high permeability. The bioavailability of BCS Class II drugs is limited by their solvation rate.

TABLE 1

Drug Information on the active pharmaceutical ingredient (API) omeprazole:

| Information | Omeprazole |
| --- | --- |
| Category | Proton Pump Inhibiter |
| Molecular Structure | (structure shown) |
| Molecular Weight | 345.417 |
| Log P | 2.43 |
| BCS Class | II |
| Melting Point | 155° C. |
| Solubility | Very slightly soluble in water |
| Dosage Form | Reconstituted Suspension |
| Route of administration | Oral |

In some embodiments, the active pharmaceutical ingredient for the suspensions disclosed herein is omeprazole. In some embodiments, the present disclosure provides an oral suspension kit comprising omeprazole powder and a diluent, as disclosed herein. In some embodiments, the omeprazole used in the compositions described herein is an omeprazole salt, such as omeprazole magnesium.

In some embodiments, the liquid formulations (specifically the reconstituted formulations) of the present invention are suspensions. Suspensions consist of flocculated particles, often containing the active ingredient, which are dispersed throughout the medium upon stirring, shaking, swirling, agitation, inversion, or a combination thereof. However, suspensions can cause the active ingredient to settle on the bottom of its container after standing for a period of time. The present disclosure provides suspensions and diluents thereof that result in a PPI suspension that is stable in terms of homogeneity. Stability in terms of homogeneity is described herein.

Processes of Preparing a PPI Oral Liquid Suspension

Also disclosed herein are processes for preparing a PPI (e.g., omeprazole) oral liquid suspension. In one aspect, the process comprises combining a PPI (e.g., omeprazole) with a liquid diluent. In some embodiments, the process further comprises mixing the PPI with the diluent. In one aspect, the process comprises the steps of (i) providing a powder (e.g., uniform powder) comprising 100% w/w of the active pharmaceutical ingredient (a PPI, e.g., omeprazole) in a bottle; (ii) adding an entire bottle of the liquid diluent, as disclosed herein (i.e. the solution component) to the bottle of API; (iii) shaking the liquid formulation for a period of time; and optionally, (iv) instructing the patient to shake the bottle well, before use.

In some embodiments, the period of time for shaking is 5, 10, 15, 20, 25, 30, 35, 40, 45, 50, 55, or 60 seconds. In some embodiments, the period of time for shaking is 1, 1.5, 2, 2.5, 3, 3.5, 4, 4.5, or 5 minutes. In some embodiments, the period of time for shaking is defined as the time required for 70%, 75%, 80%, 85%, 90%, 95% or 100% of the API to dissolve.

To exemplify, when a PPI powder is reconstituted with the inactive ingredients of the aqueous solution component, the PPI powder particles disperse into the liquid form (e.g., solution, suspension, etc.). Upon shaking the bottle containing the final product, the PPI powder particles are dispersed throughout the liquid form to provide a homogenous solution for consistent, accurate dosing for the patient. In some embodiments, the liquid form is a suspension.

Mixing methods encompass any type of mixing that result in a homogenous liquid formulation. In some embodiments, a quantity of API powder is added to a liquid vehicle and then mixed by stirring, shaking, swirling, agitation, inversion, or a combination thereof. In certain instances, a liquid vehicle is added to a quantity of API powder in a container (e.g., a bottle, vial, bag, beaker, syringe, or the like). The container is then mixed by stirring, shaking, swirling, agitation, inversion, or a combination thereof. In certain instances, a fractional volume of the liquid vehicle (e.g., one-half, one-third, one-fourth volume, etc.) is added to an API powder, mixed by stirring, shaking, swirling, agitation, inversion, or a combination thereof; and, the subsequent liquid fraction(s) is added and mixed.

General Requirements

A key problem in devising oral liquid formulations that are practical, safe, and effective to make and use, is the balance required between palatability and the handling requirements of the dose form on the one hand, and the stability of the formulation and the homogeneity of the doses on the other. Where, as in the present invention, it is desired to produce a liquid medication for oral delivery in a series of doses spread over time, it is critical to provide a formulation in which the potency of the API remains acceptably constant over the time that the formulation is to be used, so that from the first dose to last dose the same dose of active drug is delivered per unit volume of the formulation dosed to the patient. In addition, as in the case of the present invention where the API is presented as a suspension in a liquid formulation, it is necessary that the formulation is capable of providing homogenous doses. That is, that the API does not clump, settle to the bottom, float to the top, or stick to the sides of the container or any dosing or manufacturing device in a manner that would cause the dose of API contained in unit volume doses obtained from the preparation to vary unacceptably. It is generally desirable for the formulation to be sufficiently pleasant for the patient to consume and assure compliance with the regimen prescribed by the clinician, where the dose is delivered orally.

It is generally desirable for the viscosity of the liquid formulation to be low enough to facilitate handling of the formulation in the manufacture, storage, and dosing in a manner such that there are not unacceptable losses of drug, i.e., material adhering to the containers or equipment used for manufacture and storage or by adherence or clumping within the drug delivery device such as a nasogastric feeding tube. If too much drug adheres to and clumps on equipment and containers used to make, store, and deliver doses, then the delivery of API to the patient becomes unreliable, which undermines the consistency, efficacy, and safety of therapy.

As used herein, the term "viscosity" refers to a measure of a fluid's resistance to deformation by shear or tensile stress. Viscosity is informally known as the "thickness" of a liquid. Where a formulation is too viscous, unacceptable loss of product may occur at one of the steps leading to inconsistent or unreliable delivery of doses. An additional problem created by excessive viscosity is that it may render the formulation unpalatable to the patient which may decrease compliance with the desired drug regimen. Another problem created by excessive viscosity is the inability to deliver the dose through a feeding tube or similar device. It is within the scope of the invention that one skilled in the art will be able to adapt the teaching contained herein and the specific examples given below to create a suspension that balance the concerns outlined here to achieve safe, efficacious and practical formulations for the delivery of suspended PPIs. A useful formulation cannot be so viscous as to create difficulty in manufacture, transfer to the storage container, transfer to the dosing container, and transfer to the patient.

Viscosity can be determined using the methods and materials described in the United States Pharmacopeia (USP) Chapter 912. In some embodiments, the viscosity of the diluent formulations or the suspensions is between 50 and 1000 mPa·s. In some embodiments, the viscosity of the suspension or diluent is 40, 45, 50, 55, 60, 65, 70, 75, 80, 85, 90, 95, 100, 200, 300, 400, 500, 600, 700, 800, 900, or 1000 mPa·s. In some embodiments, the viscosity of the suspension or diluent is any range encompassing one or more of those viscosity values. In some embodiments, the viscosity of the diluent or suspension ranges from 100-150 mPa·s. In some embodiments, the viscosity of the diluent or suspension is 90, 92, 94, 96, 98, 100, 105, 110, 115, 120, 125, 130, 135, 140, 145, or 150 mPa·s. In some embodiments, the viscosity of the diluent or suspension is any range encompassing one or more of those viscosity values.

Freeze-Thaw Stable

Herein, it was found that the combination of sodium bicarbonate with xanthan gum, glycerin or propylene glycol results in a liquid formulation with a tendency for gel formation after the liquid formulation undergoes at least one freeze-thaw cycle. It is generally desirable that the liquid diluents of the present invention not have a tendency for gel formation when stored for long periods (e.g., 1, 5, 10, 14, 20, or 30 days) or after subjection to at least one freeze-thaw cycle.

Surprisingly, it was found that the liquid formulations of the present invention could be made with sodium CMC in lieu of xanthan gum, and, they would not have a tendency for gel formation. In some embodiments, the liquid formulations are made in the absence of glycerin or propylene glycol. This was a surprising finding since sodium CMC is an anionic water-soluble polymer, which can form ionic bridges in the present of sodium salts and ultimately lead to crosslinking Increasing amounts of sodium salt in solution can drive such a solution to higher viscosity levels. Previous studies have shown that gelation tendency and gelation strength of a methyl cellulose solution is influenced by salt type and concentration, and that increases in sodium salt concentration result in increased gel strength. Thus, in the liquid formulations of the present invention, one would expect the sodium CMC (and the combination of sodium CMC with sodium bicarbonate) to yield the undesirable gelation effect. Surprisingly, the liquid formulations of the present invention having sodium CMC did not exhibit a tendency for gel formation. Instead, the liquid formulations of the present invention were found to be freeze-thaw stable, as defined herein.

As used herein, the term "freeze-thaw stable" refers to a liquid that is resistant to gel formation after undergoing at least one freeze-thaw cycle. A freeze-thaw cycle involves the storage of a liquid in freezing temperature (e.g., −20° C.) for a period of time (e.g., a time required to partially or fully freeze the liquid, 2 h, 4 h, 6 h, 8 h, 10 h, 12 h, 14 h, 16 h, 18 h, 20 h, 24 h, 2 days, 3 days, 4 days, 5 days or longer) followed by storage of the liquid in temperatures that allow it to thaw (e.g., refrigerated temperatures, temperatures greater than refrigerated temperatures, room temperature, temperatures greater than room temperature) for a period of time that allows the liquid to thaw (e.g., a time required to partially or fully thaw the liquid, 2 h, 4 h, 6 h, 8 h, 10 h, 12 h, 14 h, 16 h, 18 h, 20 h, 24 h, 2 days, 3 days, 4 days, 5 days or longer).

The presence or absence of gel formation can be observed visually. For example, a white mass in the diluent indicates the formation of gel. The gel formed in the diluent can be isolated and analyzed. The gel can be isolated by any suitable means such as filtration and centrifugation. Accordingly, the presence of the gel can be determined by filtering or centrifuging the diluent. For example, the presence of gel residue upon filtration indicates gel formation. Suitable methods for analyzing the gel include, but are not limited to, titrimetric methods and DSC methods (see, e.g., Example 4).

Stability

The liquid formulations (e.g., diluent or suspension) described herein are stable in various storage conditions including refrigerated and ambient conditions. The term "stable", as used herein, refers to liquid formulations that maintain their appearance for a period of time (i.e. maintain homogeneity, maintain no precipitates or a small amount of precipitates, maintain color as defined by the drug specification). In some embodiments, that period of time is for at least 7 days, at least 14 days, at least 15 days, at least 1 month, at least 2 months, at least 3 months, at least 6 months, at least 9 months, at least 12 months, at least 15 months, at least 18 months, or at least 24 months. These time periods can be referred to as long term stability time periods.

In some embodiments, stability is defined by antimicrobial levels. Methods for determining stability of a liquid formulation by antimicrobial levels are known in the art.

In some embodiments, a stable suspension (also referred to as reconstituted suspension) has assay values of no less than (NLT) 90% and no more than (NMT) 110% of labeled amount of API (e.g., omeprazole). As used herein, the term "assay value" refers to the potency of a drug product measured using an HPLC method. In some embodiments, a stable suspension has assay values of about 85%, about 86%, about 87%, about 88%, about 89%, about 90%, about 91%, about 92%, about 93%, about 94%, about 95%, about 96%, about 97%, about 98%, about 99%, about 100%, about 101%, about 102%, about 103%, about 104%, about 105%, about 106%, about 107%, about 108%, about 109% or about 110% of labeled API (e.g., omeprazole). In some embodiments, a stable suspension has assay values of labeled API of a range encompassing one or more of those values. In some embodiments, the assay values for labeled API have less than 2% relative standard deviation (RSD). In some embodiments the % RSD for assay is about 0%, about 0.1%, about 0.2%, about 0.3%, about 0.4%, about 0.5%, about 0.6%, about 0.7%, about 0.8%, about 0.9%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4, or about 2.5%. In some embodiments, the % RSD for assay is a range encompassed by one or more of those values.

In some embodiments, the API in a stable suspension has at least about 85% w/w, at least about 86% w/w, at least about 87% w/w, at least about 88% w/w, at least about 89% w/w, at least about 90% w/w, at least about 91% w/w, at least about 92% w/w, at least about 93% w/w, at least about 94% w/w, at least about 95% w/w, at least about 96% w/w, at least about 97% w/w, at least about 98% w/w, at least about 99% w/w, or at least about 100% w/w of the initial API amount after a given storage period. In some embodiments, the API in a stable suspension has at most about 115% w/w, at most about 110% w/w, at most about 109% w/w, at most about 108% w/w, at most about 107% w/w, at most about 106% w/w, at most about 105% w/w, at most about 104% w/w, at most about 103% w/w, at most about 102% w/w, at most about 101% w/w, or at most about 100% w/w of the initial API amount after a given storage period. In some embodiments, the API in a stable suspension is within the range of about 100±15% w/w, about 100±10% w/w, about 100±9% w/w, about 100±8% w/w, about 100±7% w/w, about 100±6% w/w, about 100±5% w/w, about 100±4% w/w, about 100±3% w/w, about 100±2.5% w/w, about 100±2.0% w/w, about 100±1.5% w/w, about 100±1.0% w/w, or about 100±0.5% w/w of the initial API amount after a given storage period. In some embodiments, the API amount is determined by liquid chromatography such as high performance liquid chromatography (HPLC). In some embodiments, the total impurities in a stable suspension is no more than about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2.0% w/w, about 2.1% w/w, about 2.2% w/w, about 2.3% w/w, about 2.4 w/w, or about 2.5% w/w based on the weight of the suspension after a given storage period. In some embodiments, the total impurities in a stable suspension is no more than about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, or about 10% w/w based on the weight of the suspension after a given storage period.

In some embodiments, the total impurities in a stable suspension is no more than about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2.0% w/w, about 2.1% w/w, about 2.2% w/w, about 2.3% w/w, about 2.4 w/w, or about 2.5% w/w based on the weight of the initial API amount after a given storage period. In some embodiments, the total impurities in a stable suspension is no more than about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, or about 10% w/w based on the weight of the initial API amount after a given storage period. In some embodiments, the total impurity is determined by liquid chromatography, such as high performance liquid chromatography (HPLC).

In some embodiments, a stable liquid formulation of the present invention has about 5%, about 4%, about 3%, about 2.5%, about 2%, and 1.5%, about 1%, or about 0.5% individual impurities or substances. The % value is relative to the active ingredient peak. Percent refers to peak area to peak area. In some embodiments, a stable liquid formulation of the present invention has individual known and unknown impurity levels that are less than 0.1%, less than 0.2%, less than 0.3%, less than 0.4%, less than 0.5%, less than 0.6%, less than 0.7%, less than 0.8%, less than 0.9%, or less than 1.0%. In some embodiments, the range of known and unknown impurity levels for a stable liquid formulation of the present invention is a range encompassing one or more of those values.

At ambient conditions or refrigerated conditions, the liquid formulations described herein are stable, in some embodiments, that is for at least 7 days, at least 14 days, at least 15 days, at least 1 month, at least 2 months, at least 3 months, at least 6 months, at least 9 months, at least 12 months, at least 15 months, at least 18 months, or at least 24 months. These time periods can be referred to as long term stability time periods.

In some embodiments, the liquid diluent is stable at ambient temperature for at least 7 days, at least 14 days, at least 15 days, at least 1 month, at least 2 months, at least 3 months, at least 6 months, at least 9 months, at least 12 months, at least 15 months, at least 18 months, or at least 24 months. In some embodiments, the liquid diluent is stable at refrigerated temperature for at least 7 days, at least 14 days, at least 15 days, at least 1 month, at least 2 months, at least 3 months, at least 6 months, at least 9 months, at least 12 months, at least 15 months, at least 18 months, or at least 24 months.

In some embodiments, the liquid suspension is stable at ambient temperature for at least 7 days, at least 14 days, at least 15 days, at least 1 month, at least 2 months, at least 3 months, at least 6 months, at least 9 months, or at least 12 months. In some embodiments, the liquid suspension is stable at refrigerated temperature for at least 7 days, at least 14 days, at least 15 days, at least 1 month, at least 2 months, at least 3 months, at least 6 months, at least 9 months, or at least 12 months.

In some embodiments, a stable liquid diluent is resistant to gel formation. In some embodiments, a stable liquid diluent is free of gel formation following at least one freeze-thaw cycle. In some embodiments, after a given storage period, a stable liquid diluent is free of gel formation following at least one freeze-thaw cycle. In some embodiments, a stable liquid diluent is free of gel formation following at least two freeze-thaw cycles. In some embodiments, after a given storage period, a stable liquid diluent is free of gel formation following at least two freeze-thaw cycles. In some embodiments, a stable liquid diluent is free of gel formation following at least three freeze-thaw cycles. In some embodiments, after a given storage period, a stable liquid diluent is free of gel formation following at least three freeze-thaw cycles.

Refrigerated and Ambient Temperatures

Refrigerated temperature, also as defined by the USP, is between 2 and 8 degrees Celsius, and is sometimes designated by the nominal value of 5 degrees Celsius. In some embodiments, refrigerated temperatures can be defined as 5±3° C. In each case, the formulations of the invention that were shown to be stable showed acceptable recovery of the expected API from the dose, where acceptable is >95% or alternately >90% of the nominal or starting dose of API, as well as maintaining acceptably constant pH and acceptably constant acid neutralization potential. Refrigerated conditions include temperature and/or relative humidity (RH) in typical refrigeration units (e.g., 5±3° C.). In some instances, a refrigerated condition is about 2° C., about 3° C., about 4° C., about 5° C., about 6° C., about 7° C., or about 8° C.

As used herein, the term "ambient temperature" refers to room temperature or "controlled room temperature". Ambient conditions include temperature and/or relative humidity (RH). As used herein, the term "ambient conditions" refer to room temperature and relative humidity. In some embodiments, the ambient conditions are 25±5° C. and 60±5% RH. In some instances, an ambient condition is at about 20° C., about 21° C., about 22° C., about 23° C., about 24° C., about 25° C., about 26° C., about 27° C., about 28° C., about 29° C., and about 30° C. In other instances, an ambient condition is about 45% RH, about 50% RH, about 55% RH, about 60% RH, or about 65% RH. In some embodiments, the ambient conditions are 25±2° C. and 60±5% RH.

Suspending Agents

A thickening agent, or suspending agent, may be added to prepare a suspension from a solution. Suspending agents are agents which facilitate the suspension and, in some cases, the dissolution of an active agent in a solvent or solution component. Generally, suspending agents ensure more uniform mixing of active and solution components. In order to administer a more uniform dose of a reconstituted pharmaceutical to a patient, the reconstituted suspension must be properly and homogeneously combined. If the active agent is present as a powder, a uniform dispersion is sometimes difficult to achieve using the traditional form of compounding.

Non-limiting examples of suspending agents include sodium CMC, xanthan gum, hydroxyl ethyl cellulose (HEC), hydroxyl propyl methyl cellulose (HPMC), and Avicel CL-611. Further exemplary suspending agents include carboxymethylcellulose (sodium and other salts), carboxymethylhydroxyethylcellulose, carboxy-vinyl copolymers, cellulose, such as microcrystalline cellulose, combinations of microcrystalline cellulose with sodium carboxymethylcellulose (such as Avicel RC-501, RC-581, RC-591, and CL-611), hydrophobically modified hydroxyethyl cellulose, hydroxyethyl cellulose, hydroxypropyl guar, hydroxypropyl methylcellulose (such as Benecel K750 ® or Benecel K1500®), hydroxypropyl cellulose, methyl cellulose, natural gums and their derivatives, xanthan gum, guar gum, gum Arabic, partially and fully hydrolyzed polyvinyl alcohols, partially neutralized polyacrylic acid, polyalkylene glycol, polysaccharide gums, polyvinylpyrrolidone and derivatives thereof, starch and its derivatives, vinylpyrrolidone homo- and copolymers, water-soluble cellulose ethers, and the mixtures thereof. In preferred embodiments, the suspending agent in the liquid formulations of the present invention is sodium CMC.

A subcategory of suspending agents is solubilizers. Solubilizers are agents which facilitate the dissolution of a solid or, in some cases, a semi-solid agent in a solution component. In some embodiments of the invention, a solid-form active agent may be dissolved in a suspending agent, prior to mixing it with the solution component. Conversely, the suspending agent and the solution component may be pre-packaged together, particularly if the concern is ensuring the uniform blending of active agent within the solution component rather than the loss of solid (i.e., powdery) active agent. In still other variations, the suspending agent may be premixed with solution component.

Non-limiting examples of suspending agents useful in the compositions of the invention include, but are not limited to, glycerin, hexylene glycol, propylene glycol, sorbitol, acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 Stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monstearate, stearic acid, trolamine, emulsifying wax, benzalkonium chloride, benzethonium chloride, cetylpyridinium chloride, docusate sodium, nonoxynol 9, nonoxynol 10, Octoxynol 9, polyoxyl 50 Stearate, and tyloxapol.

Still other suspending agents include humectants and wetting agents. Humectants are agents which retain moisture. Examples of humectants include, but are not limited to, glycerin, hexylene glycol, propylene glycol, and sorbitol. (See, for example, US Publication No. US 2004/0191276, herein incorporated by reference).

In some embodiments of the present disclosure, the concentration of sodium CMC in the diluent or reconstituted suspension is 0.5%-3.0%, 0.5%-2.5%, 0.5%-2.0%, 0.5%-1.5%, 0.5%-1.0%, 0.5%-0.8%, 1.0%-3.0, 1.0%-2.8%, 1.0%-2.5%, 1.0%-2.3%, 1.0%-2.0%, 1.0%-1.5%, 1.5%-3.0%, 1.5%-2.5%, 1.5%-2.0%, 1.5%-1.8%, 2.0%-3.0%, 2.0%-2.5%, 2.5%-3.0% w/v sodium CMC or some range or value therein.

In some embodiments of the present disclosure, the concentration of sodium CMC in the diluent or reconstituted suspension is 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, or 2.5% w/v sodium CMC.

In some embodiments, the sodium CMC has a weight average molecular weight of from about 50k Da to about 1,000k Da, from about 70k Da to about 800k Da, from about 100k Da to about 500k Da, from about 200k Da to about 350k Da, or from about 250k Da to about 300k Da. In some embodiments, the sodium CMC has a weight average molecular weight of from about 250k Da to about 300k Da.

In some embodiments, the sodium CMC has a degree of substitution (DS) from about 0.1 to about 3.0, from about 0.5 to about 1.5, from about 0.5 to 1.0 or from about 0.75 to about 0.85. In some embodiments, the sodium CMC has a degree of substitution of from about 0.75 to about 0.85.

In some embodiments of the present disclosure, the concentration of the suspending agent (such as sodium CMC) is about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1.0% w/v, about 1.1% w/v, about 1.2% w/v, about 1.3% w/v, about 1.4% w/v, about 1.5% w/v, about 1.6% w/v, about 1.7% w/v, about 1.8% w/v, about 1.9% w/v, about 2.0% w/v, about 2.1% w/v, about 2.2% w/v, about 2.3% w/v, about 2.4% w/v, about 2.5% w/v, about 2.6% w/v, about 2.7% w/v, about 2.8% w/v, about 2.9% w/v, about 3.0% w/v, about 3.1% w/v, about 3.2% w/v, about 3.3% w/v, about 3.4% w/v, about 3.5% w/v, about 3.6% w/v, about 3.7% w/v, about 3.8% w/v, about 3.9% w/v, about 4.0% w/v, about 4.1% w/v, about 4.2% w/v, about 4.3% w/v, about 4.4% w/v, about 4.5% w/v, about 4.6% w/v, about 4.7% w/v, about 4.8% w/v, about 4.9% w/v, or about 5.0% w/v in the diluent or in the reconstituted suspension. In some embodiments of the present disclosure, the concentration of the suspending agent (such as sodium CMC) is from about 0.5% w/v to about 2.5% w/v, from about 0.5% w/v to about 2.0% w/v, or from about 1.0% w/v to about 1.4% w/v in the diluent or in the reconstituted suspension.

Surfactants

"Surfactants" can be defined as surface-active amphiphilic compounds such as block co-polymers. They can be referred to as wetting agents. Non-limiting examples of surfactants include a poloxamer (e.g., poloxamer 188), sodium lauryl sulfate, and polysorbate 80. In preferred embodiments, the surfactant used in the liquid formulations of the present invention is poloxamer 188. Non-limiting examples of surfactants are provided in US Publication No. US 2015/0238613 and U.S. Pat. No. 7,815,933, herein incorporated by reference.

The surfactant used in the present disclosure can be a non-ionic surfactant. A non-ionic surfactant has no charged groups in its head. Exemplary nonionic surfactants include, without limitation, fatty alcohols, cetyl alcohol, stearyl alcohol, cetostearyl alcohol, and oleyl alcohol. Exemplary nonionic surfactants include, but are not limited to, polyethylene glycol alkyl ethers (such as octaethylene glycol monododecyl ether, pentaethylene glycol monododecyl ether), polypropylene glycol alkyl ethers, glucoside alkyl ethers (such as decyl glucoside, lauryl glucoside, octyl glucoside), polyethylene glycol octylphenyl ethers (such as Triton X-100), polyethylene glycol alkylphenyl ethers (such as nonoxynol-9), glycerol alkyl esters (such as glyceryl laurate), polyoxyethylene glycol sorbitan alkyl esters (such as polysorbate), sorbitan alkyl esters (such as Spans), cocamide MEA, cocamide DEA, dodecyldimethylamine oxide, block copolymers of polyethylene glycol and polypropylene glycol (such as poloxamers), and polyethoxylated tallow amine (POEA). In some embodiments, the surfactant is a non-ionic surfactant that comprises polyethylene glycol. In some embodiments, the surfactant is a block copolymer of polyethylene glycol and polypropylene glycol.

In some embodiments, the non-ionic surfactant has a number average molecular weight of from about from about 1000 to about 100,000 Da, 2000 to about 20,000 Da, from about 4000 to about 15,000 Da, from about 6000 to about 12,000 Da, or from about 7000 to about 10,000 Da. In some embodiments, the non-ionic surfactant has a number average molecular weight of from about 7000 to about 10,000 Da. In some embodiments, the non-ionic surfactant has an ethylene glycol content of from about 30 wt % to about 99 wt %, from about 50 wt % to about 95 wt %, from about 60 wt % to about 95 wt %, from about 75 wt % to about 90 wt %, or from about 80 wt % to about 85 wt %. In some embodiments, the non-ionic surfactant has an ethylene glycol content of from about 80 wt % to about 85 wt %.

The surfactant used in the present disclosure can be a cationic surfactant. Cationic surfactants include pH-dependent primary, secondary, or tertiary amines such as octenidine dihydrochloride; and permanently charged quaternary ammonium salts such as cetrimonium bromide (CTAB), cetylpyridinium chloride (CPC), benzalkonium chloride (BAC), benzethonium chloride (BZT), dimethyldioctadecylammonium chloride, and dioctadecyldimethylammonium bromide (DODAB).

The surfactant used in the present disclosure can comprise an anionic surfactant. Anionic surfactants contain anionic functional groups at their head, such as sulfate, sulfonate, phosphate, and carboxylates. Exemplary anionic surfactants include, but are not limited to, ammonium lauryl sulfate, sodium lauryl sulfate (sodium dodecyl sulfate, SLS, or SDS), and the related alkyl-ether sulfates sodium laureth sulfate (sodium lauryl ether sulfate or SLES), sodium myreth sulfate, docusate (dioctyl sodium sulfosuccinate), perfluorooctanesulfonate (PFOS), perfluorobutanesulfonate, alkyl-aryl ether phosphates, and alkyl ether phosphates. The surfactant used in the present disclosure can be a zwitterionic surfactant. Zwitterionic (amphoteric) surfactants refer to those having cationic and anionic centers attached to the same molecule. Exemplary zwitterionic surfactants include, without limitation, phospholipids phosphatidylserine, phosphatidylethanolamine, phosphatidylcholine, and sphingomyelins.

In some embodiments of the present disclosure, the concentration of poloxamer (e.g., poloxamer 188) in the diluent or reconstituted suspension is 0.5%-4.0%, 0.5%-3.5%, 0.5%-3.0%, 0.5%-2.5%, 0.5%-2.0%, 0.5%-1.5%, 0.5%-1.0%, 1.0%-4.0%, 1.0%-3.5%, 1.0%-3.0%, 1.0%-2.5%, 1.0%-2.0%, 1.0%-1.5%, 1.5%-4.0%, 1.5%-3.5%, 1.5%-3.0%, 1.5%-2.5%, 1.5%-2.0%, 2.0%-4.0%, 2.0%-3.5%, 2.0%-3.0%, 2.0%-2.5%, 2.5%-4.0%, 2.5%-3.5%, 2.5%-3.0%, 3.0%-4.0%, 3.0%-3.5%, 3.5%-4.0% w/v poloxamer (e.g., poloxamer 188) or some range or value therein.

In some embodiments of the present disclosure, the concentration of poloxamer (e.g., poloxamer 188) in the diluent or reconstituted suspension is 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, or 4.0% w/v poloxamer (e.g., poloxamer 188).

In some embodiments of the present disclosure, the concentration of the surfactant (such as poloxamer (e.g., poloxamer 188)) is about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1.0% w/v, about 1.1% w/v, about 1.2% w/v, about 1.3% w/v, about 1.4% w/v, about 1.5% w/v, about 1.6% w/v, about 1.7% w/v, about 1.8% w/v, about 1.9% w/v, about 2.0% w/v, about 2.1% w/v, about 2.2% w/v, about 2.3% w/v, about 2.4% w/v, about 2.5% w/v, about 2.6% w/v, about 2.7% w/v, about 2.8% w/v, about 2.9% w/v, about 3.0% w/v, about 3.1% w/v, about 3.2% w/v, about 3.3% w/v, about 3.4% w/v, about 3.5% w/v, about 3.6% w/v, about 3.7% w/v, about 3.8% w/v, about 3.9% w/v, about 4.0% w/v, about 4.1% w/v, about 4.2% w/v, about 4.3% w/v, about 4.4% w/v, about 4.5% w/v, about 4.6% w/v, about 4.7% w/v, about 4.8% w/v, about 4.9% w/v, or about 5.0% w/v in the diluent or in the reconstituted suspension. In some embodiments of the present disclosure, the concentration of the surfactant (such as poloxamer (e.g., poloxamer 188)) is from about 0.5% w/v to about 4.0% w/v, from about 0.5% w/v to about 8.0% w/v, from about 0.5% w/v to about 15% w/v, from about 0.75% w/v to about 4.0% w/v, from about 0.75% w/v to about 8.0% w/v, from about 0.75% w/v to about 15% w/v, from about 1.0% w/v to about 4.0% w/v, from about 1.0% w/v to about 8.0% w/v, or from about 1% w/v to about 15% w/v in the diluent or in the reconstituted suspension.

Buffers

While sodium citrate and sodium bicarbonate are the buffers used in some embodiments of the present invention, this is a non-limiting example of the buffers that can be used in the present invention. Other buffers include pharmacologically acceptable combinations of cations selected from sodium, potassium, magnesium, calcium, and aluminum and anions selected from bicarbonate, hydroxide, gluconate, glycinate, and other appropriate amino acid salts. Additional buffering agents can include other forms of citrate, tartrates, acetates, carbonates, phosphates, metaphosphates, glycerophosphates, polyphosphates, pyrophosphates, and certain oxides in pharmacologically and pharmaceutically acceptable combinations of anions and cations providing buffering capacity as known in the art.

In some embodiments, the buffers used in the liquid formulations of the present invention comprise at least one of sodium bicarbonate and sodium citrate. In some embodiments of the present disclosure, the concentration of buffer is 0.5%-0.6%, 0.5%-0.7%, 0.5%-0.8%, 0.5%-0.9%, 0.5%-1%, 0.5%-1.1%, 0.5%-1.2%, 0.5%-1.3%, 0.5%-1.4%, 0.5%-1.5% w/v or any range or number therein. In some embodiments, the concentration of buffer is 0.5%, 0.55%, 0.6%, 0.65%, 0.7%, 0.75%, 0.8%, 0.85%, 0.9%, 0.95%, 1%, 1.05%, 1.1%, 1.15%, 1.2%, 1.25%, 1.3%, 1.35%, 1.4%, 1.45% or 1.5% w/v.

In some embodiments, the buffer is present at about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1.0% w/v, about 1.1% w/v, about 1.2% w/v, about 1.3% w/v, about 1.4% w/v, about 1.5% w/v, about 1.6% w/v, about 1.7% w/v, about 1.8% w/v, about 1.9% w/v, about 2.0% w/v, about 2.1% w/v, about 2.2% w/v, about 2.3% w/v, about 2.4% w/v, about 2.5% w/v, about 2.6% w/v, about 2.7% w/v, about 2.8% w/v, about 2.9% w/v, about 3.0% w/v, about 3.1% w/v, about 3.2% w/v, about 3.3% w/v, about 3.4% w/v, about 3.5% w/v, about 3.6% w/v, about 3.7% w/v, about 3.8% w/v, about 3.9% w/v, or about 4.0% w/v in the diluent or in the reconstituted suspension. In some embodiments, the buffer is present from about 0.5% w/v to about 1.5% w/v, from about 0.2% w/v to about 2.0% w/v, from about 0.1% w/v to about 5.0% w/v, or from about 0.01% w/v to about 10.0% w/v in the diluent or in the reconstituted suspension.

In some embodiments, the buffer is present to maintain a pH of about 8-9.5.

Acid Neutralizing Agents

In some embodiments, the diluent or reconstituted suspensions of the present disclosure comprise of an acid neutralizing agent. These are agents that have a high base dissociation constant ($pK_b$). When PPIs are administered they are subject to degradation by acid, e.g., gastric acids. Many commercially available are encapsulated or enterically coated to avoid this. In the reconstituted suspensions of the present disclosure, this problem can be circumvented with an acid neutralizing agent. These acid neutralizing agents raise the local pH near the API (e.g., PPI, e.g., omeprazole) in the reconstituted suspension. Non-limiting examples of acid neutralizing agents include sodium bicarbonate, calcium carbonate, alkali metal or alkaline earth metal salts (e.g., sodium, potassium and magnesium salts), aluminum salts, ammonium and bismuth salts.

In some embodiments of the present disclosure, the acid neutralizing contemplated is sodium bicarbonate. In some embodiments, the range of acid neutralizing agent (e.g., sodium bicarbonate is 8.0%-8.1%, 8.0%-8.2%, 8.0%-8.3%, 8.0%-8.4%, 8.0%-8.5%, 8.0%-8.6%, 8.0%-8.7%, 8.0%-8.8%, 8.0%-8.9%, 8.0%-9.0%, 8.1%-8.2%, 8.1%-8.3%, 8.1%-8.4%, 8.1%-8.5%, 8.1%-8.6%, 8.1%-8.7%, 8.1%-8.8%, 8.1%-8.9%, 8.1%-9.0%, 8.2%-8.3%, 8.2%-8.4%, 8.2%-8.5%, 8.2%-8.6%, 8.2%-8.7%, 8.2%-8.8%, 8.2%-8.9%, 8.2%-9.0%, 8.3%-8.4%, 8.3%-8.5%, 8.3%-8.6%, 8.3%-8.7%, 8.3%-8.8%, 8.3%-8.9%, 8.3%-9.0%, 8.4%-8.5%, 8.4%-8.6%, 8.4%-8.7%, 8.4%-8.8%, 8.4%-8.9%, 8.4%-9.0%, 8.5%-8.6%, 8.5%-8.7%, 8.5%-8.8%, 8.5%-8.9%, 8.5%-9.0%, 8.6%-8.7%, 8.6%-8.8%, 8.6%-8.9%, 8.6%-9.0%, 8.7%-8.8%, 8.7%-8.9%, 8.7%-9.0%, 8.8%-8.9%, 8.8%-9.0%, 8.9%-9.0% w/v or any range or value therein.

In some embodiments, the acid neutralizing agent is present from about 8.0% w/v to about 8.8% w/v, from about 7.8% w/v to about 9.0% w/v, from about 6.0% w/v to about 8.8% w/v, or from about 4.0% w/v to about 15% w/v in the diluent or in the reconstituted suspension. In some embodiments, the acid neutralizing agent is present from about 4% w/v to about 15% w/v or from about 2% w/v to about 20% w/v in the diluent or in the reconstituted suspension. In some embodiments, the acid neutralizing agent is present at about 6.1% w/v, about 6.2% w/v, about 6.3% w/v, about 6.4% w/v, about 6.5% w/v, about 6.6% w/v, about 6.7% w/v, about 6.8% w/v, about 6.9% w/v, about 7.0% w/v, about 7.1% w/v, about 7.2% w/v, about 7.3% w/v, about 7.4% w/v, about 7.5% w/v, about 7.6% w/v, about 7.7% w/v, about 7.8% w/v, about 7.9% w/v, about 8.0% w/v, about 8.1% w/v, about 8.2% w/v, about 8.3% w/v, about 8.4% w/v, about 8.5% w/v, about 8.6% w/v, about 8.7% w/v, about 8.8% w/v, about 8.9% w/v, about 9.0% w/v, about 9.1% w/v, about 9.2% w/v, about 9.3% w/v, about 9.4% w/v, about 9.5% w/v, about 9.6% w/v, about 9.7% w/v, about 9.8% w/v, about 9.9% w/v, or about 10.0% w/v in the diluent or in the reconstituted suspension.

Defoamer

A defoamer (also referred to as an anti-foaming agent) is a chemical agent that reduces and/or hinders the formation of foam in liquid formulations. They are classified into oil-based defoamers (e.g., mineral oil, vegetable oil, white oil, etc.), powder defoamers, water-based defoamers, silicon-based defoamers (e.g., polymers with silicon backbones), ethylene oxide/propylene oxide-based (EO/PO-based) defoamers (e.g., contain polyethylene glycol and polypropylene glycol copolymers), and alkyl polyacrylates.

In pharmaceutical compositions, defoamers are sometimes marketed in drugs that relieve bloating. Non-limiting examples of defoamers include simethicone emulsion, poly dimethyl siloxane, dimethicone, ethanol, and ether.

While not excluding the possibility that other ingredients contribute to the stability of the liquid formulations of the present invention, the use of simethicone emulsion contributes to stability by minimizing the formation of foam on mixing or agitation during formulation, or incidentally during transport, use, and storage. The formation of foam could be associated with conditions denaturing the API or conditions that would diminish the patient's ability to measure an exact dose.

In some embodiments of the present disclosure, the defoamer is simethicone emulsion. In some embodiments, the simethicone emulsion contains 30% w/w simethicone. In some embodiments, the defoamer is a pure simethicone. In some embodiments, the concentration of defoamer is 0.10%-0.11%, 0.10%-0.12%, 0.10%-0.13%, 0.10%-0.14%, 0.10%-0.15%, 0.10%-0.16%, 0.10%-0.17%, 0.10%-0.18%, 0.10%-0.19%, 0.10%-0.2%, 0.10%-0.21%, 0.10%-0.22%, 0.10%-0.23%, 0.10%-0.24%, 0.10%-0.25%, 0.10%-0.26%, 0.10%-0.27%, 0.10%-0.28%, 0.10%-0.29%, 0.10%-0.30% w/v or any range or value therein. In some embodiments, the concentration of defoamer is 0.1%, 0.11%, 0.12%, 0.13%, 0.14%, 0.15%, 0.16%, 0.17%, 0.18%, 0.19%, 0.2%, 0.21%, 0.22%, 0.23%, 0.24%, 0.25%, 0.26%, 0.27%, 0.28%, 0.29% or 0.3% w/v. In some embodiments, the w/v percentage of the simethicone in the liquid formulation is based on the total weight of the simethicone emulsion.

In some embodiments, the defoamer is present at about 0.01% w/v, about 0.02% w/v, about 0.05% w/v, about 0.08% w/v, about 0.1% w/v, about 0.15% w/v, about 0.2% w/v, about 0.25% w/v, about 0.3% w/v, about 0.35% w/v, about 0.4% w/v, about 0.45% w/v, about 0.5% w/v, about 0.55% w/v, about 0.6% w/v, about 0.65% w/v, about 0.7% w/v, about 0.75% w/v, about 0.8% w/v, about 0.85% w/v, about 0.9% w/v, about 0.95% w/v, about 1.0% w/v, about 1.1% w/v, about 1.2% w/v, about 1.3% w/v, about 1.4% w/v, or about 1.5% w/v in the diluent or in the reconstituted suspension. In some embodiments, the defoamer is present from about 0.1% w/v to about 0.3% w/v, from about 0.05% w/v to about 0.6% w/v, from about 0.01% w/v to about 1.0% w/v, or from about 0.01% w/v to about 1.5% w/v in the diluent or in the reconstituted suspension.

Preservatives

Preservatives added include anti-microbials, anti-oxidants, and agents providing biocidal or biostatic activity, such that a low bioburden is maintained in the formulation of the invention from preparation through storage, and during routine use by patients and clinicians. Exemplary preservatives include benzyl alcohol or other pharmaceutically acceptable alcohol, ascorbic acid, ascorbyl palmitate or other pharmaceutically acceptable ascorbate salts, BHA, BHT, citric acid or other citrate salts, sodium benzoate, benzoic acid or other pharmaceutically acceptable benzoate salts, sodium bisulfate, sodium metabisulfite, sodium sulfite, parabens, potassium sorbate or other pharmaceutically acceptable sorbate salts, or vanillin.

In some embodiments of the present disclosure, the preservative is benzyl alcohol. In some embodiments, the concentration of the preservative (e.g., benzyl alcohol) is 0.40%-0.41%, 0.40%-0.42%, 0.40%-0.43%, 0.40%-0.44%, 0.40%-0.45%, 0.40%-0.46%, 0.40%-0.47%, 0.40%-0.48%, 0.40%-0.49%, 0.40%-0.5%, 0.40%-0.51%, 0.40%-0.52%, 0.40%-0.53%, 0.40%-0.54%, 0.40%-0.55%, 0.40%-0.56%, 0.40%-0.57%, 0.40%-0.58%, 0.40%-0.59%, 0.40%-0.6% w/v or any range or value therein. In some embodiments of the present disclosure, the preservative is benzyl alcohol. In some embodiments, the concentration of benzyl alcohol is 0.4%, 0.41%, 0.42%, 0.43%, 0.44%, 0.45%, 0.46%, 0.47%, 0.48%, 0.49%, 0.5%, 0.51%, 0.52%, 0.53%, 0.54%, 0.55%, 0.56%, 0.57%, 0.58%, 0.59% or 0.6% w/v in the diluent or in the reconstituted suspension.

In some embodiments, the preservative (e.g., benzyl alcohol) is present from about 0.4% w/v to about 0.6% w/v, from about 0.2% w/v to about 1.2% w/v, from about 0.1% w/v to about 2.5% w/v, or from about 0.05% w/v to about 5.0% w/v in the diluent or in the reconstituted suspension.

Sweeteners & Flavoring Agents

Sweeteners or sweetening agents may include any compounds that provide a sweet taste to enhance the palatability of the formulation, including natural and synthetic sugars and natural and synthetic sweeteners (i.e., non-sugar sweetening agents). These could include glucose, fructose, sucrose, or other pharmaceutically acceptable monosaccharides and disaccharides or sugar alcohols, such as xylitol. Also, sweeteners may include maltodextrin, polydextrose and the like. Other sweeteners may include glycerin, inulin, maltol, salts of acesulfame, alitame, aspartame, neotame, cyclamate salts, sucralose, sorbitol solution, saccharin and its salts, and other artificial and naturally-occurring agents providing sweetness either singly or in combination.

In some embodiments of the present disclosure, the diluent or reconstituted suspension has a combination of sweeteners (e.g., sucralose and sorbitol solution). In some embodiments, the diluent or reconstituted suspension has 0.35%-0.5%, 0.35%-1.0%, 0.35%-1.5%, 0.35%-2.0%, 0.35%-2.5%, 0.35%-3.0%, 0.35%-3.5%, 0.5%-1.0%, 0.5%-1.5%, 0.5%-2.0%, 0.5%-2.5%, 0.5%-3.0%, 0.5%-3.5%, 1.0%-1.5%, 1.0%-2.0%, 1.0%-2.5%, 1.0%-3.0%, 1.0%-3.5%, 1.5%-2.0%, 1.5%-2.5%, 1.5%-3.0%, 1.5%-3.5%, 1.5%-4.0%, 2.0%-2.5%, 2.0%-3.0%, 2.0%-3.5%, 2.0%-4.0%, 2.5%-3.0%, 2.5%-3.5%, 2.5%-4.0%, 3.0%-3.5%, 3.0%-4.0%, 3.5%-4.0% w/v of sweetener or any ranges or values contemplated therein. In some embodiments, the sweetener or the combination of sweeteners is present from about 0.35% w/v to about 3.5% w/v, from about 0.2% w/v to about 7.0% w/v, from about 0.1% w/v to about 10% w/v, or from about 0.1% w/v to about 15% w/v in the diluent or in the reconstituted suspension.

In other embodiments, the liquid formulations comprise a flavoring agent or flavorant to enhance the flavor or aroma of the dose, and to improve general palatability of the dose, thus helping to mask the flavor of the PPI active ingredient which patients may find unpleasant. This provides an improved experience for patients, and better compliance with the drug regimen desired by clinicians. Suitable natural or artificial flavors can be selected from pharmaceutically acceptable options as described in standard pharmacy references which are known to those skilled in the art. Suitable natural or synthetic flavoring agents can be selected from standard reference books, such as Remington: *The Science and Practice of Pharmacy* (2000) and *Fenaroli's Handbook of Flavor Ingredients* (1994).

Non-limiting examples of suitable natural flavors, some of which can be readily simulated with synthetic agents or combinations thereof, include almond, anise, apple, apricot, banana, blackberry, blackcurrant, blueberry, caramel, cherry, chocolate, cinnamon, cranberry, grape, lemon, lime, orange, peppermint, pineapple, raspberry, spearmint, strawberry, vanilla, etc. In some embodiments, the flavors include which can be readily simulated with synthetic agents or combinations thereof include fat, poultry, fish, beef, and other meats. In a particular embodiment, strawberry flavor (e.g., Strawberry Flavor CW08) is used. The use of strawberry flavor has been found to be effective in helping to mask the unpleasant flavor of omeprazole. In other embodiments, other pharmaceutically acceptable flavors can be used to mask the flavor of other ingredients, for example other PPI APIs, and to enhance palatability and thus compliance in a range of patient populations. Natural and synthetic flavors can be used and adapted to the palate of diverse patient populations, including but not limited to, age- and culturally-related flavor preferences (for example bubble gum flavor for pediatric patients).

Coloring Agents

In further embodiments, the liquid formulation may contain a pharmaceutically acceptable coloring agent. Many such agents are approved for use by the U.S. Food and Drug Administration, and are well known to those skilled in the art of compounding pharmacy. Suitable coloring agents approved by the U.S. Food and Drug Administration (FDA) include FD&C Red No. 3, FD&C Red No. 20, FD&C Red No. 40, FD&C Yellow No. 6, FD&C Blue No. 2, D&C Green No. 5, D&C Orange No. 5, D&C Yellow No. 10, caramel, ferric oxide and mixtures thereof.

The use of color can enhance the aesthetic appearance of the dose as well as providing confirmation of the identity of the drug in a context where more than one oral formulation is being prepared, stored, transported, or used. Enhancing the aesthetic appearance of the dose increases the overall palatability of the dose, which provides benefits to patients and clinicians in terms of improved patient experience and improved compliance with the drug regimen. The ability to unambiguously identify the medication in the pharmacy, clinical, and patient context provides benefits to the patient by reducing the scope for errors in the preparation, storage, handling, transport, and use of the medication. In addition, the use of color in the formulations can mask color changes in the formulation lacking additional color agents. For example, uncolored formulations may change color due to chemical changes taking place during storage that do not affect the safety, potency, or efficacy of the medication, but that might confuse a patient or clinician, or that might lead to a lack of compliance with a prescribed drug regimen.

In some embodiments of the present disclosure, the coloring agent is FD&C Red No. 40. However, any FDA-approved coloring agent is contemplated herein. In some embodiments, the concentration of coloring agent is 0.002%-0.005%, 0.002%-0.004%, 0.002%-0.003% w/v or any range or value therein. In some embodiments, the concentration of coloring agent is less than 0.002%. In some embodiments, the concentration of coloring agent is greater than 0.005%.

Pharmaceutical Compositions

The liquid formulations (e.g., diluents and suspensions) of the present invention can also be referred to as pharmaceutical compositions. Furthermore, a pharmaceutical composition, as provided in the present disclosure can be used to treat a subject having a gastrointestinal disorder. In some embodiments, the diluents and/or suspensions of the present disclosure are pharmaceutically acceptable formulations.

Specific examples are provided herein of pharmaceutically acceptable formulations that achieve appropriate homogeneity and stability in useful, practical and palatable presentations. However, one skilled in the art will appreciate that the methods and formula disclosed can be adapted within the scope of what is pharmaceutically acceptable to provide a range of viscosities that permit the manufacture of liquid formulations for the dosing of PPI suspensions that can be adapted to further refine and optimize the balance of viscosity and suspendability. This balance allows the customization of formulations to allow increased use of suspending agents to increase time-in-suspension, and thus sustaining homogeneity of the preparation over the intended use life.

By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

Compounding Kits

The invention also encompasses and contemplates compounding kits used to prepare the formulations, including but not limited to, approved drug formulations for reconstitution. The Omeprazole Powder for Oral Suspension Kit (e.g., 2 mg/ml) disclosed herein primarily comprises of two components:
a) the active pharmaceutical ingredient (API) powder component in a container (e.g., a high density polyethylene (HDPE) container); and
b) a diluent in a container (e.g., a HDPE container).

In some embodiments, the volume of diluent is about 90 mL, about 150 mL or about 300 mL. In some embodiments, the amount of API is about 0.18 g, about 0.3 g, or about 0.6 g.

In alternative embodiments, a suspension kit of the present disclosure comprises the API and the diluent in the same container (e.g., an HDPE container). In another alternative embodiment, a suspension kit of the present disclosure comprises the described diluent and instructions for using the diluent.

The kits described herein allow for long term storage of the diluent and API powder, so that they can be used to make reconstituted suspensions as needed. Additionally, the kits described herein allow for flexible dosing. In some embodiments, the omeprazole concentration in the reconstituted suspension is about 2 mg/ml. In some embodiments, the omeprazole concentration in the reconstituted suspension is about 1 mg/ml. In some embodiments, the omeprazole concentration in the reconstituted suspension is from about 1 mg/ml to about 2 mg/ml.

A compounding kit can be designed to produce a desired amount of liquid suspension. For example, the kit can be designed to produce about 90 ml, about 150 ml, or about 300 ml liquid suspension with 2 mg/ml omeprazole concentration. In some embodiments, the kit comprises about 0.6 g omeprazole powder. In some embodiments, the kit comprises about 0.3 g omeprazole powder. In some embodiments, the kit comprises about 0.18 g omeprazole powder. In some embodiments, the kit comprises from about 0.1 g to about 1 g omeprazole powder. In some embodiments, the kit comprises about 300 ml liquid diluent. In some embodiments, the kit comprises about 150 ml liquid diluent. In some embodiments, the kit comprises about 90 ml liquid diluent. In some embodiments, the kit comprises about from 50 ml to about 500 ml liquid diluent.

A major advantage of the invention is the flexibility of dose that can be prescribed by the physician. The ability to reconstitute a supply of PPI in a liquid formulation to be dosed orally to a patient later in the day, over the course of several days, over the course of a week, or over the course of several weeks, provides ease of use to the compounding pharmacist, physician, and patient. This provides a time saving and cost effective method of producing multiple drug doses in the pharmacy for a single patient. In addition, as the method described utilized bulk API rather than recycling final dosage forms of licensed drug products (i.e. recovering granules of drug from drug capsules), the invention provides additional consistency over alternative compounding formulation methods. In some embodiments, the formulations described and the preparation methods disclosed have been shown to produce comparably stable and homogenous liquid formulations from more than one source of bulk API, demonstrating the broad applicability of the methods disclosed.

The ability to deliver a single container of liquid drug to the patient provided by the present invention also solves several problems posed by existing dose formats to patients. In addition, the ability to reliably deliver the dose in patients who cannot swallow capsules or who have difficulty doing so, the present invention also avoids the complexity to the patient of having to reconstitute and then immediately drink the only available PPI that is provided for liquid formulation. This provides additional benefit to the patient in terms of increased compliance and reduction in errors in reconstitution.

The package may be compartmentalized to receive one or more bottles and the like, each of the container(s) comprising of one of the separate elements to be used in a method described herein including an API powder or solution component. The suitable containers can be formed from a variety of materials including plastic materials (e.g., HDPE).

A kit will typically be comprised of one or more additional containers, each one with one or more of various materials (such as API powder and solution component containing inactive ingredients) desirable from a commercial and user standpoint for an API powder or solution component herein. Non-limiting examples of such materials include, but are not limited to, buffers, diluents, tools; carrier, package, container, and/or bottle labels listing contents, and package inserts with a set of instructions for compounding are included.

A label can be on or associated with the container. A label can be on a container when letters, numbers, or characters forming the label are attached or stamped onto the container itself; a label can be associated with a container when it is present within a receptacle or carrier that also holds the container, e.g., as a package insert. In some embodiments, the kit also includes instructions for use, either included within or on the package.

Methods of Treatment

The liquid formulations (e.g., suspensions) of the present disclosure can be used for the treatment of a subject or, more specifically, the treatment of a subject having a gastrointestinal disorder. In some embodiments, the method for treating a subject can comprise administering to said subject a therapeutically effective amount of the PPI (e.g., omeprazole, esomeprazole, lansoprazole, rabeprazole, pantoprazole, and dexlansoprazole) suspension, as disclosed herein.

As used herein, the term "therapeutic" means an agent utilized to treat, combat, ameliorate, prevent or improve an unwanted condition or disease of a patient. In some embodiments, a therapeutic agent is directed to the reduction of the production of gastric acid, and in certain embodiments the therapeutic is a proton pump inhibitor, and in specific embodiments the proton pump inhibitor is omeprazole or lansoprazole. In certain embodiments, the proton pump inhibitor is omeprazole. In certain embodiments, the proton pump inhibitor is esomeprazole. In certain embodiments, the proton pump inhibitor is lansoprazole. In certain embodiments, the proton pump inhibitor is rabeprazole. In certain embodiments, the proton pump inhibitor is pantoprazole. In certain embodiments, the proton pump inhibitor is dexlansoprazole. In certain embodiments the therapeutic can be used in the treatment of one or more conditions including dyspepsia, peptic ulcer disease, duodenal ulcer, gastric ulcer, *Helicobacter pylori*, gastroesophageal reflux disease, laryngopharyngeal reflux causing laryngitis, Barrett's esophagus, erosive esophagitis, eosinophilic esophagitis and stress gastritis. In other embodiments the therapeutic could be used for prevention of ulcer and/or upper gastrointestinal tract bleeding for critical care patients. In other embodiments, the therapeutic could be used to treat conditions that cause hypersecretion of stomach acid such as Zollinger-Ellison syndrome or gastrinomas.

Accordingly, in one aspect, described herein are methods of treating one or more conditions or disorders. In certain embodiments, the condition or disorder is duodenal ulcer. In certain embodiments, the condition or disorder is *Helicobacter pylori* infection. In certain embodiments, the condition or disorder is gastric ulcer. In certain embodiments, the condition or disorder is GERD. In certain embodiments, the condition or disorder is erosive esophagitis. In certain embodiments, the condition or disorder is dyspepsia. In certain embodiments, the condition or disorder is peptic ulcer disease. In certain embodiments, the condition or disorder is laryngopharyngeal reflux causing laryngitis. In certain embodiments, the condition or disorder is Barrett's esophagus. In certain embodiments, the condition or disorder is eosinophilic esophagitis. In certain embodiments, the condition or disorder is stress gastritis.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology). As such, a non-limiting example of a "therapeutically effective amount" or "effective amount" of a composition of the present disclosure may be used to inhibit, block, or reverse the activation of gastric acid secretion. The therapeutically effective amount depends on factors such the particular PPI, disease condition and severity, and the identity (age, weight, sex, etc.) of the subject in need of treatment.

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is a child. In certain instances, the human is elderly. Other examples of subjects include experimental animals such as mice, rats, dogs, cats, goats, sheep, pigs, and cows.

In one aspect, the method comprises using the described compounding kit. In some embodiments, the method comprises combining the PPI power with the diluent. In some embodiments, the method comprises combining and mixing the PPI power with the diluent.

Other Definitions

As used herein, "titrimetric methods" refer to methods for determining the number of moles of reagent required to react quantitatively with the substance being determined. General titrimetric methods involve the addition of a reagent (referred to as the titrant) to a solution containing another reagent (referred to as the titrand), allowing a reaction.

As used herein "DSC methods" refer to differential scanning calorimetry (DSC), which is a thermo-analytical technique in which the difference in the amount of heat required to increase the temperature of a sample and reference is measured as a function of temperature.

As used herein, the term "liquid formulation" may refer to the diluent composition. In some embodiments, the term "liquid formulation" may refer to the reconstituted suspension of API with the diluent.

As used herein, the term "drug specification" refers to the test procedures and acceptance criteria for a drug (e.g., new drug substance or product) as defined by the United States Food and Drug Administration or the United States Pharmacopeia. As used herein, the terms "drug specification" and "specification" are used interchangeably.

The term "consisting essentially of" is contextual as it relates to the properties of the composition. For instance, if a composition consists essentially of a suspension or solution that is homogenous and stable for at least 30 days (or any other stability time contemplated herein) at ambient conditions and/or at refrigerated temperature conditions, a different composition or the addition of components which negatively affects this limitation would not fall within the scope of the composition. In some instances, if a composition consists essentially of a suspension or solution that has stability (e.g., long-term stability), homogeneity, and/or freeze-thaw stability, then a different composition or the addition of components which negatively affects this limitation would not fall within the scope of the composition. For example, if a liquid diluent or reconstituted suspension, as contemplated herein, consists essentially of omeprazole, poloxamer (e.g., poloxamer 188), sodium CMC, sodium bicarbonate, sodium citrate, simethicone emulsion, benzyl alcohol, a sweetener, and water (e.g., purified water), wherein the liquid diluent or suspension is stable for at least 30 days, then the addition of a flavoring agent (for example) falls within the scope of the composition, provided it does not change the stability property.

"Optional" or "optionally" may be taken to mean that the subsequently described structure, event or circumstance may or may not occur, and that the description includes instances where the events occurs and instances where it does not.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. For example, "about" can refer to within 1 or more than 1 standard deviation, per the practice in the art. Alternatively, "about" can refer to a range of up to 20%, up to 10%, up to 5%, or up to 1% of a given value. The use of the term "or" in the claims is used to refer to "and/or" unless explicitly indicated to refer to alternatives only or the alternatives are mutually exclusive, although the disclosure supports a definition that refers to only alternatives and to "and/or". The terms "comprise", "have", and "include" are open-ended linking verbs. Any forms or tenses of one or more of these verbs "comprises," "comprising," "has," "having," "includes," and "including" are also open-ended. For example, any method that "comprises," "has" or "includes" one or more steps is not limited to possessing only those one or more steps and also covers other unlisted steps.

As used herein, a weight/volume percentage (% w/v) is calculated based on g of solute/100 ml of solution.

Unless defined otherwise, all technical and scientific terms used herein have the same meanings as commonly understood by one skilled in the art. Although any methods and materials similar or equivalent to those described herein can be used in the practice of testing of embodiments described herein, certain preferred methods, devices, and materials are now described.

Various aspects of the embodiments described above may be used alone, in combination, or in a variety of arrangements not specifically discussed in the embodiments described in the foregoing, and is therefore not limited in its application to the details and arrangement of components set forth in the foregoing description or illustrated in the drawings. For example, aspects described in one embodiment may be combined in any manner with aspects described in other embodiments.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Screening of surfactants was performed to identify an ideal surfactant and corresponding surfactant concentration for use in the diluent and reconstituted suspension. Subsequently, screening of polymer/viscosity building agent was performed to identify an ideal polymer(s) and corresponding polymer concentration for use in the diluent and reconstituted suspension. After identifying the surfactant and polymers/viscosity building agents, four different prototypes (diluents) were developed, characterized, and evaluated for stability. The four diluents were prepared using either sodium CMC (the product sodium carboxymethylcellulose sold under the trademark CEKOL® 700P) or sodium CMC/ microcrystalline cellulose (Avicel CL-611) as the polymer/ viscosity building agent. Additionally, two previously developed prototypes (previous formulations that exhibited gel formation—Diluent Formula 0093A-8 and Diluent Formula 0093A-22) were characterized and evaluated for comparison purposes. These two diluents were prepared by using hydroxyethyl cellulose (Natrasol 250 HHX).

The objective of using different polymers/viscosity building agents was to evaluate their impact on the omeprazole suspension's physical and chemical characteristics. Poloxamer 188 content was also varied in the above-mentioned formulation from 0% w/v to 4% w/v to evaluate the wettability of omeprazole and hence uniform dispersibility of the omeprazole active pharmaceutical ingredient (API) in the reconstituted suspension. Two different strategies were evaluated in the diluent reformulation. In the first strategy, API was added to one high-density polyethylene (HDPE) container and the diluent was added to another, while in the second strategy, a physical mixture of API and sodium bicarbonate was prepared and added to one HDPE container and the diluent (without sodium bicarbonate) was added to another. The $2^{nd}$ strategy was studied to evaluate the dispersibility of the API during reconstitution. The physical mixture of sodium bicarbonate with the API may inhibit formation of aggregates during storage.

During the stability studies for all 6 prototypes, the prototype comprising Avicel CL-611 with poloxamer 188 showed slow release at initial dissolution time points and incomplete release at terminal time points. During physical observation, the prototype comprising sodium CMC without poloxamer 188 showed omeprazole particles floating on the surface of the reconstituted suspension because of the wettability issues of the API. The prototype containing a physical mixture of API and sodium bicarbonate showed higher impurity content compared to other prototypes, and during physical observation, omeprazole particles were observed floating on the surface of the reconstituted suspension because of the wettability issue of the API. For both Diluent Formula 0093A-8 and Diluent Formula 0093A-22, a gel-formation tendency was observed in freeze-thaw studies. It was expected that a higher poloxamer content may have an impact on the pharmacokinetics of omeprazole.

A formulation containing sodium CMC with poloxamer 188 was identified as the preferred formulation for the diluent and reconstituted suspension.

Example 1: Selection of Surfactant and Suspending Agents for Diluent Reformulation 1.0 Formulation Development (Diluent Reformulation)

For the diluent reformulation studies the excipients which play a critical role were identified and evaluated. Surfactant and suspending agents were the two most critical excipient categories which were evaluated.

1.1 Surfactant Selection

The following three surfactants/wetting agents were screened for their ability to provide wettability of the API:
a. Poloxamer 188 (Kolliphor P 188)
b. Sodium Lauryl Sulfate (Kolliphor SLS fine)
c. Polysorbate 80 (Tween 80)

The three agents, poloxamer 188, sodium lauryl sulfate, and polysorbate 80, were evaluated at concentrations of 2% w/v, 0.1% w/v, and 0.1% w/v respectively. A control formulation without surfactant/wetting agent was also evaluated. Sodium bicarbonate was included in each formulation at a concentration of 8.4% w/v, as the concentration of sodium bicarbonate plays an important role in acid neutralizing capacity and protects omeprazole API from acidic degradation.

Four test formulations were prepared to evaluate the wetting property of the surfactants/wetting agents on the omeprazole API. The four test formulations were prepared and omeprazole API was added to evaluate the wetting property (See Table 2).

TABLE 2

Details on the surfactant selection:

| | Test 1 Control (No Surfactant) | Test 2 Poloxamer 188 (2% w/v) | Test 3 Sodium Lauryl Sulfate (0.1% w/v) | Test 4 Polysorbate 80 (0.1% w/v) |
|---|---|---|---|---|
| Omeprazole (g) | 0.4 | 0.4 | 0.4 | 0.4 |
| Sodium bicarbonate (Granular No. 5) (g) | 16.8 | 16.8 | 16.8 | 16.8 |
| Poloxamer 188 (Kolliphor P 188) (g) | NA | 4.0 | NA | NA |
| Sodium lauryl sulfate (Kolliphor SLS fine) (g) | NA | NA | 0.2 | NA |
| Polysorbate 80 (Tween 80) (g) | NA | NA | NA | 0.2 |
| Purified water | q.s. to 200 ml | q.s. to 200 ml | q.s. to 200 ml | q.s. to 200 ml |

Observations:

Test 1: After addition of omeprazole API to the Test 1 formulation (see Table 2), it was observed that omeprazole completely floats on the surface. It was concluded that addition of a wetting agent would be required for wettability of omeprazole API.

Test 2: After addition of omeprazole API to the Test 2 formulation (see Table 2), it was observed that omeprazole API gets dispersed in the media with very few particles floating on the surface.

Test 3: After addition of omeprazole API to the Test 3 formulation (see Table 2), it was observed that very few particles of omeprazole API get dispersed in the media and most of the omeprazole API is floating on the surface.

Test 4: After addition of omeprazole API to the Test 4 formulation (see Table 2), it was observed that very few particles of omeprazole API get dispersed in the media and most of the omeprazole API is floating on the surface.

Conclusion:

Based on the wettability observations, poloxamer 188 was found to be better compared to other surfactants with respect to wetting the omeprazole API and allowing it to disperse in the formulation. Higher concentrations of polysorbate 80 and sodium lauryl sulfate were not evaluated, as higher concentrations may have an impact on the bioavailability of omeprazole and polysorbate 80 is prone to oxidation.

1.2 Surfactant Concentration Optimization

Different concentrations of poloxamer 188 were evaluated to assess the impact of concentration on wettability of the omeprazole API. The diluents were prepared then omeprazole API was added to evaluate the wetting property. The content of sodium bicarbonate was maintained as before. The following four concentrations of poloxamer 188 were evaluated:

Test 1—Formulation with 0.5% w/v poloxamer 188
Test 2—Formulation with 1.0% w/v poloxamer 188
Test 3—Formulation with 2.0% w/v poloxamer 188
Test 4—Formulation with 4.0% w/v poloxamer 188

TABLE 3

Details on the surfactant concentration optimization

| | Test 1 Poloxamer 188 (0.5% w/v) | Test 2 Poloxamer 188 (1% w/v) | Test 3 Poloxamer 188 (2% w/v) | Test 4 Poloxamer 188 (4% w/v) |
|---|---|---|---|---|
| Omeprazole (g) | 0.4 | 0.4 | 0.4 | 0.4 |
| Sodium Bicarbonate (Granular No. 5) (g) | 16.8 | 16.8 | 16.8 | 16.8 |
| Poloxamer 188 (Kolliphor P 188) (g) | 1.0 | 2.0 | 4.0 | 8.0 |
| Purified water | q.s. to 200 ml | q.s to 200 ml | q.s. to 200 ml | q.s. to 200 ml |

Observations:

Test 1: After addition of omeprazole API in the Test 1 formulation (see Table 3), it was observed that about 70% of the omeprazole API was dispersed in the media, and about 30% of the omeprazole was floating on the surface.

Test 2: After addition of omeprazole API in the Test 2 formulation (see Table 3), it was visually observed that the majority of omeprazole API gets dispersed in the media and very few particles were floating on the surface. In some embodiments at least about 90% of omeprazole API gets dispersed in the media.

Test 3: After addition of omeprazole API in the Test 3 formulation (see Table 3), it was visually observed that the majority of omeprazole API gets dispersed in the media and very few particles were floating on the surface. In some embodiments at least about 90% of omeprazole API gets dispersed in the media.

Test 4: After addition of omeprazole API in the Test 4 formulation (see Table 3), it was observed that omeprazole API gets fully dispersed in the media and no particles were floating on the surface.

Conclusion:

Based on the wettability observations, it was concluded that a poloxamer 188 concentration of 1% w/v showed good wettability of the omeprazole API. Compared to 1% w/v poloxamer 188, no significant advantage in wettability was observed at poloxamer 188 concentrations higher than 1% w/v. Higher concentrations of poloxamer may have an impact on the bioavailability of the formulation hence 1% w/v poloxamer was selected for further studies.

1.3 Suspending Agent Selection

Different suspending agents/viscosity building agents were screened for their ability to provide suspendability of omeprazole API and prevent caking at the bottom of the container. The following suspending agents mentioned below were screened:

Test 1—Sodium CMC
Test 2—Xanthan gum
Test 3—Hydroxyethyl cellulose (HEC)
Test 4—Hydroxypropyl methylcellulose (HPMC)
Test 5—Avicel CL-611

Based on the theoretical viscosity data, sodium CMC, xanthan gum, Hydroxyethyl cellulose (HEC), Hydroxypropyl methylcellulose (HPMC), and Avicel CL-611 were used at concentration of 1.2% w/v, 0.4% w/v, 0.4% w/v, 0.8% w/v, and 4.0% w/v respectively.

Five test formulations were prepared to evaluate the effect of the suspending agents/viscosity building agents on the suspendability of omeprazole API (see Table 4). The formulations were prepared and observations were made just after preparation and again the following day.

TABLE 4

Details on the suspending agent selection

| | Test 1 Sodium CMC (1.2% w/v) | Test 2 Xanthan gum (0.4% w/v) | Test 3 Hydroxyethyl cellulose (0.4% w/v) | Test 4 Hydroxypropyl methylcellulose (0.8% w/v) | Test 5 Avicel CL-611 (4.0% w/v) |
|---|---|---|---|---|---|
| Omeprazole (g) | 0.4 | 0.4 | 0.4 | 0.4 | 0.4 |
| Sodium bicarbonate (Granular No. 5) (g) | 16.8 | 16.8 | 16.8 | 16.8 | 16.8 |
| Poloxamer 188 (Kolliphor P 188) (g) | 2.0 | 2.0 | 2.0 | 2.0 | 2.0 |
| Sodium CMC (Cekol 700P) (g) | 2.4 | NA | NA | NA | NA |
| Xanthan gum (g) | NA | 0.8 | NA | NA | NA |
| Hydroxyethyl cellulose (Natrasol 250 HHX) (g) | NA | NA | 0.8 | NA | NA |
| Hydroxypropyl Methylcellulose (Metolose 60SH-4000) (g) | NA | NA | NA | 1.6 | NA |
| Avicel CL-611 (g) | NA | NA | NA | NA | 8.0 |
| Purified water | q.s. to 200 ml | q.s. to 200 ml | q.s. to 200 ml | q.s. to 200 ml | q.s. to 200 ml |

Observations:

Test 1: The suspension formed was uniform with a few particles settled at the bottom.
Observation upon standing (Next Day): A few API particles were settled at the bottom upon standing and were easily redispersible upon shaking. The suspension exhibited less caking and was more redispersable compared to the HEC formulation (Test 3) and the HPMC formulation (Test 4).

Test 2: The suspension formed was uniform with very few particles settled at the bottom.
Observation upon standing (Next Day): Very few large API particles were settled at the bottom upon standing and were easily redispersible upon shaking. The suspension exhibited less caking and was more redispersable compared to the HEC formulation (Test 3) and the HPMC formulation (Test 4).

Test 3: The API particles settled at the bottom within a few minutes.
Observation upon standing (Next Day): Caking of API particles was observed at the bottom and was redispersible upon shaking. The suspension exhibited less caking and was more redispersable compared to the HPMC formulation (Test 4).

Test 4: The API particles settled at the bottom within a few minutes.
Observation upon standing (Next Day): Caking of API particles (complete settling) was observed at the bottom and was redispersible upon shaking Test 5: Very few large API particles settled at the bottom, however uniformity of suspension could not be observed due to the opaque nature of the Avicel CL-611 suspension (Test 5).
Observation upon standing (Next Day): Few particles settled at the bottom, however uniformity of suspension could not be observed due to the opaque nature of the Avicel CL-611 suspension (Test 5).

Conclusion:

Based on the suspendability observations, it was concluded that among the above-mentioned suspending agents, Sodium CMC, Avicel CL 611 and Xanthan gum were found to be better compared to other suspending agents. Xanthan gum was not evaluated further due to the risk of gel formation tendency observed in previous diluents (e.g. Diluent Formula 0093A-8 and Diluent Formula 0093A-22).

1.4 Suspending Agent Concentration Optimization

Sodium CMC and Avicel CL 611 at different concentration were evaluated to check the impact of concentration on suspendability of Omeprazole API. The 4 formulations listed below were prepared (see Table 5), and observations were made just after preparation and again the following day.

Test 1—Formulation with 1.2% w/v Sodium CMC
Test 2—Formulation with 2.0% w/v Sodium CMC
Test 3—Formulation with 4.0% w/v Avicel CL 611
Test 4—Formulation with 2.0% w/v Avicel CL 611

TABLE 5

Details of suspending agent concentration optimization

| | Test Formulation No | | | |
|---|---|---|---|---|
| | OME-20-F-086 Test 1 (g) Sodium CMC (1.2%) | OME-20-F-087 Test 2 (g) Sodium CMC (2.0%) | OME-20-F-086 Test 3 (g) Avicel CL 611 (4.0%) | OME-20-F-087 Test 4 (g) Avicel CL 611 (2.0%) |
| Omeprazole | 0.4 | 0.4 | 0.4 | 0.4 |
| Sodium Bicarbonate (Granular No. 5) | 16.8 | 16.8 | 16.8 | 16.8 |
| Poloxamer 188 (Kolliphor P 188) | 2.0 | 2.0 | 2.0 | 2.0 |
| Sodium CMC (Cekol 700P) | 2.4 | 4.0 | NA | NA |
| Avicel CL 611 | NA | NA | 8.0 | 4.0 |
| Purified water | q.s to 200 ml | q.s to 200 ml | q.s to 200 ml | q.s to 200 ml |

Observations:

Test 1: The suspension formed was uniform with few particles settled at the bottom.
> Observation upon standing (Next Day): A few API particles were settled at the bottom upon standing and were easily redispersible upon shaking Test 2: The suspension formed was uniform with very few particles settled at the bottom. However, visually the viscosity was found to be higher and the suspension was not easily pourable when compared to the formulation with 1.2% w/v sodium CMC (Test 1).
> Observation upon standing (Next Day): A few API particles were settled at the bottom upon standing. However, visually, the viscosity was found to be higher and the suspension was not easily pourable when compared to the formulation with 1.2% w/v sodium CMC (Test 1).

Test 3: Very few large API particles settled at the bottom, however uniformity of suspension could not be observed due to the opaque nature of the 4% w/v Avicel CL-166 suspension (Test 3).
> Observation upon standing (Next Day): Few particles settled at the bottom, however uniformity of suspension could not be observed due to the opaque nature of the 4% w/v Avicel CL-611 suspension (Test 3).

Test 4: More API particles settled at the bottom than in the 4% Avicel CL-611 suspension (Test 3) due to the lower viscosity of the 2% w/v Avicel CL-166 suspension (Test 4), however uniformity of suspension could not be observed due to the opaque nature of the 2% w/v Avicel CL-611 suspension (Test 4).
> Observation upon standing (Next Day): More API particles were settled at the bottom due to the lower viscosity of this formulation when compared to the formulation with 4% w/v Avicel CL-611, however uniformity of suspension could not be observed due to the opaque nature of the 2% w/v Avicel CL-611 suspension (Test 4).

Conclusion:

Based on the suspendability observations it was concluded that formulations with 1.2% w/v sodium CMC and 4.0% w/v Avicel CL-611 showed better suspendability and pourability. Hence both of these formulations were further evaluated in stability studies.

Based upon the evaluation, 4 prototype formulations were manufactured with usage of sodium CMC and Avicel CL-611 as suspending agents/viscosity building agents. The concentrations of sodium bicarbonate (acid neutralizer), simethicone emulsion (anti-foaming agent), Strawberry Flavor CW08 (flavoring agent), sorbitol solution (sweetener), sodium citrate (palatability enhancer), sucralose (sweetener), FD&C Red No. 40 (coloring agent), benzyl alcohol (preservative) were kept constant. These four prototype formulations and the two previously developed prototype formulations (Diluent Formula 0093A-8 and Diluent Formula 0093A-22) were characterized and evaluated for stability over time.

Example 2: Evaluation of Six Potential Prototype Formulations 2.0 Diluent Formulation Details Below are the 6 prototype formulations (diluents; as described in Example 1) that were characterized and tested for stability herein. The formulations for these prototypes are provided in Table 6.

1. Sodium CMC+1.0% w/v poloxamer 188
2. Avicel CL-611+1.0% w/v poloxamer 188
3. Sodium CMC without w/v poloxamer 188
4. Sodium CMC without poloxamer 188 and sodium bicarbonate in physical mixture with API
5. Diluent Formula: 0093A-8 (4% w/v poloxamer 188)
6. Diluent Formula: 0093A-22 (2% w/v poloxamer 188)

2.1 Diluent Formula Composition and Procedure

TABLE 6

Diluent Formula Composition of the 6 prototype formulations

| Ingredient | Sodium CMC with poloxamer 188 % w/v | Avicel CL-611 with poloxamer 188 % w/v | Sodium CMC without poloxamer 188 % w/v | Sodium CMC without poloxamer 188 & sodium bicarbonate in physical mixture % w/v | Diluent Formula 0093A-8 % w/v | Diluent Formula 0093A-22 % w/v |
|---|---|---|---|---|---|---|
| Poloxamer 188 (Kolliphor P188) | 1 | 1 | NA | NA | 4 | 2 |
| Sodium CMC (Cekol 700P) | 1.2 | NA | 1.2 | 1.2 | NA | NA |
| Microcrystalline Cellulose (Avicel CL-611) | NA | 4 | NA | NA | NA | NA |
| Hydroxyethyl cellulose (Natrasol 250 HHX) | NA | NA | NA | NA | 0.35 | 0.35 |
| Sodium bicarbonate | 8.4 | 8.4 | 8.4 | NA | 8.4 | 8.4 |
| Simethicone emulsion | 0.15 | 0.15 | 0.15 | 0.15 | 0.15 | 0.15 |
| Strawberry Flavor CW08 | 0.15 | 0.15 | 0.15 | 0.15 | 0.15 | 0.15 |
| 70% sorbitol solution | 2.5 | 2.5 | 2.5 | 2.5 | 2.5 | 2.5 |
| Sodium Citrate | 1 | 1 | 1 | 1 | 1 | 1 |
| Sucralose | 0.4 | 0.4 | 0.4 | 0.4 | 0.4 | 0.4 |

TABLE 6-continued

Diluent Formula Composition of the 6 prototype formulations

| Ingredient | Sodium CMC with poloxamer 188 % w/v | Avicel CL-611 with poloxamer 188 % w/v | Sodium CMC without poloxamer 188 % w/v | Sodium CMC without poloxamer 188 & sodium bicarbonate in physical mixture % w/v | Diluent Formula 0093A-8 % w/v | Diluent Formula 0093A-22 % w/v |
|---|---|---|---|---|---|---|
| FD&C Red No. 40 | 0.003 | 0.003 | 0.003 | 0.003 | 0.003 | 0.003 |
| Benzyl Alcohol | 0.5 | 0.5 | 0.5 | 0.5 | 0.5 | 0.5 |
| Glycerin 99.7% | NA | NA | NA | NA | 10 | 10 |
| Water | q.s | q.s | q.s | q.s | q.s | q.s |

TABLE 7

The composition of Diluent Formula 0093A-22 and functions of ingredients

| Ingredient | Function | % w/v |
|---|---|---|
| Poloxamer 188 (Kolliphor P188) | Surfactant | 1 |
| Hydroxyethyl cellulose (Natrasol 250 HHX) | Viscosity building/suspending agent | 0.35 |
| Sodium bicarbonate | Acid neutralizing agent | 8.4 |
| Simethicone emulsion | Defoamer | 0.15 |
| Strawberry Flavor CW08 | Flavoring agent | 0.15 |
| 70% sorbitol solution | Sweetener | 2.5 |
| Sodium citrate | Palatability enhancer/buffer | 1 |
| Sucralose | Sweetener | 0.4 |
| FD&C Red No. 40 | Coloring agent | 0.003 |
| Benzyl alcohol | Preservative | 0.5 |
| Glycerin 99.7% | Co-Solvent | 10 |
| Water | Solvent | q.s. |

Procedure for Diluent Preparation:
1. Place water in a stainless steel vessel and stir it continuously.
2. Add the polymer/viscosity building agent (sodium CMC or Avicel CL-611*) to step 1 and stir it continuously until a clear solution is obtained, then add poloxamer 188 (Kolliphor P188), (if applicable).
3. After a clear solution is obtained, add simethicone emulsion to prevent foaming, then add sodium bicarbonate (if applicable), Strawberry Flavor CW08, 70% sorbitol solution, sodium citrate, sucralose, FD&C Red No. 40 and benzyl alcohol.
4. After adding all the excipients, stir until a clear solution is obtained.
5. Make up to the final volume with water.

* For the formulation of Avicel CL-611 with poloxamer 188, poloxamer 188 is added prior to Avicel CL-611. Avicel CL-611 will remain dispersed as it is insoluble.

2.2 Storage Conditions and Testing Frequency for Stability Studies

The 6 diluents and API were staged for development stability studies.

| Storage conditions | Testing Frequency (Months) |
|---|---|
| 25 ± 2° C. & 60 ± 5% RH | 1, 2, 3 and 6 |
| 5 ± 3° C. | 0, 3 and 6 |

During the development stability studies, samples of each diluent and API were removed at each time point and reconstitution was performed. Each reconstituted suspension was then stored at 2-8° C. and analyzed at four different time points i.e., Initial, Day 7, Day 15 and Day 30 (In-use stability). Note: herein, 1M, 2M, 3M, and 6M represent 1 month, 2 months, 3 months, and 6 months of storage at the original condition, respectively, and Day 7 (D7), Day 15 (D15), and Day 30 (D30) are the subsequent days of storage after reconstitution. The reconstituted suspensions were evaluated at each testing point by visual observation, analysis of omeprazole, omeprazole impurities (related substances), and dissolution.

2.3 Selection of the Most Promising Prototype Formulations

Out of the 6 formulations, 2 formulations (sodium CMC with 1% w/v poloxamer 188 and HEC with 2% w/v poloxamer 188) looked promising. Observations are summarized in the table below:

| Formulation | Composition | Observation |
|---|---|---|
| Formulation 1 | Sodium CMC with poloxamer 188 | Looks promising |
| Formulation 2 | Avicel CL-611 with poloxamer 188 | Dissolution: Observed slow dissolution at initial time points and incomplete release at the terminal time point. |
| Formulation 3 | Sodium CMC without poloxamer 188 | Physical Description: Observed omeprazole particles floating on the surface of the reconstituted suspension. However, afters haking particles were dispersed uniformly. Since particles were observed after reconstitution, it may indicate that this formulation is problematic with respect to uniformity. |
| Formulation 4 | Sodium CMC without poloxamer 188 & sodium bicarbonate in physical mixture | Physical Description: Observed omeprazole particles floating on the surface of reconstituted suspension. However, after shaking, particles were dispersed uniformly. Since particles were observed after reconstitution, it may indicate that this formulation is problematic with respect to uniformity. Related Substance: Observed impurity levels were greater when compared to other formulations. |
| Formulation 5 | Diluent Formula: 0093A-8 | Gel Formation: Gel formation observed during freeze-thaw studies. Assay: Variability was observed with respect to assay data, this may have been because of poor content uniformity. Dissolution: Variability is observed with respect to dissolution data, this may be because of poor content uniformity. Pharmacokinetics: The higher amount of poloxamer 188 (4% w/v) was believed to have a significant impact on bio-availability prior to the studies shown herein. |

-continued

| Formulation | Composition | Observation |
|---|---|---|
| Formulation 6 | Diluent Formula: 0093A-22 | Looks promising |

Physico-chemical characterization and stability data (1M, Day 30 to 6M, Day 30) of two promising formulations are summarized in below sections:
1. Sodium CMC+1.0% w/v poloxamer 188
2. HEC+2% w/v poloxamer 188 (Formula: 0093A-22)
Note: Stability data is summarized from 1M Day 30 (25±2° C. & 60±5% RH) onwards, as was performed from 1M, Day 30.

Example 3: Characterization of Two Lead Prototype Formulations 3.1 Diluent Formula: Sodium CMC with 1% w/v Poloxamer 188

For the manufacturing of stability batches, the excipients used along with their function and an assigned test number are mentioned in the below table:

| Ingredient | Function | % w/v |
|---|---|---|
| Poloxamer 188 (Kolliphor P188) | Surfactant | 1 |
| Sodium CMC (Cekol 700P) | Viscosity building/suspending agent | 1.2 |
| Sodium bicarbonate | Acid neutralizing agent | 8.4 |
| Simethicone emulsion | Defoamer | 0.15 |
| Strawberry Flavor CW08 | Flavoring agent | 0.15 |
| 70% sorbitol solution | Sweetener | 2.5 |
| Sodium citrate | Palatability enhancer/buffer | 1 |
| Sucralose | Sweetener | 0.4 |
| FD&C Red No. 40 | Coloring agent | 0.003 |
| Benzyl alcohol | Preservative | 0.5 |
| Water | Solvent | q.s. |

3.2 Description

For the two lead reconstituted suspensions, samples were physically observed at each stability time point. Data is summarized in the table below.

Specification: Pink to red hazy liquid.

A) Comparison of Sodium CMC+1.0% w/v poloxamer 188 reconstituted suspension at different stability time points:

| In-Use Time points | Description |
|---|---|
| 1M, D30 | Homogeneous suspension with full pink color. Free flowing suspension. No Particles observed. |
| 2M, D0 | Homogeneous suspension with full pink color. Free flowing suspension. Small amount of white colored Particles observed. |
| 2M, D7 | Homogeneous suspension with pink color. Free flowing suspension. Small amount of white colored particles observed. |
| 2M, D15 | Homogeneous suspension with pink color. Free flowing suspension. Small amount of white colored particles observed. |
| 2M, D30 | Homogeneous suspension with full pink color. Free flowing suspension. No Particles observed. |
| 3M, D0 25/60 | Homogeneous suspension with full pink color. Free flowing suspension. No Particles observed. |
| 3M, D0 2-8 | Homogeneous suspension with pink color. Free flowing suspension. Very small amount of white colored particles observed at bottom of the beaker. |
| 3M, D7 25/60 | Homogeneous suspension with full pink color. Free flowing suspension. No Particles observed. |
| 3M, D7 2-8 | Homogeneous suspension with pink color. Free flowing suspension. Small amount of white colored particles observed at bottom of the beaker. |
| 3M, D15 25/60 | Homogeneous suspension with full pink color. Free flowing suspension. No Particles observed. |
| 3M, D15 2-8 | Homogeneous suspension with pink color. Free flowing suspension. Small amount of white colored particles observed at bottom of the beaker. |
| 3M, D30 25/60 | Homogeneous suspension with full pink color. Free flowing suspension. No Particles observed. |
| 3M, D30 2-8 | Homogeneous suspension with pink color. Free flowing suspension. Small amount of white colored particles observed at bottom of the beaker. |
| 6M, D0 25/60 | Homogeneous suspension with pink color. Free flowing suspension. Large white colored particles observed when seen from the bottom of the glass beaker. |
| 6M, D0 2-8 | Homogeneous suspension with pink color. Free flowing. Small amount of white colored particles observed when seen from the bottom of the glass beaker. |
| 6M, D7 25/60 | Homogeneous suspension with pink color. Free flowing suspension. Large white colored particles observed when seen from the bottom of the glass beaker. |
| 6M, D7 2-8 | Homogeneous suspension with pink color. Free flowing. Small amount of white colored particles observed when seen from the bottom of the glass beaker. |
| 6M, D15 25/60 | Homogeneous suspension with pink color. Free flowing suspension. Large white colored particles observed when seen from the bottom of the glass beaker. |
| 6M, D15 2-8 | Homogeneous suspension with pink color. Free flowing. Small amount of white colored particles observed when seen from the bottom of the glass beaker. |

-continued

| In-Use Time points | Description |
| --- | --- |
| 6M, D30 25/60 | Homogeneous suspension with pink color. Free flowing suspension. Large white colored particles observed when seen from the bottom of the glass beaker. |
| 6M, D30 2-8 | Homogeneous suspension with pink color. Free flowing. Small amount of white colored particles observed when seen from the bottom of the glass beaker. |

Note:
25/60 stands for 25° C./60% RH and 2-8 stands for 2-8° C.

B) Comparison of Diluent Formula 0093A-22 reconstituted suspension at different stability time points:

| In-Use Time points | Description |
| --- | --- |
| 1M, D30 | Homogeneous suspension with full pink color. Small amount of API particles observed. |
| 2M, D0 | Homogeneous suspension with full pink color. Free flowing suspension. Small amount of white colored Particles observed. |
| 2M, D7 | Homogeneous suspension with pink color. Free flowing. Small amount of white colored particles observed. |
| 2M, D15 | Homogeneous suspension with pink color. Free flowing. Small amount of white colored particles observed. |
| 2M, D30 | Homogeneous suspension with full pink color. No Particles observed. |
| 3M, D0 25/60 | Homogeneous suspension with full pink color. Small amount of White Color API Particles observed. |
| 3M, D0 2-8 | Homogeneous suspension with pink color. Free flowing. Small amount of white color particles observed. |
| 3M, D7 25/60 | Homogeneous suspension with full pink color. No Particles observed. |
| 3M, D7 2-8 | Homogeneous suspension with pink color. Free flowing. Small amount of white color particles observed. |
| 3M, D15 25/60 | Homogeneous suspension with full pink color. No Particles observed. |
| 3M, D15 2-8 | Homogeneous suspension with pink color. Free flowing. Small amount of white color particles observed. |
| 3M, D30 25/60 | Homogeneous suspension with full pink color. No Particles observed |
| 3M, D30 2-8 | Homogeneous suspension with pink color. Free flowing. Small amount of white color particles observed. |
| 6M, D0 25/60 | Homogeneous suspension with pink color. The suspension observed to free flowing with very small white particles when seen from the bottom of the glass beaker. |
| 6M, D0 2-8 | Homogeneous suspension with full pink color. Free flowing suspension. Small white particles observed when seen from the bottom of the glass beaker. |
| 6M, D7 25/60 | Homogeneous suspension with pink color. The suspension observed to free flowing with very small white particles when seen from the bottom of the glass beaker. |
| 6M, D7 2-8 | Homogeneous suspension with full pink color. Free flowing suspension. Small white particles observed when seen from the bottom of the glass beaker. |
| 6M, D15 25/60 | Homogeneous suspension with pink color. The suspension observed to free flowing with very small white particles when seen from the bottom of the glass beaker. |
| 6M, D15 2-8 | Homogeneous suspension with full pink color. Free flowing suspension. Small white particles observed when seen from the bottom of the glass beaker. |
| 6M, D30 25/60 | Homogeneous suspension with pink color. The suspension observed to free flowing with very small white particles when seen from the bottom of the glass beaker. |
| 6M, D30 2-8 | Homogeneous suspension with full pink color. Free flowing suspension. Very few large white particles observed when seen from the bottom of the glass beaker. |

Note:
25/60 stands for 25° C./60% RH and 2-8 stands for 2-8° C.

Inference: Sodium CMC+1.0% w/v poloxamer 188 and Diluent Formula 0093A-22 reconstituted suspensions looked similar with respect to color (pink color) at all-time points. Small amounts of white particles were observed in both formulations at certain time points. However, the observed particles did not show a significant impact on assay and dissolution of the formulations.

3.3 Assay

The assay data for both formulations at different stability time points are provided in the table below.

Specification: Not less than (NLT) 90% and No more than (NMT) 110% of labeled amount of omeprazole.

A) HPLC Assay Comparison of sodium CMC with 1% w/v poloxamer 188 reconstituted suspension at different stability time points are shown in FIG. 1.
Note: The assay value of the 2M, Day 7 time point was found to be on the lower side because of improper shaking of reconstituted suspension bottles prior to analysis.

| | | | | | | Sodium CMC + 1.0% w/v Poloxamer 188 | | | | | |
|---|---|---|---|---|---|---|---|---|---|---|---|
| | 1M, D30 | 2M, D0 | 2M, D7 | 2M, D15 | 2M, D30 | 3M, D0 (25/60) | 3M, D0 (2-8) | 3M, D7 (25/60) | 3M, D7 (2-8) | 3M, D15 (25/60) | 3M, D15 (2-8) |
| Assay | 103.2 | 103 | 87.3 | 101.0 | 107.1 | 94.6 | 101.8 | 99.7 | 102.4 | 99.1 | 103.3 |
| % RSD | 0.93 | 0.65 | 6.91 | 0.59 | 0.42 | 0.37 | 0.59 | 0.40 | 0.70 | 0.21 | 0.72 |
| | 3M, D30 (25/60) | 3M, D30 (2-8) | 6M, D0 (25/60) | 6M, D0 (2-8) | 6M, D7 (25/60) | 6M, D7 (2-8) | 6M, D15 (25/60) | 6M, D15 (2-8) | 6M, D30 (25/60) | 6M, D30 (2-8) | |
| Assay | 97.2 | 100.8 | 101.9 | 101.2 | 104.6 | 101.5 | 101.7 | 101.3 | 100.9 | 99.2 | |
| % RSD | 0.53 | 1.59 | 1.59 | 0.60 | 1.21 | 0.43 | 0.43 | 1.48 | 0.77 | 0.58 | |

Note:
25/60 stands for 25° C./60% RH and 2-8 stands for 2-8° C.

Figure 2:
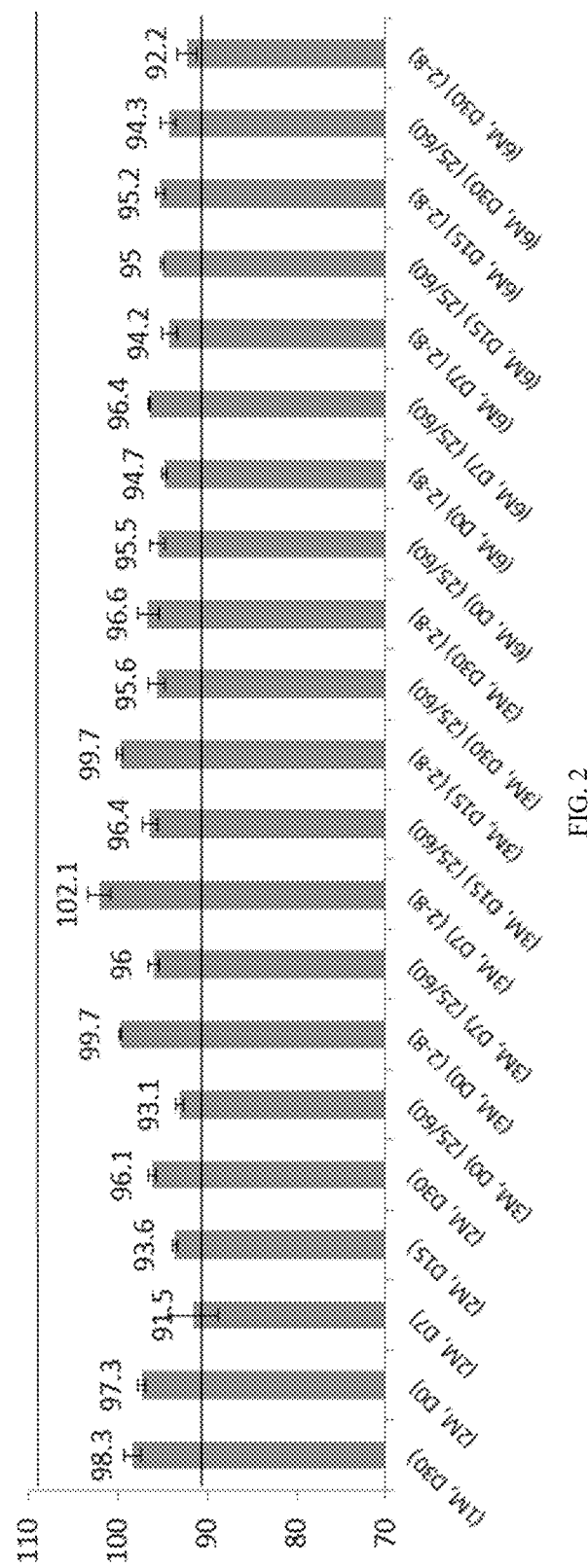
FIG. 2 includes a bar graph showing the assay comparison of Diluent Formula 0093 A-22 reconstituted suspension at different stability time points.

B) Assay Comparison of Diluent Formula 0093A-22 reconstituted suspension at different stability time points are shown in FIG. 2.

| | | | | | | Diluent Formula: 0093A-22 | | | | | |
|---|---|---|---|---|---|---|---|---|---|---|---|
| | 1M, D30 | 2M, D0 | 2M, D7 | 2M, D15 | 2M, D30 | 3M, D0 (25/60) | 3M, D0 (2-8) | 3M, D7 (25/60) | 3M, D7 (2-8) | 3M, D15 (25/60) | 3M, D15 (2-8) |
| Assay | 98.3 | 97.3 | 91.5 | 93.6 | 96.1 | 93.1 | 99.7 | 96.0 | 102.1 | 96.4 | 99.7 |
| % RSD | 0.98 | 0.36 | 2.71 | 0.22 | 0.44 | 0.45 | 0.10 | 0.59 | 1.27 | 0.81 | 0.35 |
| | 3M, D30 (25/60) | 3M, D30 (2-8) | 6M, D0 (25/60) | 6M, D0 (2-8) | 6M, D7 (25/60) | 6M, D7 (2-8) | 6M, D15 (25/60) | 6M, D15 (2-8) | 6M, D30 (25/60) | 6M, D30 (2-8) | |
| Assay | 95.6 | 96.6 | 95.5 | 94.7 | 96.4 | 94.2 | 95.0 | 95.2 | 94.3 | 92.2 | |
| % RSD | 0.89 | 1.19 | 0.90 | 0.27 | 0.12 | 0.81 | 0.11 | 0.47 | 0.90 | 1.08 | |

Note:
25/60 stands for 25° C./60% RH and 2-8 stands for 2-8° C.

Inference: The assay values for both formulations were within 90-110% at all stability time-points, except for 2M, Day 7 where the assay was found to be on the lower side. The % RSD for assay for both the formulations at all stability time points was found to be less than 2% (except for 2M, Day 7), which indicates that suspensions are homogeneous. However, the assay trend in Diluent Formula 0093A-22 was found to be on the lower side of specification range at multiple time-points. Overall, the assay values for both the formulations were high, except for the 2M, Day 7 time point.

Note: The assay value for 2M, Day 7 time point was found to be on the lower side because of improper shaking of reconstituted suspension bottles prior to analysis.

3.3.1 HPLC Assay Comparison of Diluent Formula 0093A-8

| | | | | | Diluent Formula 0093A-8 | | | | | | | |
|---|---|---|---|---|---|---|---|---|---|---|---|---|
| | 1M, D30 | 2M, D0 | 2M, D7 | 2M, D15 | 2M, D30 | 3M, D0 (25/60) | 3M, D0 (2-8) | 3M, D7 (25/60) | 3M, D7 (2-8) | 3M, D15 (25/60) | 3M, D15 (2-8) | 3M, D30 (25/60) | 3M, D30 (2-8) |
| Assay | 95.4 | 97 | 58.8 | 87 | 97.2 | 95.6 | 99.6 | 98.7 | 97.4 | 98.1 | 97.8 | 99.8 | 94.6 |
| % RSD | 21.46 | 2.52 | 8.44 | 28.36 | 0.55 | 0.06 | 0.49 | 0.48 | 0.92 | 0.81 | 0.67 | 7.02 | 0.34 |

3.4 Dissolution

Dissolution testing is a requirement for all oral solid and suspension dosage forms and is used in all phases of development for product release and stability testing. It is a key analytical test used for detecting physical changes in an active pharmaceutical ingredient (API) and in the formulated product.

Dissolution testing of both formulations was conducted in OGD (Office of Generic Drugs) media at all stability time points. Dissolution testing of a comparator commercial product, the product omeprazole with sodium bicarbonate sold under the trademark ZEGERID® powder for oral suspension, was conducted in OGD media and the results were compared to both formulations.

Specification: NLT 70% (Q) of the labeled amount of omeprazole is dissolved in 30 minutes. The quantity (Q) is the amount of dissolved active ingredient specified in the individual monograph, expressed as a percentage of the labeled content of the dosage unit.

Figure 3:
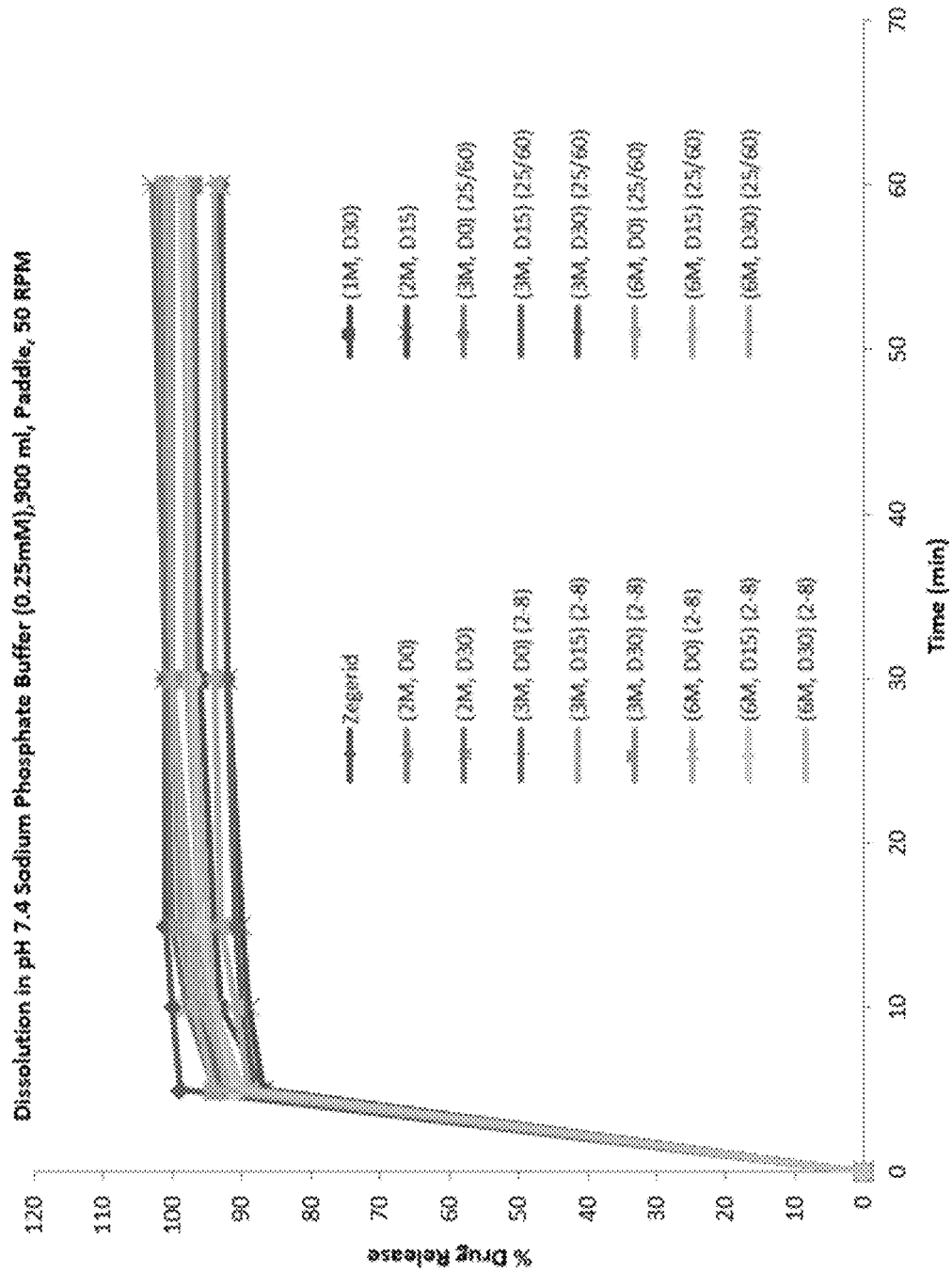
FIG. 3 includes a plot showing the dissolution profile comparison of the product omeprazole with sodium bicarbonate sold under the trademark ZEGERID® with sodium CMC with 1% w/v poloxamer reconstituted suspension at different stability time points.

Dissolution Details:
USP Apparatus: II (Paddle)
Speed: 50 rpm
Media: 0.25 mM Sodium Phosphate Buffer, pH 7.4
Volume: 900 mL
Recommended Sampling Time points: 5, 10, 15, 30, 60 minutes and recovery
Name: The product omeprazole with sodium bicarbonate sold under the trademark ZEGERID®.
Strength: 40 mg/1680 mg A) Dissolution profile comparison of the product omeprazole with sodium bicarbonate sold under the trademark ZEGERID® with sodium CMC with 1% w/v poloxamer 188 reconstituted suspension at different stability time points (FIG. 3):

| pH 7.4 SOCHUM Phosphate Buffer (0.25 mM), 900 ml, Paddle, 50 RPM Sodium CMC + 1.0% w/v Poloxamer % Drag release | | | | | | | | | | | | | | | | | |
|---|---|---|---|---|---|---|---|---|---|---|---|---|---|---|---|---|---|
| Time point (min) | Zegerid | 1M, D30 | 2M, D0 | 2M, D15 | 2M, D30 | 3M, D0 (25/60) | 3M, D0 (2-8) | 3M, D15 (25/60) | 3M, 615 (2-8) | 3M, D30 (25/60) | 3M, D30 (2-8) | 6M, D0 (25/60) | 6M, D0 (2-8) | 6M, D15 (25/60) | 6M, D15 (2-8) | 6M, D30 (25/60) | 6M, D30 (2-8) |
| 0 | 0 | 0 | 0 | 0 | 0 | 0 | 0 | 0 | 0 | 0 | 0 | 0 | 0 | 0 | 0 | 0 | 0 |
| 5 | 99 | 87 | 93 | 87 | 94 | 92 | 93 | 92 | 91 | 88 | 94 | 89 | 91 | 94 | 91 | 92 | 90 |
| 10 | 100 | 93 | 97 | 89 | 98 | 95 | 96 | 95 | 96 | 90 | 97 | 91 | 94 | 97 | 94 | 95 | 94 |
| 15 | 101 | 94 | 98 | 90 | 100 | 96 | 98 | 96 | 97 | 91 | 99 | 93 | 95 | 98 | 96 | 96 | 96 |
| 30 | 101 | 96 | 100 | 92 | 101 | 97 | 100 | 97 | 100 | 92 | 100 | 94 | 97 | 100 | 97 | 98 | 97 |
| 60 | 100 | 97 | 102 | 93 | 103 | 97 | 101 | 98 | 100 | 93 | 101 | 94 | 98 | 101 | 99 | 98 | 98 |
| Recovery | 100 | 98 | 102 | 93 | 103 | 98 | 102 | 99 | 101 | 94 | 101 | 95 | 98 | 102 | 99 | 99 | 98 |
| Time point (min) | % RSD | % RSD | % RSD | % RSD | % RSD | % RSD | % RSD | % RSD | % RSD | % RSD | % RSD | % RSD | % RSD | % RSD | % RSD | % RSD | % RSD |
| 0 | 0 | 0 | 0 | 0 | 0 | 0 | 0 | 0 | 0 | 0 | 0 | 0 | 0 | 0 | 0 | 0 | 0 |
| 5 | 2.4 | 3.0 | 1.3 | 1.4 | 0.0 | 0.7 | 1.1 | 1.1 | 1.3 | 2.3 | 0.0 | 1.7 | 0.7 | 0.6 | 1.1 | 1.1 | 0.7 |
| 10 | 1.7 | 0.0 | 1.5 | 0.7 | 0.6 | 0.6 | 1.0 | 1.1 | 0.6 | 2.2 | 1.0 | 0.7 | 0.6 | 0.6 | 0.6 | 0.6 | 0.0 |
| 15 | 1.2 | 0.0 | 1.7 | 0.7 | 0.6 | 0.6 | 1.0 | 1.0 | 1.2 | 2.3 | 1.0 | 0.6 | 0.6 | 1.0 | 0.6 | 0.6 | 0.0 |
| 30 | 1.0 | 0.0 | 1.2 | 0.7 | 1.0 | 0.6 | 1.5 | 0.6 | 0.0 | 2.3 | 0.6 | 1.3 | 0.0 | 0.6 | 0.6 | 0.6 | 0.6 |
| 60 | 1.5 | 0.0 | 1.7 | 1.8 | 0.6 | 0.6 | 1.0 | 1.0 | 1.2 | 1.8 | 0.6 | 1.3 | 0.0 | 0.6 | 0.6 | 1.2 | 0.0 |
| Recovery | 1.5 | 0.6 | 1.5 | 1.8 | 0.6 | 0.0 | 0.6 | 1.2 | 1.0 | 2.1 | 0.6 | 1.1 | 0.0 | 0.6 | 0.0 | 1.5 | 0.0 |

Figure 4:
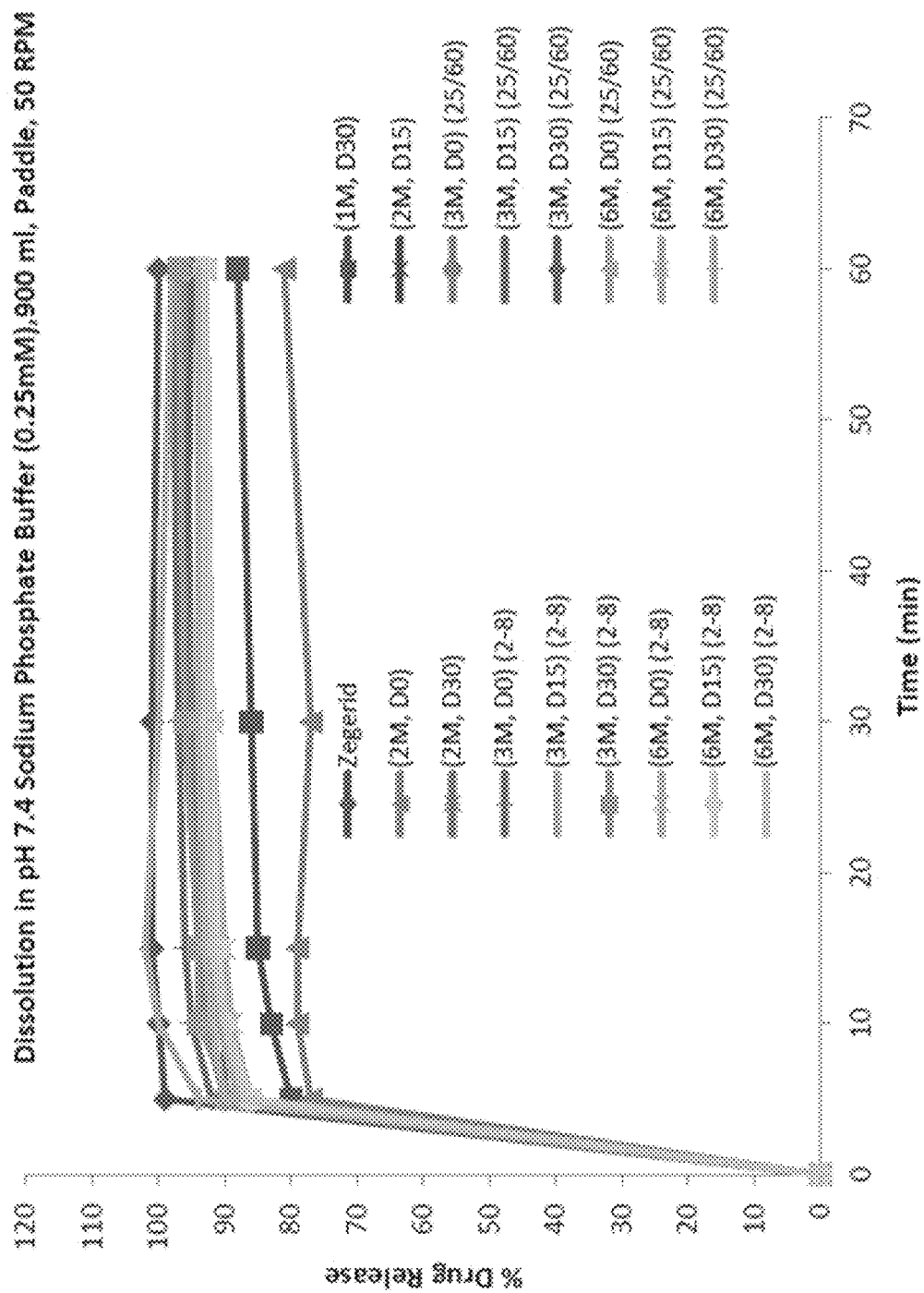
FIG. 4 includes a plot showing the dissolution profile comparison of the product omeprazole with sodium bicarbonate sold under the trademark ZEGERID® with Diluent Formula 0093A-22 reconstituted suspension at different stability time points.

B) Dissolution profile comparison of the product omeprazole with sodium bicarbonate sold under the trademark ZEGERID® with Diluent Formula 0093A-22 reconstituted suspension at different stability time points (FIG. 4):

| pH 7.4 Sodium Phosphate Buffer (0.25 mM), 900 ml, Paddle, 50 RPM Diluent Formula 0093A-22 % Drug release | | | | | | | | | | | | | | | | | |
|---|---|---|---|---|---|---|---|---|---|---|---|---|---|---|---|---|---|
| Time point (min) | Zegerid | 1M, D30 | 2M, D0 | 2M, D15 | 2M, D30 | 3M, D0 (25/60) | 3M, D0 (2-8) | 3M, D15 (25/60) | 3M, D15 (2-8) | 3M, D30 (25/60) | 3M, D30 (2-8) | 6M, D0 (25/60) | 6M, D0 (2-8) | 6M, D15 (25/60) | 6M, D15 (2-8) | 6M, D30 (25/60) | 6M, D30 (2-8) |
| 0 | 0 | 0 | 0 | 0 | 0 | 0 | 0 | 0 | 0 | 0 | 0 | 0 | 0 | 0 | 0 | 0 | 0 |
| 5 | 99 | 80 | 77 | 87 | 87 | 90 | 92 | 90 | 94 | 88 | 89 | 88 | 86 | 90 | 86 | 88 | 87 |
| 10 | 100 | 83 | 79 | 90 | 90 | 93 | 95 | 90 | 100 | 90 | 94 | 90 | 89 | 92 | 90 | 91 | 90 |
| 15 | 101 | 85 | 79 | 91 | 91 | 94 | 96 | 94 | 102 | 91 | 94 | 92 | 90 | 93 | 91 | 92 | 92 |
| 30 | 101 | 86 | 77 | 92 | 93 | 95 | 97 | 96 | 150 | 92 | 96 | 93 | 92 | 94 | 92 | 93 | 93 |
| 60 | 100 | 88 | 81 | 93 | 94 | 96 | 98 | 95 | 98 | 93 | 97 | 93 | 93 | 94 | 93 | 94 | 93 |
| Recovery | 100 | 88 | 81 | 93 | 94 | 96 | 99 | 96 | 90 | 93 | 97 | 93 | 93 | 95 | 93 | 93 | 93 |
| Time point (min) | % RSD | % RSD | % RSD | % RSD | % RSD | % RSD | % RSD | % RSD | % RSD | % RSD | % RSD | % RSD | % RSD | % RSD | % RSD | % RSD | % RSD |
| 0 | 0 | 0 | 0 | 0 | 0 | 0 | 0 | 0 | 0 | 0 | 0 | 0 | 0 | 0 | 0 | 0 | 0 |
| 5 | 2.4 | 0.0 | 5.5 | 2.4 | 1.4 | 0.7 | 0.7 | 0.7 | 7.1 | 0.7 | 0.7 | 0.7 | 0.0 | 0.7 | 0.7 | 1.1 | 1.1 |

-continued pH 7.4 Sodium Phosphate Buffer (0.25 mM), 900 ml, Paddle, 50 RPM
Diluent Formula 0093A-22
% Drug release

| 10 | 1.7 | 0.7 | 5.9 | 1.7 | 0.7 | 0.6 | 0.6 | 3.2 | 3.6 | 0.0 | 0.6 | 0.7 | 0.7 | 0.7 | 0.7 | 1.1 | 0.7 |
| 15 | 1.2 | 0.7 | 5.6 | 1.1 | 0.7 | 0.6 | 0.6 | 0.6 | 1.7 | 0.0 | 0.6 | 1.1 | 0.7 | 0.6 | 0.7 | 0.7 | 0.7 |
| 30 | 1.0 | 0.0 | 11.7 | 1.6 | 0.6 | 0.0 | 0.6 | 0.6 | 3.6 | 0.7 | 0.6 | 0.0 | 0.0 | 0.6 | 0.0 | 0.6 | 0.6 |
| 60 | 1.5 | 0.7 | 6.8 | 1.1 | 0.6 | 0.6 | 0.0 | 1.6 | 11.4 | 0.0 | 0.0 | 0.0 | 1.1 | 0.6 | 0.0 | 0.6 | 0.6 |
| Recovery | 1.5 | 1.1 | 6.0 | 0.6 | 0.0 | 0.6 | 0.0 | 1.6 | 30.4 | 0.0 | 0.0 | 0.0 | 1.1 | 0.6 | 0.0 | 0.6 | 0.6 |

Inference: The dissolution profile for sodium CMC with 1% w/v poloxamer 188 is similar to the dissolution profile of the product omeprazole with sodium bicarbonate sold under the trademark ZEGERID®. No significant difference in dissolution profile was observed between sodium CMC with 1% w/v poloxamer 188 and the product omeprazole with sodium bicarbonate sold under the trademark ZEGERID® throughout the stability testing program. Diluent Formula 0093A-22 also showed a similar dissolution profile when compared to sodium CMC with 1% w/v poloxamer 188, however it didn't show complete release at certain time points.

Note: The dissolution values for the 1M, Day 30 and 2M, Day 0 time points may have been on the lower side because of improper shaking of reconstituted suspension bottles prior to analysis.

3.4.1 Dissolution Data for Composition: Avicel CL-611 with Poloxamer 188 pH 7.4 Sodium Phosphate Buffer (0.25 mM), 900 ml, Paddle, 50 RPM
Avicel CL-611 + 1.0% w/v Poloxamer 188
% Drug release

| Time point (min) | 1M D30 | 2M, D0 | 2M, D15 | 2M, D30 | 3M, D0 (25/60) | 3M, D0 (2-8) | 3M, D15 (25/60) | 3M, D15 (2-8) | 3M, D30 (25/60) | 3M, D30 (2-8) |
|---|---|---|---|---|---|---|---|---|---|---|
| 0 | 0 | 0 | 0 | 0 | 0 | 0 | 0 | 0 | 0 | 0 |
| 5 | 75 | 76 | 90 | 31 | 102 | 94 | 46 | 83 | 55 | 51 |
| 10 | 84 | 87 | 93 | 50 | 103 | 97 | 61 | 88 | 71 | 63 |
| 15 | 87 | 91 | 93 | 67 | 104 | 98 | 68 | 91 | 78 | 74 |
| 30 | 89 | 95 | 93 | 81 | 104 | 99 | 76 | 92 | 84 | 84 |
| 60 | 90 | 97 | 95 | 89 | 105 | 100 | 81 | 93 | 88 | 92 |
| Recovery | 94 | 101 | 99 | 108 | 105 | 103 | 91 | 96 | 98 | 100 |

| Time point (min) | % RSD | % RSD | % RSD | % RSD | % RSD | % RSD | % RSD | % RSD | % RSD | % RSD |
|---|---|---|---|---|---|---|---|---|---|---|
| 0 | 0 | 0 | 0 | 0 | 0 | 0 | 0 | 0 | 0 | 0 |
| 5 | 6.1 | 15.0 | 3.6 | 20.6 | 0.6 | 5.5 | 24.3 | 1.8 | 13.1 | 8.2 |
| 10 | 3.6 | 6.9 | 1.6 | 7.2 | 1.0 | 6.0 | 18.0 | 0.7 | 14.8 | 4.0 |
| 15 | 2.3 | 3.8 | 0.6 | 18.7 | 0.6 | 4.7 | 15.7 | 0.0 | 8.5 | 3.5 |
| 30 | 2.8 | 2.1 | 1.6 | 18.0 | 1.2 | 4.9 | 16.2 | 0.0 | 6.3 | 5.4 |
| 60 | 1.9 | 0.0 | 1.6 | 15.2 | 1.0 | 3.6 | 13.7 | 0.6 | 6.9 | 3.9 |
| Recovery | 1.8 | 0.0 | 0.6 | 3.3 | 1.1 | 4.1 | 7.0 | 1.0 | 7.8 | 1.5 |

3.4.2. Dissolution Data for Composition: Diluent Formula 0093A-8 pH 7.4 Sodium Phosphate Buffer (0.25 mM), 900 ml, Paddle, 50 RPM
Diluent Formula 0093A-8
% Drug release

| Time point (min) | 1M D30 | 2M, D0 | 2M, D15 | 2M, D30 | 3M, D0 (25/60) | 3M, D0 (2-8) | 3M, D15 (25/60) | 3M, D15 (2-8) | 3M, D30 (25/60) | 3M, D30 (2-8) |
|---|---|---|---|---|---|---|---|---|---|---|
| 0 | 0 | 0 | 0 | 0 | 0 | 0 | 0 | 0 | 0 | 0 |
| 5 | 87 | 66 | 88 | 89 | 91 | 90 | 92 | 89 | 88 | 88 |
| 10 | 89 | 67 | 90 | 92 | 93 | 93 | 94 | 90 | 90 | 92 |
| 15 | 91 | 68 | 91 | 93 | 94 | 95 | 95 | 91 | 91 | 94 |
| 30 | 93 | 69 | 93 | 95 | 96 | 96 | 97 | 99 | 91 | 95 |
| 60 | 93 | 70 | 93 | 95 | 96 | 97 | 97 | 99 | 92 | 95 |
| Recovery | 93 | 69 | 93 | 96 | 97 | 97 | 98 | 94 | 92 | 95 |

-continued

| | pH 7.4 Sodium Phosphate Buffer (0.25 mM), 900 ml, Paddle, 50 RPM | | | | | | | | | |
|---|---|---|---|---|---|---|---|---|---|---|
| | Diluent Formula 0093A-8 | | | | | | | | | |
| | % Drug release | | | | | | | | | |
| Time point (min) | % RSD | % RSD | % RSD | % RSD | % RSD | % RSD | % RSD | % RSD | % RSD | % RSD |
| 0 | 0 | 0 | 0 | 0 | 0 | 0 | 0 | 0 | 0 | 0 |
| 5 | 1.1 | 8.6 | 0.7 | 1.1 | 1.1 | 0.7 | 4.8 | 3.5 | 15.7 | 0.7 |
| 10 | 0.7 | 8.8 | 0.7 | 0.7 | 0.6 | 0.6 | 4.9 | 13.7 | 15.3 | 0.0 |
| 15 | 0.0 | 9.1 | 0.7 | 1.1 | 1.3 | 0.6 | 4.2 | 9.3 | 15.4 | 1.3 |
| 30 | 0.6 | 9.0 | 0.6 | 0.6 | 0.0 | 1.0 | 4.3 | 6.5 | 15.8 | 0.0 |
| 60 | 0.0 | 9.1 | 0.0 | 1.1 | 0.6 | 0.0 | 4.5 | 11.6 | 16.2 | 0.0 |
| Recovery | 0.6 | 9.9 | 0.0 | 0.6 | 0.6 | 0.0 | 4.3 | 12.2 | 15.2 | 0.0 |

3.5 Related Substance

Monitoring the trend of increase in chemical impurities/related substances is important with respect to stability of a formulation. Related substance data developed during stability studies of a formulation play a crucial role with respect to determining a useable shelf life for a formulation.

Specification:
a. Omeprazole Related Compound F&G: NMT 0.50%
b. 5-Methoxy-1H-Benzimidazol-2-thiol: NMT 0.50%
c. Omeprazole sulphone N-Oxide: NMT 0.50%
d. Omeprazole N-Oxide: NMT 0.50%
e. Omeprazole Sulphone: NMT 0.50%
f. Omeprazole 4-Chloro analog (IMP-H): NMT 0.50%
g. Sulphide (Ufiprazole): NMT 0.50%
h. Desmethoxy Omeprazole: NMT 0.50%
i. Any other individual impurity: NMT 0.20%
j. Total impurities: NMT 2.0%

For both the formulations, testing for related substance was performed at all stability time points.

A) Related substance comparison of sodium CMC with 1% w/v poloxamer 188 reconstituted suspension at different stability time points:

| | Sodium CMC + 1.0% w/v Poloxamer 188 | | | | | | | | | | | |
|---|---|---|---|---|---|---|---|---|---|---|---|---|
| Related Substance | Omeprazole API | (1M, D30) | (2M, D0) | (2M, D30) | (3M, D0) (25/60) | (3M, D0) (2-8) | (3M, D30) (25/60) | (3M, D30) (2-8) | (6M, D0) (25/60) | (6M, D0) (2-8) | (6M, D30) (25/60) | (6M, D30) (2-8) |
| Omeprazole F&G | 0.031 | 0.0754 | 0.0149 | 0.0815 | 0.0717 | 0.022 | 0.0947 | 0.071 | 0.0505 | 0.0098 | 0.092 | 0.0542 |
| 5-Methoxy Benzamidazole 2 thiol | Less than LOQ (0.01%) | 0.0214 | ND | 0.0105 | 0.0236 | 0.0166 | 0.0071 | 0.0272 | 0.0056 | 0.0039 | 0.0025 | 0.0016 |
| Omeprazole sulphone N-Oxide | Not Detected | ND | ND | ND | ND | 0.0037 | 0.0082 | 0.0068 | ND | ND | ND | ND |
| Omeprazole N-Oxide | Less than LOQ (0.01%) | 0.0082 | 0.0086 | 0.0104 | 0.0081 | 0.0102 | 0.0101 | 0.0105 | 0.0082 | 0.0121 | 0.0089 | 0.0094 |
| Omeprazole Sulphone (IMP-A) | Less than LOQ (0.01%) | 0.0899 | 0.0179 | 0.0539 | 0.0546 | 0.0375 | 0.0866 | 0.0919 | 0.0276 | 0.0222 | 0.0189 | 0.0167 |
| Omeprazole 4-Chloro analog (IMP-H) | Less than LOQ (0.01%) | ND | ND | 0.0907 | 0.0855 | 0.0862 | 0.0058 | 0.006 | 0.0137 | 0.0057 | 0.0044 | 0.0046 |
| Omeprazole Sulphide | Less than LOQ (0.01%) | 0.1056 | 0.0333 | 0.0998 | 0.0898 | 0.123 | 0.106 | 0.1353 | 0.0492 | 0.0427 | 0.0619 | 0.1019 |
| Desmethoxy Omeprazole | Less than LOQ (0.01%) | ND | ND | ND | ND | ND | ND | ND | ND | ND | 0.0129 | 0.0172 |
| unknown | NA | 0.1163 (RRT: 0.138) | 0.0153 (RRT: 0.137) | 0.1196 (RRT: 0.141) | 0.1325 (RRT: 0.140) | 0.1088 (RRT: 0.144) | 0.1311 (RRT: 0.136) | 0.1285 (RRT: 0.136) | 0.0198 (RRT: 0.114) | 0.0154 (RRT: 0.117) | 0.0872 (RRT: 0.117) | 0.0705 (RRT: 0.117) |
| unknown | NA | 0.1489 (RRT: 0.695) | 0.0172 (RRT: 0.695) | 0.127 (RRT: 0.700) | 0.1117 (RRT: 0.698) | 0.1272 (RRT: 0.692) | 0.1235 (RRT: 0.705) | 0.1544 (RRT: 0.706) | ND | 0.0167 (RRT: 0.467) | 0.0761 (RRT: 0.481) | 0.0885 (RRT: 0.480) |
| unknown | NA | NA | NA | NA | NA | NA | NA | NA | 0.0618 (RRT: 0.264) | 0.0186 (RRT: 0.283) | 0.0214 (RRT: 0.274) | 0.008 (RRT: 0.273) |
| Total impurities | 0.05% | 0.6725 | 0.1203 | 0.6411 | 0.6181 | 0.5576 | 0.6564 | 0.7442 | 0.3880 | 0.1860 | 0.5125 | 0.4674 |

$ Actual analysis was performed on day 17 for (3M, D0) (25° C./60% RH) and on day 16 for (3M, D0).

Note:
25/60 stands for 25° C. / 60% RH and 2-8 stands for 2-8° C.

B) Related substance comparison of Diluent Formula 0093A-22 reconstituted suspension at different stability time points:

| | Diluent Formula 0093A-22 | | | | | | | | | | | |
|---|---|---|---|---|---|---|---|---|---|---|---|---|
| Related Substance | Omeprazole API | (1M, D30) | (2M, D0) | (2M, D30) | (3M, D0) (25/60) | (3M, D0) (2-8) | (3M, D30) (25/60) | (3M, D30) (2-8) | (6M, D0) (25/60) | (6M, D0) (2-8) | (6M, D30) (25/60) | (6M, D30) (2-8) |
| Omeprazole F&G | 0.031 | 0.0338 | 0.0127 | 0.0761 | 0.045 | 0.0291 | 0.0826 | 0.0398 | 0.0689 | 0.007 | 0.0821 | 0.0572 |
| 5-Methoxy Benzamidazole 2 thiol | Less than LOQ (0.01%) | 0.0157 | 0.0067 | 0.0078 | 0.0338 | 0.0234 | 0.0393 | 0.0234 | 0.0056 | 0.0062 | 0.0028 | 0.0026 |
| Omeprazole sulphone N-Oxide | Not Detected | ND | ND | ND | ND | ND | 0.0065 | ND | ND | ND | ND | ND |
| Omeprazole N-Oxide | Less than LOQ (0.01%) | 0.0084 | 0.0106 | 0.0093 | 0.0091 | 0.0088 | 0.0081 | 0.0105 | 0.016 | 0.0124 | 0.0089 | 0.0103 |
| Omeprazole Sulphone (IMP-A) | Less than LOQ (0.01%) | 0.0504 | 0.0162 | 0.059 | 0.0434 | 0.0379 | 0.0864 | 0.0679 | 0.0205 | 0.0215 | 0.0355 | 0.0162 |
| Omeprazole 4-Chloro analog (IMP-H) | Less than LOQ (0.01%) | ND | ND | 0.0973 | 0.0576 | 0.0601 | 0.005 | ND | 0.0098 | 0.0044 | 0.0058 | 0.0064 |
| Omeprazole Sulphide | Less than LOQ (0.01%) | 0.0766 | 0.0371 | 0.1045 | 0.1177 | 0.1575 | 0.1189 | 0.0941 | 0.0715 | 0.0489 | 0.0731 | 0.0865 |
| Desmethoxy Omeprazole | Less than LOQ (0.01%) | ND | ND | ND | ND | ND | ND | ND | ND | ND | 0.0166 | 0.023 |
| unknown | NA | 0.0586 (RRT: 0.137) | 0.0172 (RRT: 0.137) | 0.1058 (RRT: 0.413) | 0.1477 (RRT: 0.144) | 0.1425 (RRT: 0.141) | 0.1475 (RRT: 0.136) | 0.0755 (RRT: 0.136) | 0.0223 (RRT: 0.114) | 0.0175 (RRT: 0.114) | 0.1035 (RRT: 0.117) | 0.0765 (RRT: 0.177) |
| unknown | NA | 0.0727 (RRT: 0.694) | 0.0191 (RRT: 0.695) | 0.0977 (RRT: 0.703) | 0.0881 (RRT: 0.691) | 0.1056 (RRT: 0.689) | 0.1093 (RRT: 0.707) | 0.0889 (RRT: 0.703) | ND | 0.0251 (RRT: 0.468) | 0.0572 (RRT: 0.480) | 0.0762 (RRT: 0.480) |
| unknown | NA | NA | NA | NA | NA | NA | NA | NA | 0.0825 (RRT: 0.264) | 0.007 (RRT: 0.265) | 0.004 (RRT: 0.255) | 0.0049 (RRT: 0.256) |
| Total impurities | 0.05% | 0.3663 | 0.1325 | 0.5990 | 0.5799 | 0.5899 | 0.7371 | 0.4619 | 0.5021 | 0.2169 | 0.5340 | 0.4744 |

$ Actual analysis was performed on day 17 for (3M, D0) (25° C./60% RH) and on day 16 for (3M, D0) (2-8° C.).
Note:
25/60 stands for 25° C. / 60% RH and 2-8 stands for 2-8° C.

Inference: Five impurities (Omeprazole F&G, Omeprazole Sulphone, Omeprazole Sulphide and Unknown impurities at Relative Retention Rate (RRT): 0.138, RRT: 0.706, RRT: 0.117 and RRT: 0.480 (determined by HPLC) showed increase in trend in stability and these impurities can be considered as degradants. However, individual known and unknown impurity levels were <0.2% in both the formulations. Overall, both the formulations were acceptable with respect to related substance content.

3.5.1 Related Substance Data for the Composition: Sodium CMC without Poloxamer 188 & Sodium Bicarbonate in Physical Mixture Example 4: Freeze Thaw Studies to Determine Tendency for Gel Formation During the preliminary stage of diluent development, the diluent was manufactured using Xanthan gum as a polymer/viscosity building agent. Gel formation was observed in the diluent upon storage at 2-8° C. The gel was characterized further to understand the composition of the gel by Titrimetric and DSC method.

Titrimetric method: Based on the gel characterization, from the assay analysis it was found that 901.60 mg omeprazole

| Sodium CMC without Poloxamer 188 & Sodium Bicarbonate in physical mixture | | | | | | | |
|---|---|---|---|---|---|---|---|
| Related Substance | 1M, D30 | 2M, D0 | 2M, D30 | 3M, D0 (25/60) | 3M, D0 (2-8) | 3M, D30 (25/60) | 3M, D30 (2-8) |
| Omeprazole F&G | 0.0825 | 0.0154 | 0.0938 | 0.1043 | 0.035 | 0.1366 | 0.0817 |
| 5-Methoxy Benzamidazole 2 thiol | 0.0494 | 0.0076 | 0.0303 | 0.0499 | 0.0098 | 0.0608 | 0.0461 |
| Omeprazole sulphone N-Oxide | 0.2074 | 0.024 | 0.2113 | 0.1931 | 0.1159 | 0.0089 | ND |
| Omeprazole N-Oxide | 0.009 | 0.0121 | 0.0103 | 0.011 | 0.0117 | 0.0094 | 0.0099 |
| Omeprazole Sulphone (IMP-A) | 0.0745 | 0.0189 | 0.0787 | 0.0506 | 0.0149 | 0.1494 | 0.0704 |
| Omeprazole 4-Chloro analog (IMP-H) | ND | ND | 0.2441 | 0.0931 | 0.052 | ND | 0.0068 |
| Omeprazole Sulphide | 0.2697 | 0.061 | 0.2208 | 0.218 | 0.3168 | 0.24 | 0.2589 |
| Desmethoxy Omeprazole | ND | ND | ND | ND | ND | ND | ND |
| Maximum unknown | 0.1717 | 0.0265 | 0.145 | 0.1875 | 0.1637 | 0.1796 | 0.1655 |
| Total impurities | 1.0508 | 0.1714 | 1.1214 | 0.9858 | 0.8434 | 1.3175 | 0.9926 | gel contains 520.8 mg of sodium bicarbonate. Hence it can be concluded that major portion of the gel consist of Sodium bicarbonate (57.8%).

Figure 5:
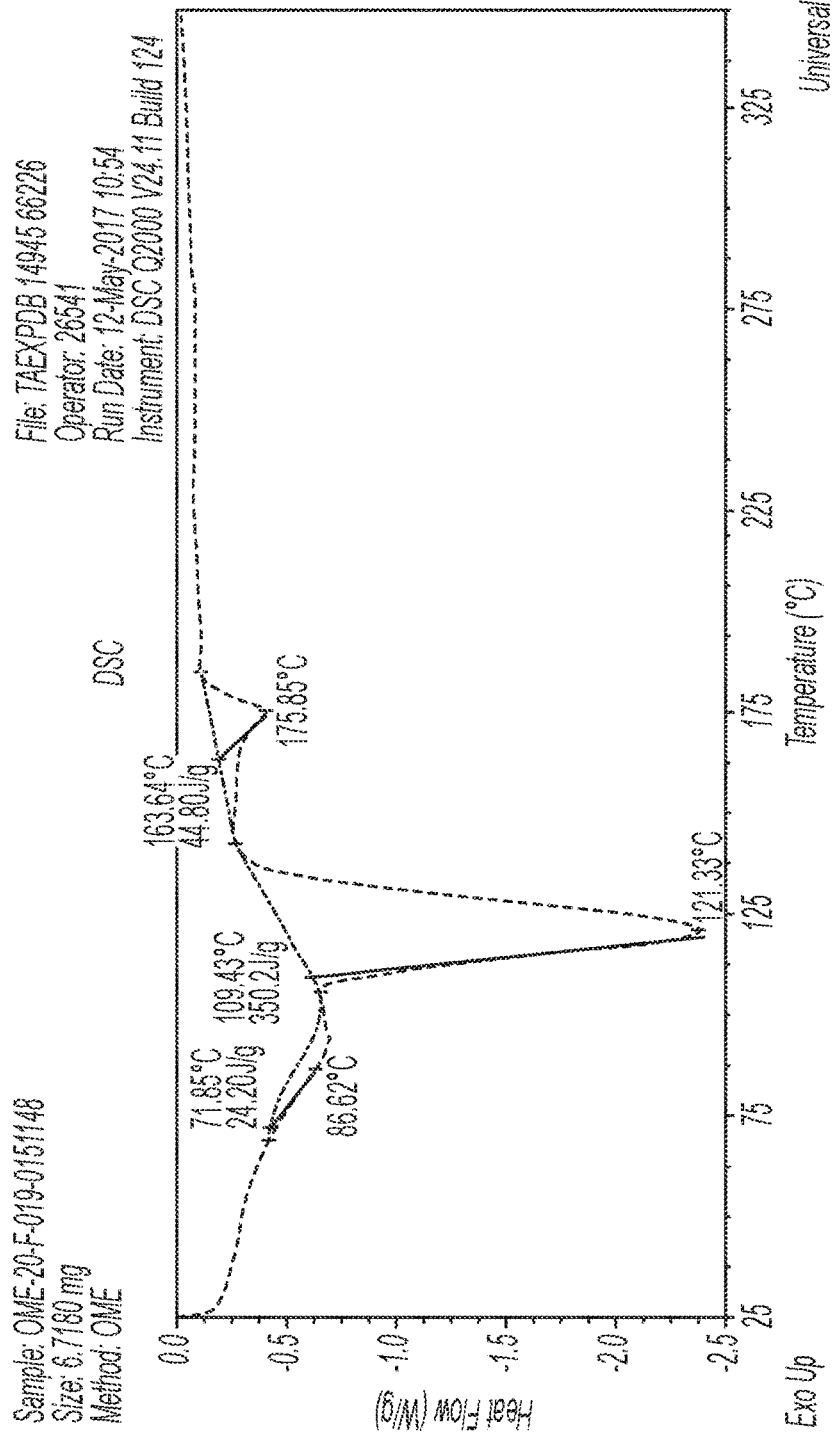
FIG. 5 includes a plot showing the DSC analysis of a diluent containing xanthan gum as the polymer/viscosity building agent.
Figure 6:
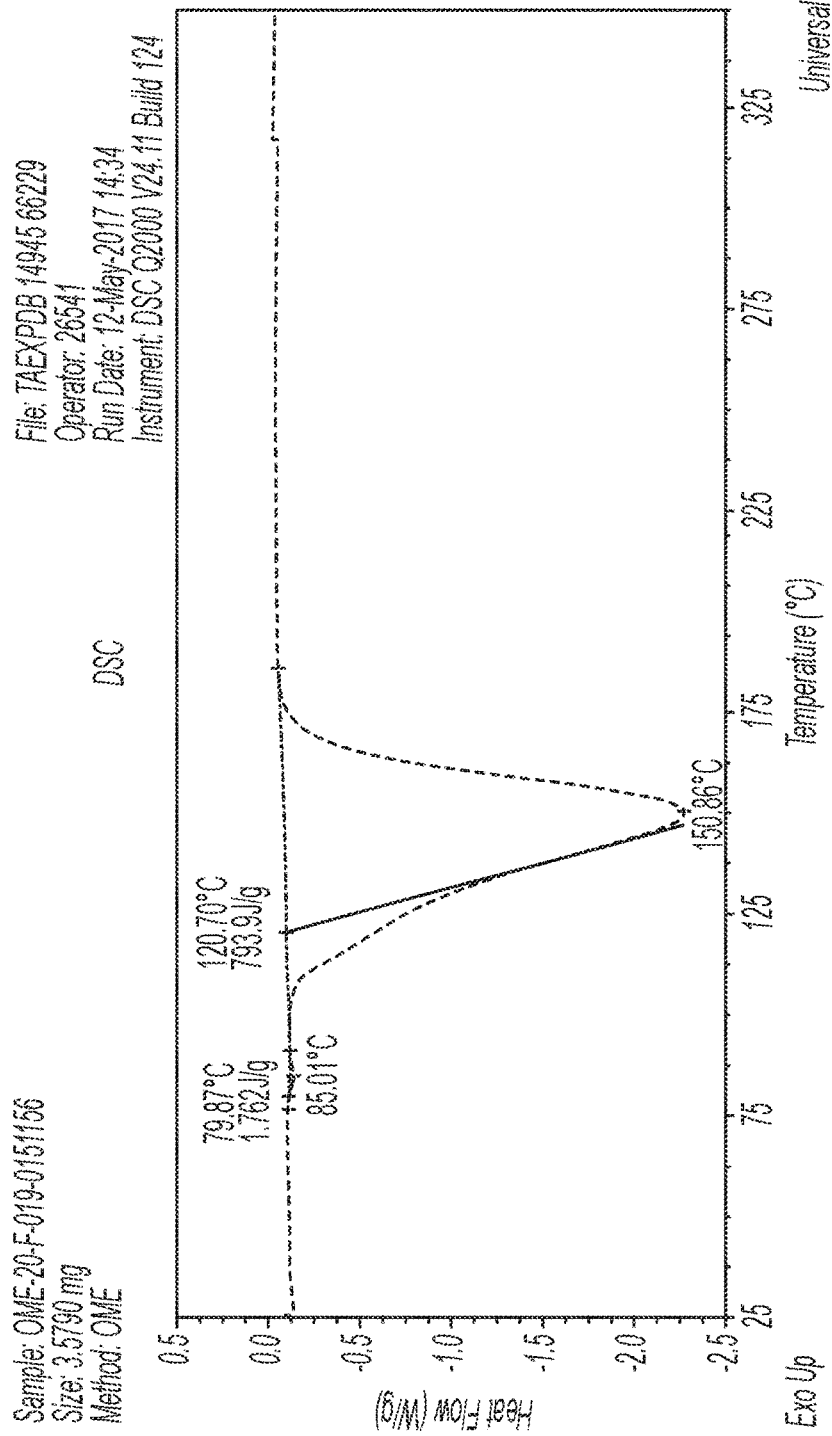
FIG. 6 includes a plot showing the DSC analysis of sodium bicarbonate.

DSC method: The results of the gel analyzed by DSC are shown in FIG. 5. The results of the sodium bicarbonate analyzed by DSC methods are shown in FIG. 6. In the DSC results, the gel showed a sharp endothermic event similar to sodium bicarbonate, but a shift in the peak was observed. Based on the enthalpy values, the gel had around 50% of sodium bicarbonate.

Based on the Titrimetric and DSC data, it was concluded that the major component of the gel was sodium bicarbonate. As part of the reformulation efforts, changes were made in the diluent formulation compositions. To understand the gel formation phenomenon in the diluents presented herein, a freeze thaw study was conducted to assess the gel formation phenomenon under stressed conditions.

The freeze thaw studies were conducted by storing the samples for around 5-10 days in 2-8° C. and −20° C. storage conditions alternatively for multiple cycles. Briefly, the diluent was placed in a −20° C. freezer for 5-10 days, then the diluent was moved to a refrigerator (2-8° C.) to allow it to thaw overnight, and then it was left at room temperature (~25±5° C.) for at least 24 hours. This represented a singled cycle, and was repeated for multiple cycles. After each cycle, the formulation was visually observed for gel formation.

Freeze Thaw Study 1: All the 6 prototype formulations were subjected to the freeze thaw study (−20° C. to 2-8° C.).

| Formulation | 2-8° C. | −20° C. | 2-8° C. | 2-8° C. | −20° C. | 2-8° C. |
|---|---|---|---|---|---|---|
| Sodium CMC with Poloxamer 188 | x | x | x | x | x | x |
| Avicel CL-611 with Poloxamer 188 | x | x | x | x | x | x |
| Sodium CMC without Poloxamer188 | x | x | x | x | x | x |
| Sodium CMC without Poloxamer 188 & Sodium Bicarbonate in physical mixture | x | x | x | x | x | x |
| Diluent Formula 0093A-8 | x | ✓ | ✓ | ✓ | ✓ | x |
| Diluent Formula 0093A-22 | x | ✓ | ✓ | x | ✓ | x |

Note:
symbol "x" means no gel formation was observed and symbol "✓" means gel formation was observed.

No gel formation was observed during the freeze thaw cycles in the first 4 diluent formulations in the table above. However, gel formation was observed in both Diluent Formula 0093A-8 and Diluent Formula 0093A-22.

Freeze Thaw Study 2 (Test No: OME-20-F-051): To evaluate the gel formation, formulations with similar composition to that of Diluent Formula 0093A-22 and Diluent Formula 0093A-8 were made at a second facility and a $2^{nd}$ freeze thaw study was performed.

| Formulation | 2-8° C. | −20° C. | 2-8° C. | −20° C. | 2-8° C. |
|---|---|---|---|---|---|
| Diluent Formula 0093A-8 (Made in $2^{nd}$ facility) | x | ✓ | x | x | x |
| Diluent Formula 0093A-22 (Made in $2^{nd}$ facility) | x | ✓ | x | x | x |
| Diluent Formula 0093A-8 | x | ✓ | x | ✓ | x |
| Diluent Formula 0093A-22 | x | ✓ | x | ✓ | x |

Note:
symbol "x" means no gel formation was observed and symbol "✓" means gel formation was observed.

Gel formation was observed in both the diluents indicating that Diluent Formula 0093A-8 and Diluent Formula 0093A-22 compositions have a tendency to form a gel.

Freeze Thaw Study 3: To further evaluate the gel formation in Diluent Formula 0093A-22, a formulation with similar composition to Diluent Formula 0093A-22 was made but the HEC was replaced with sodium CMC to evaluate the impact of the polymer/suspending agent on gel formation. The results are shown in the table below:

| Formulation | −20° C. | 2-8° C. | −20° C. |
|---|---|---|---|
| Diluent Formula 0093A-22 (HEC was replaced with sodium CMC) | ✓ | x | ✓ |

Note:
symbol "x" means no gel formation was observed and symbol "✓" means gel formation was observed.

Gel formation was observed, indicating that neither HEC nor sodium CMC may be responsible for the gel formation tendency.

Freeze Thaw Study 4: To further evaluate the gel formation in Diluent Formula 0093A-22, a formulation with similar composition except with removal of glycerin was made to evaluate the impact of the co-solvent in gel formation. The results are shown in the table below:

| Formulation | 2-8° C. | −20° C. | 2-8° C. | −20° C. | 2-8° C. | −20° C. |
|---|---|---|---|---|---|---|
| Diluent Formula 0093A-22 (Without Glycerin) | x | x | x | x | x | x |
| Diluent Formula 0093A-22 | x | ✓ | x | ✓ | x | x |

Note:
symbol "x" means no gel formation was observed and symbol "✓" means gel formation was observed.

Gel formation was not observed, indicating that glycerin may be responsible for the gel formation tendency in diluent Formula 0093A-22.

Freeze Thaw Study 5: To confirm the results, an additional freeze thaw study was performed by manufacturing a formulation with a similar composition to that of the Diluent Formula 0093A-22 and comparing it with a test formulation of a similar composition to that of Diluent Formula 0093A-22 except without glycerin. The results are shown in the table below:

| Formulation | 2-8° C. | −20° C. | 2-8° C. | −20° C. |
|---|---|---|---|---|
| Diluent Formula 0093A-22 (Without Glycerin) | x | x | x | x |
| Diluent Formula 0093A-22 | x | ✓ | x | ✓ |

Note:
symbol "x" means no gel formation was observed and symbol "✓" means gel formation was observed.

Gel formation was not observed in the test formulation without glycerin, while gel was formed in the test formulation with glycerin, which further confirmed the role of glycerin in gel formation.

Freeze Thaw Study 6: A freeze thaw study was performed to understand the gel formation phenomenon in the xanthan gum based formulation. A test formulation of the xanthan gum based formulation and two test formulations of the sodium CMC based formulation were used for the study.

| Formulation | 2-8° C. | −20° C. | 2-8° C. | 2-8° C. | −20° C. | 2-8° C. |
|---|---|---|---|---|---|---|
| Sodium CMC with poloxamer 188 (sodium CMC lot: AA6727879) | x | x | x | x | x | x |
| Sodium CMC with poloxamer 188 (sodium CMC lot: AA6552172) | x | x | x | x | x | x |
| Xanthan gum with poloxamer 188 | x | ✓ | x | x | ✓ | x |

Note:
symbol "x" means no gel formation was observed and symbol "✓" means gel formation was observed.

Gel formation was observed in the xanthan gum formulation. However, no gel formation was observed in the sodium CMC test formulations. This study confirmed the gel formation tendency in the xanthan gum based formulation.

Inference: Based on the results of the freeze thaw studies, it can be concluded that the risk of gel formation is high in the xanthan based formulation and Diluent Formula 0093A-22 because of the presence of co-solvents (glycerin and propylene glycol) compared to the formulation containing sodium CMC+1.0% w/v poloxamer 188.

Also as per the previous gel characterization, it was found that sodium bicarbonate is the major portion of the gel (white mass); hence complete solubilization of sodium bicarbonate during the diluent manufacturing process should be ensured to prevent gel formation upon long term stability.

Example 5: Evaluation of Pharmacokinetic Effects of Poloxamer

Pharmacokinetics describes how the body affects a specific drug after administration through the mechanisms of absorption and distribution, as well as the metabolic changes of the substance in the body and the effects and routes of excretion of the metabolites of the drug. Pharmacokinetic properties of drugs are affected by the route of administration and the dose of administered drug. These may affect the absorption rate.

Omeprazole is a BCS Class II molecule with a half-life of 0.5-1 hrs, a log P value of 2.43 and molecular weight of 345.417 g/mole. It is a moderate P-gp substrate and does not have P-gp inhibition effects.

As used, the term "P-gp substrate" refers to a substrate for P-glycoprotein, which is a cell-membrane protein that functions as an ATP-dependent efflux pump. Essentially, it transports the substrate from the intracellular to the extracellular compartment, hence modulating drug bioavailability.

A pharmacokinetic evaluation of marketed formulations of omeprazole is shown in the table below:

| Parameters | Zegerid-IR Capsule | Zegerid-Powder for oral suspension | Prilosec-DR Capsule |
|---|---|---|---|
| Composition | Omeprazole, sodium bicarbonate, croscarmellose sodium and sodium stearyl fumarate | Omeprazole, sodium bicarbonate, xylitol, sucrose, sucralose, xanthan gum, and flavorings | Cellulose, disodium hydrogen phosphate, hydroxypropyl cellulose, hypromellose, lactose, mannitol, sodium lauryl sulfate and other ingredients. |

-continued

| Parameters | Zegerid-IR Capsule | Zegerid-Powder for oral suspension | Prilosec-DR Capsule |
|---|---|---|---|
| Dose | 20 mg and 40 mg | 20 mg and 40 mg | 10 mg, 20 mg and 40 mg |
| Peak Plasma Concentration | 10 to 90 mins | 10 to 90 mins | 30 to 210 mins |
| Absolute Bioavailability | 30 to 40% | 30 to 40% | 30 to 40% |

As shown in the table above, the Peak Plasma concentration is achieved very rapidly with absolute bioavailability around 30 to 40%, which represents that permeability of omeprazole is not a rate-limiting step. However, since omeprazole is a BCS Class II molecule, its solubility may play a role in its pharmacokinetic effect.

Inactive ingredients which are used in the formulation can have an impact on the pharmacokinetic behavior of a drug. Poloxamer being a Surfactant/Wetting Agent may play a role in the bioavailability of omeprazole.

A) Impact of Poloxamer Content on Solubility

Based on a literature survey, the CMC of poloxamer 188 P is disclosed as 2.6 mg/mL and 4.0 mg/mL in different articles. Currently, sodium CMC with 1% w/v poloxamer 188 formulation has 10 mg/mL poloxamer 188 content which is near to its CMC. Hence the risk of 1% w/v poloxamer 188 having an adverse effect on the solubility of omeprazole may be minimal.

Phase solubility data of omeprazole at different concentrations of poloxamer 188 (0%, 0.5%, 1%, 2% and 4% w/v) were generated to understand the impact of poloxamer 188 on the solubility of omeprazole.

| Impact of Poloxamer 188 on Solubility of Omeprazole | | | | | |
|---|---|---|---|---|---|
| % w/v Poloxamer Content | 0 | 0.5 | 1 | 2 | 4 |
| Soluble fraction (%) | 10.9 | 15.6 | 17.1 | 47.8 | 47.3 |
| Soluble fraction (mg/ml) | 0.218 | 0.313 | 0.342 | 0.957 | 0.946 |

Up to 1% w/v concentration, poloxamer 188 content did not show any significant impact on the increase in omeprazole solubility; however at higher poloxamer 188 content, the omeprazole solubility increased significantly.

B) Impact of Poloxamer Content on Permeability

Poloxamer has been shown to affect activity of APIs. For instance, it affects permeability of ketoprofen (log p: 3.12) and nadolol (log p: 0.71). Decrease in permeability was observed with increase in poloxamer concentration beyond 10 mg/mL for Ketoprofen. However, poloxamer didn't show a significant effect for nadolol which is a hydrophilic compound relative to ketoprofen.

The diluents of the present disclosure are targeting low concentrations of poloxamer (e.g., poloxamer 188) (1.0% w/v) for the sodium CMC with 1% w/v poloxamer 188 formulation and omeprazole log p is 2.43. The use of poloxamer raises the chances of micellar contribution on permeability. Use of a higher concentration of poloxamer (e.g., poloxamer 188) >10 mg/mL, for instance, may have an even greater impact on the permeability of omeprazole. However, as shown herein, when poloxamer 188 is combined with sodium CMC, the activity of omeprazole is not impacted.

Example 6: Summary of Findings

Out of the 6 diluents, the sodium CMC+1% w/v poloxamer 188 and Diluent Formula 0093A-22 look promising with respect to assay, dissolution and related substance content upon storage.

Diluent Formula 0093A-22 exhibited gel formation in freeze thaw studies indicating the potential risk of gel formation during shelf life of the diluent.

Generally, the presence of poloxamer 188 may be expected to impact the plasma-concentration profiles for omeprazole. Since, Diluent Formula 0093A-22 has a relatively higher amount of poloxamer 188, the poloxamer 188 was expected to impact pharmacokinetics. However, it did not.

Example 7: Supporting Studies 7.1 Reconstitution and Shaking Study

To evaluate the impact of the reconstitution procedure and shaking time prior to analysis on assay results, the following experiments were carried out. Two different reconstitution procedures were used:

Reconstitution Procedure 1: Unless otherwise stated, this was the reconstitution procedure used for experiments herein that required reconstitution.
  1. Weigh required amount of omeprazole API in a bottle.
  2. Add required amount of sodium CMC with 1% w/v poloxamer 188 diluent in the omeprazole API filled bottle and shake for 60 seconds.

Reconstitution Procedure 2:
  1. Weigh required amount of omeprazole API in a bottle.
  2. Take the required amount of sodium CMC+1% w/v poloxamer 188 diluent and add around half the amount of diluent to the omeprazole API filled bottle and shake for 60 seconds. Add the remaining half amount to the same bottle and shake for 30 seconds.

For prototype stability studies, reconstitution was performed using reconstitution procedure 1 until the 3M time point and reconstitution procedure 2 for the 6M time point. For the formulation robustness study, reconstitution was performed using reconstitution procedure 2.

Samples that had undergone each reconstitution procedure were submitted and different shaking intervals i.e., 0, 10, 30 and 60 seconds were evaluated prior to assay analysis at Day 0 and Day 30 after reconstitution.

The assay results are shown below:

| | | Reconstitution Procedure | | | | | | | |
|---|---|---|---|---|---|---|---|---|---|
| | | Procedure 1 | | | | Procedure 2 | | | |
| | | Shaking time (Sec) | | | | | | | |
| | | 0 | 10 | 30 | 60 | 0 | 10 | 30 | 60 |
| | | DAY-1 | | | | | | | |
| Assay | | 56.3 | 71.9 | 92.9 | 98.9 | 64.5 | 72.8 | 102.0 | 82.6 |
| | | 55.8 | 88.4 | 99.5 | 102.8 | 66.6 | 93.2 | 104.1 | 99.8 |
| | | 56.3 | 100.8 | 105.0 | 103.6 | 66.3 | 103.8 | 106.2 | 107.3 |
| Average | | 56.1 | 87.0 | 99.1 | 101.8 | 65.8 | 89.9 | 104.1 | 96.6 |
| % RSD | | 0.52 | 16.67 | 6.12 | 2.47 | 1.73 | 17.53 | 2.02 | 13.11 |
| | | DAY-30 | | | | | | | |
| Assay | | 83.9 | 98.5 | 98.0 | 103.4 | 69.5 | 101.0 | 101.5 | 101.2 |
| | | 84.6 | 112.5 | 109.2 | 103.7 | 32.9 | 102.2 | 103.7 | 102.7 |
| | | 83.6 | 108.7 | 96.7 | 102.3 | 37.7 | 103.4 | 101.6 | 103.6 |
| Average | | 84.0 | 106.6 | 101.3 | 103.1 | 46.7 | 102.2 | 102.3 | 102.5 |
| % RSD | | 0.61 | 6.79 | 6.78 | 0.72 | 42.59 | 1.17 | 1.21 | 1.18 |

Inference: For reconstitution procedure 1, based on the assay results, it can be concluded that 60 seconds of shaking prior to analysis is adequate. For reconstitution procedure 2, based on the assay results, it can be concluded that 30 seconds and 60 seconds of shaking prior to analysis is adequate. However as a precautionary step, 60 seconds of shaking should be performed.

7.2 Multimedia Dissolution Multimedia dissolution was performed in three different types of dissolution media:

1. 0.01 N HCl
2. pH 4.5 Acetate Buffer
3. pH 6.0 Phosphate Buffer

Figure 7:
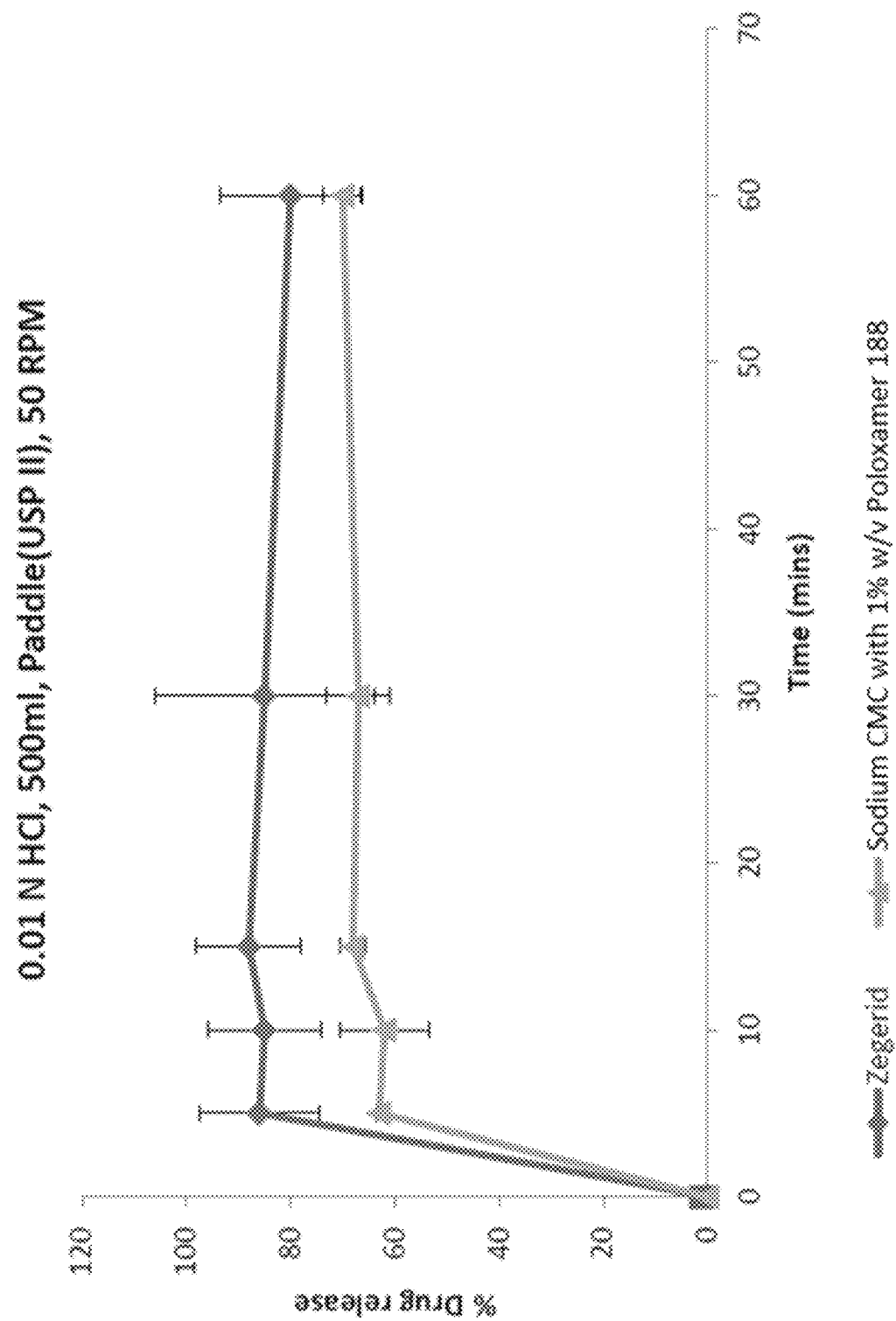
FIG. 7 includes a plot showing the dissolution profile comparison of the product omeprazole with sodium bicarbonate sold under the trademark ZEGERID® and the sodium CMC+1% w/v poloxamer 188 reconstituted suspension in 0.01 N HCl dissolution media.

Dissolution Data for 0.01 N HCl (FIG. 7):

| Omeprazole Drug Release (% Label Claim) | | |
| --- | --- | --- |
| Dissolution Parameters | 0.01 N HCl, 500 ml, Paddle (USP II), 50 RPM | |
| Time | ZEGERID® (Powder for Oral Suspension) | OME-20-F-063 (Sodium CMC with 1% w/v Poloxamer 188) |
| 0 | 0 | 0 |
| 5 | 86 | 63 |
| 10 | 85 | 62 |
| 15 | 88 | 68 |
| 30 | 85 | 67 |
| 60 | 80 | 70 |
| Time | Standard Deviation (n = 3) | Standard Deviation (n = 3) |
| 0 | 0 | 0 |
| 5 | 11.5 | 0.6 |
| 10 | 10.7 | 8.7 |
| 15 | 10.0 | 2.5 |
| 30 | 21.1 | 6.0 |
| 60 | 13.4 | 3.8 |

Figure 8:
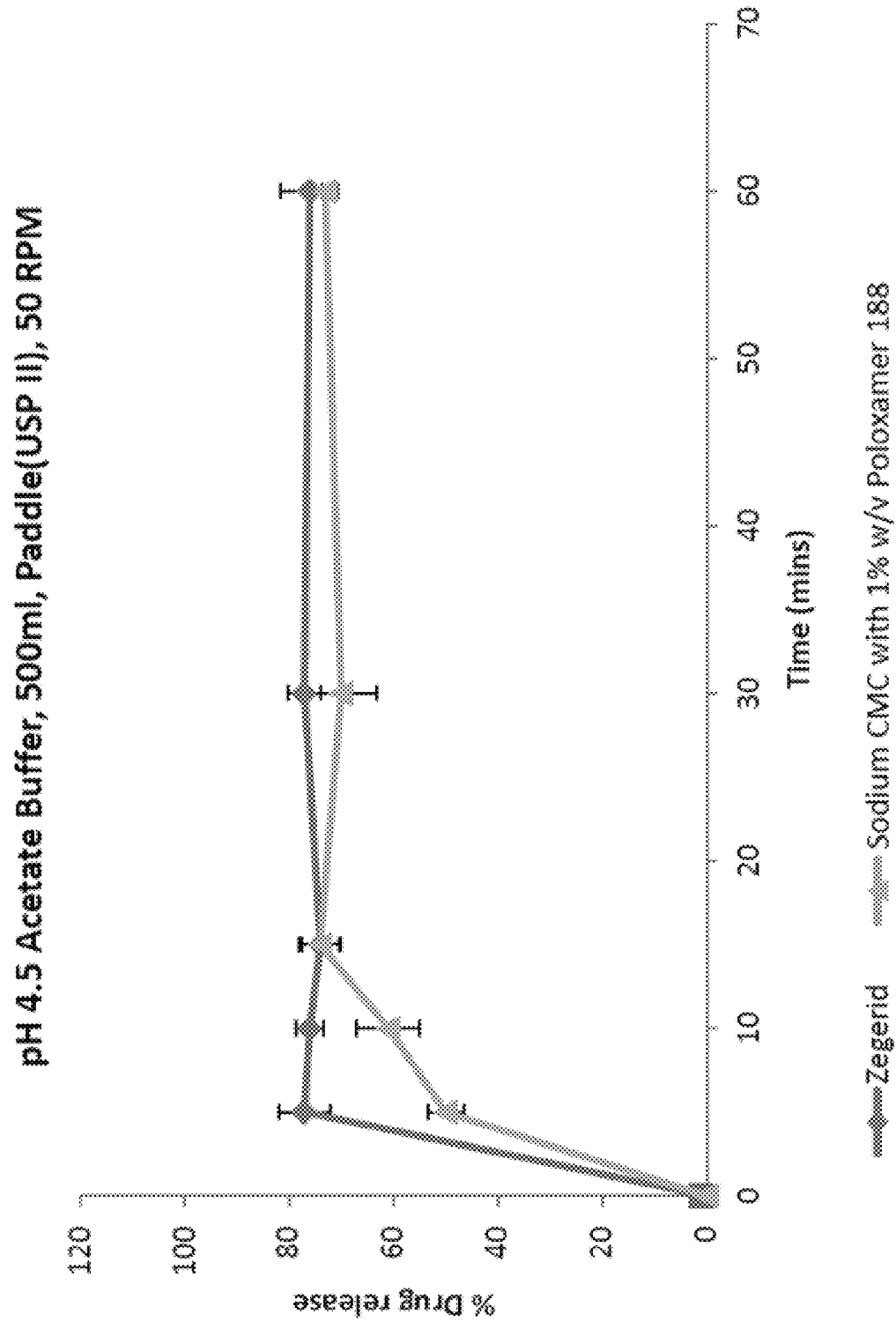
FIG. 8 includes a plot showing the dissolution profile comparison of the product omeprazole with sodium bicarbonate sold under the trademark ZEGERID® and the sodium CMC+1% w/v poloxamer 188 reconstituted suspension in pH 4.5 acetate buffer media.

Dissolution Data for pH 4.5 Acetate Buffer (FIG. 8):

| Omeprazole Drug Release (% Label Claim) | | |
| --- | --- | --- |
| Dissolution Parameters | pH 4.5 Acetate Buffer, 500 ml, Paddle (USP II), 50 RPM | |
| Time | ZEGERID® (Powder for Oral Suspension) | OME-20-F-063 (Sodium CMC with 1% w/v Poloxamer 188) |
| 0 | 0 | 0 |
| 5 | 77 | 50 |
| 10 | 76 | 61 |
| 15 | 74 | 74 |
| 30 | 77 | 70 |
| 60 | 76 | 73 |
| Time | Standard Deviation (n = 3) | Standard Deviation (n = 3) |
| 0 | 0 | 0 |
| 5 | 5.0 | 3.5 |
| 10 | 2.6 | 6.1 |
| 15 | 4.0 | 3.6 |
| 30 | 3.2 | 6.9 |
| 60 | 5.5 | 0.6 |

Figure 9:
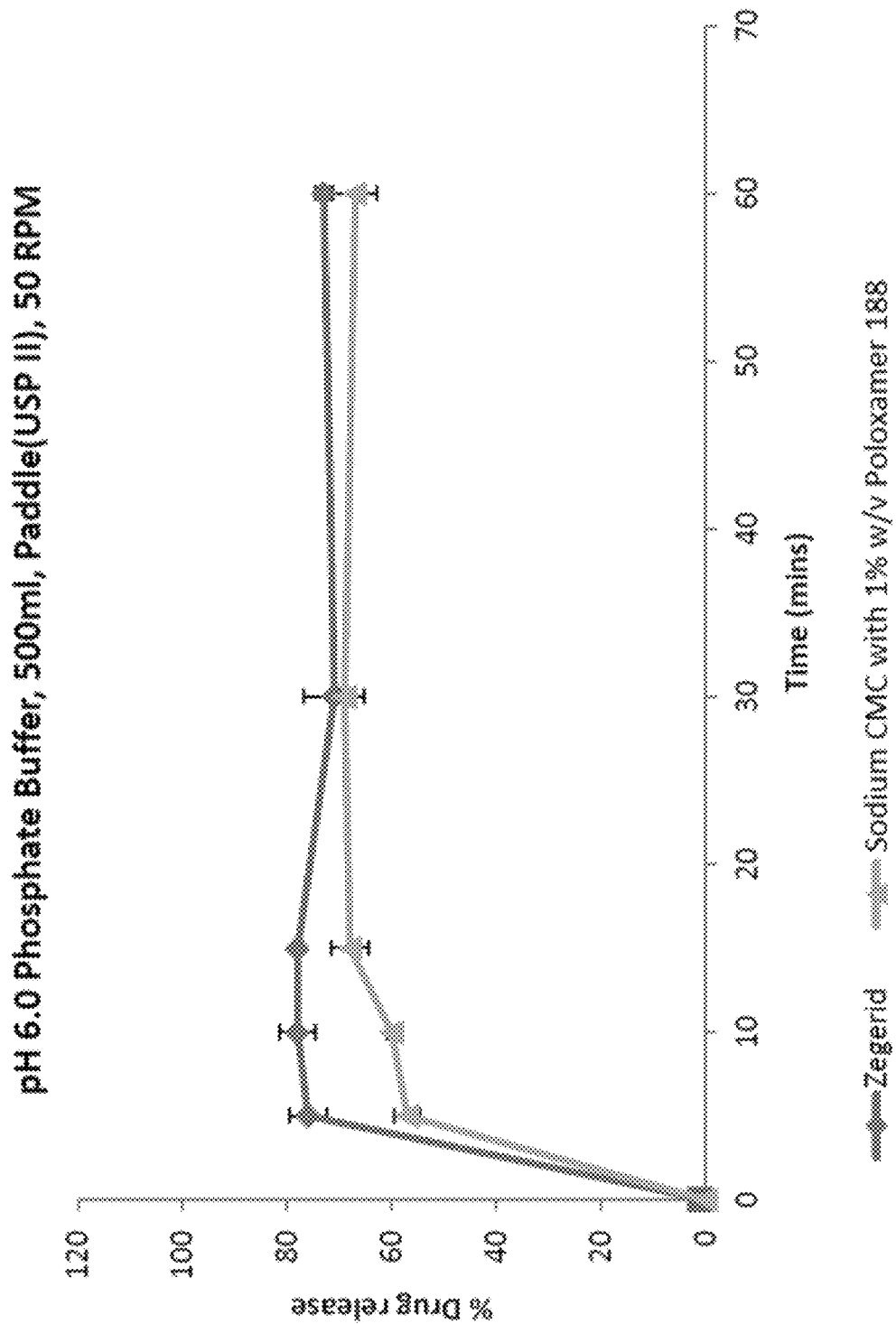
FIG. 9 includes a plot showing the dissolution profile comparison of the product omeprazole with sodium bicarbonate sold under the trademark ZEGERID® and the sodium CMC+1% w/v poloxamer 188 reconstituted suspension in pH 6.0 phosphate buffer media.

Dissolution Data for pH 6.0 Phosphate Buffer (FIG. 9):

| Omeprazole Drug Release (% Label Claim) | | |
| --- | --- | --- |
| Dissolution Parameters | pH 6.0 Phosphate Buffer, 500 ml, Paddle (USP II), 50 RPM | |
| Time | ZEGERID® (Powder for Oral Suspension) | OME-20-F-063 (Sodium CMC with 1% w/v Poloxamer 188) |
| 0 | 0 | 0 |
| 5 | 76 | 57 |
| 10 | 78 | 60 |
| 15 | 78 | 68 |
| 30 | 71 | 69 |
| 60 | 73 | 67 |
| Time | Standard Deviation (n = 3) | Standard Deviation (n = 3) |
| 0 | 0 | 0 |
| 5 | 3.6 | 2.5 |
| 10 | 3.5 | 1.0 |
| 15 | 1.0 | 3.6 |
| 30 | 5.7 | 1.0 |
| 60 | 1.5 | 4.2 |

Inference: For multimedia dissolution in all the three types of media the dissolution of sodium CMC with 1% w/v poloxamer 188 was found to be slower compared to the product omeprazole with sodium bicarbonate sold under the trademark ZEGERID® (Powder for Oral Suspension).

7.3 Viscosity

Viscosity was evaluated for the sodium CMC with 1% w/v poloxamer 188 diluent and reconstituted suspension. Viscosity testing was performed using Anton Paar Rheo-Compass. The viscosity analysis was performed in order to understand:

A. Impact of lot to lot variability with respect to sodium CMC

B. Impact on viscosity during stability.

A) Impact of Lot to Lot Variability with Respect to Sodium CMC

Three different sodium CMC lots were used for viscosity analysis of the diluent and reconstituted suspension using an Anton Paar RheoCompass at about 25° C.

| Viscosity of 2% w/v Sodium CMC as per CoA (mPa·s) | Viscosity of Diluent (mPa·s) | Viscosity of Reconstituted Suspension (mPa·s) |
| --- | --- | --- |
| 750 | 107 | 128.2 |
| 810 | 146 | 136.2 |
| 760 | 115.1 | 115 |

Note:
The viscosity measurement in the table above were for freshly prepared reconstituted suspensions from therir respective diluents.
Sodium CMC used in the preparation of diluents is 1.2% w/v.

Note: The viscosity measurements in the table above were for freshly prepared reconstituted suspensions from their respective diluents. Sodium CMC used in the preparation of diluents is 1.2% w/v.

Inference: Viscosity results for diluent and reconstituted suspension for all the above tested formulations were found to be in the range of 100-150 mPa·s.

B) Impact on Viscosity During Stability

| Viscosity of 2% w/v Sodium CMC as per CoA (mPa·s) | Viscosity of Diluent (mPa·s) | Viscosity of Reconstituted Suspension (mPa·s) |
|---|---|---|
| 750 | 107 | 128.2 |
|  | 135$^\beta$ | 130.8* |
|  | 141 | 128.2 |

Note:
The viscosity measurement in the table above were for freshly prepared reconstituted suspensions from therir respective diluents.
*Freshly prepared reconstituted suspensions from their respective diluents.
$^\beta$Diluent that was 6M, Day 0 (2-8° C.).
The concentration of sodium CMC used in the preparation of diluents is 1.2% w/v.

Inference: Viscosity results for diluent and reconstituted suspension for all the above tested formulations were found to be in the range of 100-150 mPa·s.

7.4 PXRD Studies

Figure 10:
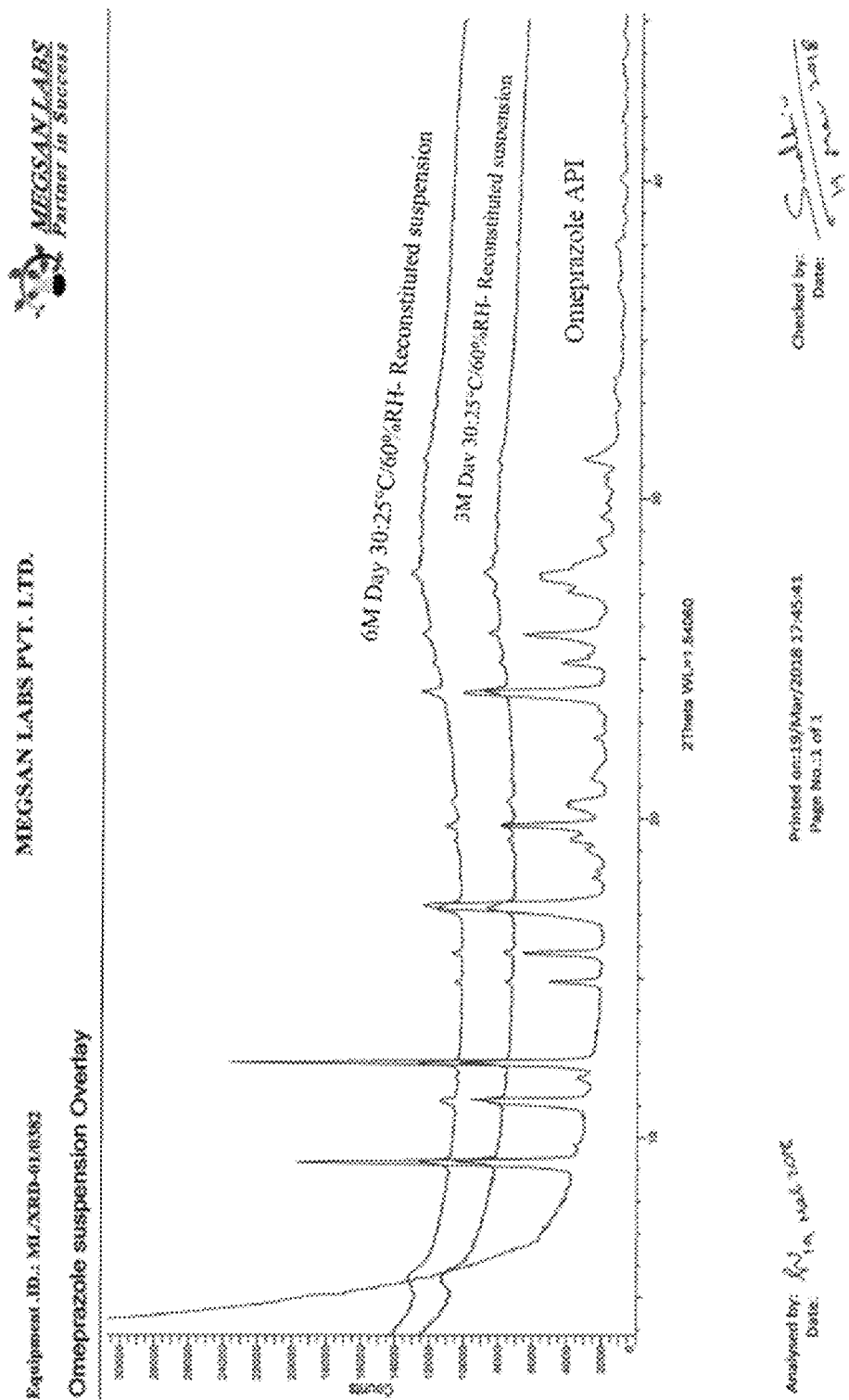
FIG. 10 includes a plot showing the powder X-ray diffraction (PXRD) patterns for sodium CMC+1% w/v poloxamer reconstituted suspensions at 3 month and 6 month time points at 25° C./60% RH.
Figure 11:
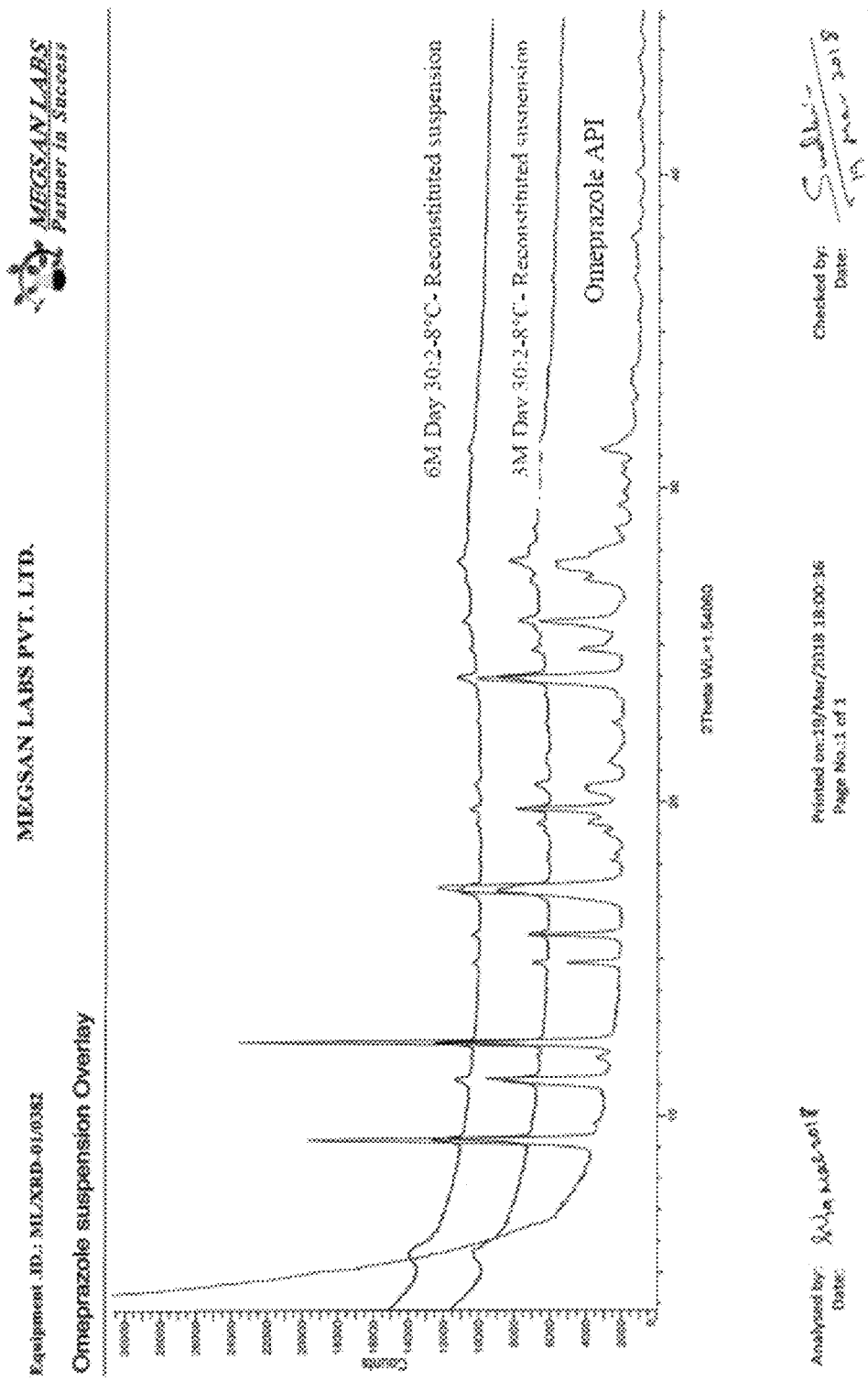
FIG. 11 includes a plot showing the powder X-ray diffraction (PXRD) patterns for sodium CMC+1% w/v poloxamer reconstituted suspensions at 3 month and 6 month time points at 2-8° C.

To evaluate the polymorphic characteristic of omeprazole API during reconstitution stability studies, the reconstituted suspensions were analyzed by X-ray diffraction (XRD) at 3M and 6M time points at 25° C./60% RH and 2-8° C. conditions.
The sample details for those are provided below and the results are shown in FIGS. 10-11.

| Sample Details |
|---|
| 3M Day 30:25° C./60% RH - Reconstituted suspension |
| 3M Day 30:2-8° C. - Reconstituted suspension |
| 6M Day 30:25° C./60% RH - Reconstituted suspension |
| 6M Day 30:2-8° C. - Reconstituted suspension |
| Omeprazole API - Reference |

Inference: Based on the PXRD data, all the characteristic peaks were observed and hence there is no polymorphic form conversion of omeprazole API through to 6M stability studies.

Example 8: Formulation Robustness Study for Lead Prototype 8.0 Formulation Robustness Study
Based on the results of the prototype stability study, freeze thaw study, and pharmacokinetic evaluation, sodium CMC with 1% w/v poloxamer 188 selected as the preferred prototype and was further evaluated. To evaluate the robustness of the sodium CMC with 1% w/v poloxamer 188 formulation additional studies were conducted with two different omeprazole API lots and two different sodium CMC lots.

8.1 Test Preparation for Stability Studies
Four tested formulations were manufactured and evaluated in stability studies. Short term stability studies (2 months) were conducted to assess the impact of sodium CMC lots and omeprazole API lots on the physico-chemical properties of the reconstituted suspension. Details on the tested formulations, along with corresponding lots, are summarized in the table below.

| Stability Test No | Sodium CMC Lot | Omeprazole API Lot |
|---|---|---|
| OME-20-S-044 | 1 | 1 |
| OME-20-S-045 | 1 | 2 |
| OME-20-S-046 | 2 | 1 |
| OME-20-S-047 | 2 | 2 |

8.2 Storage Conditions and Testing Frequency for the Stability Studies
The above mentioned 4 tested formulations were evaluated in a stability study.

| Storage conditions | Testing frequency (Months) |
|---|---|
| 25 ± 2° C. & 60 ± 5% RH | 0 & 2 |

Samples were removed at each time point and reconstitution was performed. Reconstituted suspension was analyzed at three different time points i.e., Initial, Day 15 and Day 30 (In-use stability at 2-8° C.).

Example 9: Characterization of the Four Tested Formulations of Lead Formulation 9.1 Description
For all the reconstituted suspensions, samples were physically observed at each stability time point. Data are summarized in the table below.
Specification: Pink to red hazy liquid.
A) Comparison of sodium CMC with 1% w/v poloxamer 188 reconstituted suspension at different stability time points:

| Stability Test No. (In-Use Time-point) | Description |
|---|---|
| OME-20-S-048 (Initial, D0) | Homogeneous suspension with pink color. Free flowing suspension. White colored particles observed when seen from the bottom of the glass beaker. |
| OME-20-S-049 (Initial, D0) | Homogeneous suspension with pink color. Free flowing suspension. White colored particles observed when seen from the bottom of the glass beaker. |
| OME-20-S-050 (Initial, D0) | Homogeneous suspension with pink color. Free flowing suspension. White colored particles observed when seen from the bottom of the glass beaker. |
| OME-20-S-051 (Initial, D0) | Homogeneous suspension with pink color. Free flowing suspension. White colored particles observed when seen from the bottom of the glass beaker. |
| OME-20-S-048 (Initial, D15) | Homogeneous suspension with pink color. Free flowing suspension. White colored particles observed when seen from the bottom of the glass beaker. |
| OME-20-S-049 (Initial, D15) | Homogeneous suspension with pink color. Free flowing suspension. White colored particles observed when seen from the bottom of the glass beaker. |
| OME-20-S-050 (Initial, D15) | Homogeneous suspension with pink color. Free flowing suspension. White colored particles observed when seen from the bottom of the glass beaker. |
| OME-20-S-051 (Initial, D15) | Homogeneous suspension with pink color. Free flowing suspension. White colored particles observed when seen from the bottom of the glass beaker. |
| OME-20-S-048 (Initial, D30) | Homogeneous suspension with pink color. Free flowing suspension. Large white colored particles observed when seen from the bottom of the glass beaker. |
| OME-20-S-049 (Initial, D30) | Homogeneous suspension with pink color. Free flowing suspension. Large white colored particles observed when seen from the bottom of the glass beaker. |
| OME-20-S-050 (Initial, D30) | Homogeneous suspension with pink color. Free flowing suspension. White colored particles observed when seen from the bottom of the glass beaker. |
| OME-20-S-051 (Initial, D30) | Homogeneous suspension with pink color. Free flowing suspension. White colored particles observed when seen from the bottom of the glass beaker. |
| OME-20-S-052 (2M, D0) | Homogeneous suspension with pink color. Free flowing suspension. Large white colored particles observed when seen from the bottom of the glass beaker. |
| OME-20-S-053 (2M, D0) | Homogeneous suspension with pink color. Free flowing suspension. Large white colored particles observed when seen from the bottom of the glass beaker. |
| OME-20-S-054 (2M, D0) | Homogeneous suspension with pink color. Free flowing suspension. Small white colored particles observed when seen from the bottom of the glass beaker. |
| OME-20-S-055 (2M, D0) | Homogeneous suspension with pink color. Free flowing suspension. Small white colored particles observed when seen from the bottom of the glass beaker. |
| OME-20-S-052 (2M, D15) | Homogeneous suspension with pink color. Free flowing suspension. Large white colored particles observed when seen from the bottom of the glass beaker. |

-continued

| Stability Test No. (In-Use Time-point) | Description |
|---|---|
| OME-20-S-053 (2M, D15) | Homogeneous suspension with pink color. Free flowing suspension. Large white colored particles observed when seen from the bottom of the glass beaker. |
| OME-20-S-054 (2M, D15) | Homogeneous suspension with pink color. Free flowing suspension. Small white colored particles observed when seen from the bottom of the glass beaker. |
| OME-20-S-055 (2M, D15) | Homogeneous suspension with pink color. Free flowing suspension. Small white colored particles observed when seen from the bottom of the glass beaker. |
| OME-20-S-052 (2M, D30) | Homogeneous suspension with pink color. Free flowing suspension. Large white colored particles observed when seen from the bottom of the glass beaker. |
| OME-20-S-053 (2M, D30) | Homogeneous suspension with pink color. Free flowing suspension. Large white colored particles observed when seen from the bottom of the glass beaker. |
| OME-20-S-054 (2M, D30) | Homogeneous suspension with pink color. Free flowing suspension. Small white colored particles observed when seen from the bottom of the glass beaker. |
| OME-20-S-055 (2M, D30) | Homogeneous suspension with pink color. Free flowing suspension. Small white colored particles observed when seen from the bottom of the glass beaker. |

Inference: All four tested formulations of sodium CMC+ 1.0% w/v poloxamer 188 looked similar with respect to color (pink color) at all-time points. At certain time points, small amounts of white particles were observed. However it did not show significant impact on assay and dissolution of the formulations. Overall, with regard to the description, all four tested formulations conformed to the specification for omeprazole suspension.

9.2 Assay

The assay data at different stability time points are mentioned in the table below.

Specification: NLT 90% and NMT 110% of labeled amount of omeprazole.

Figure 12:
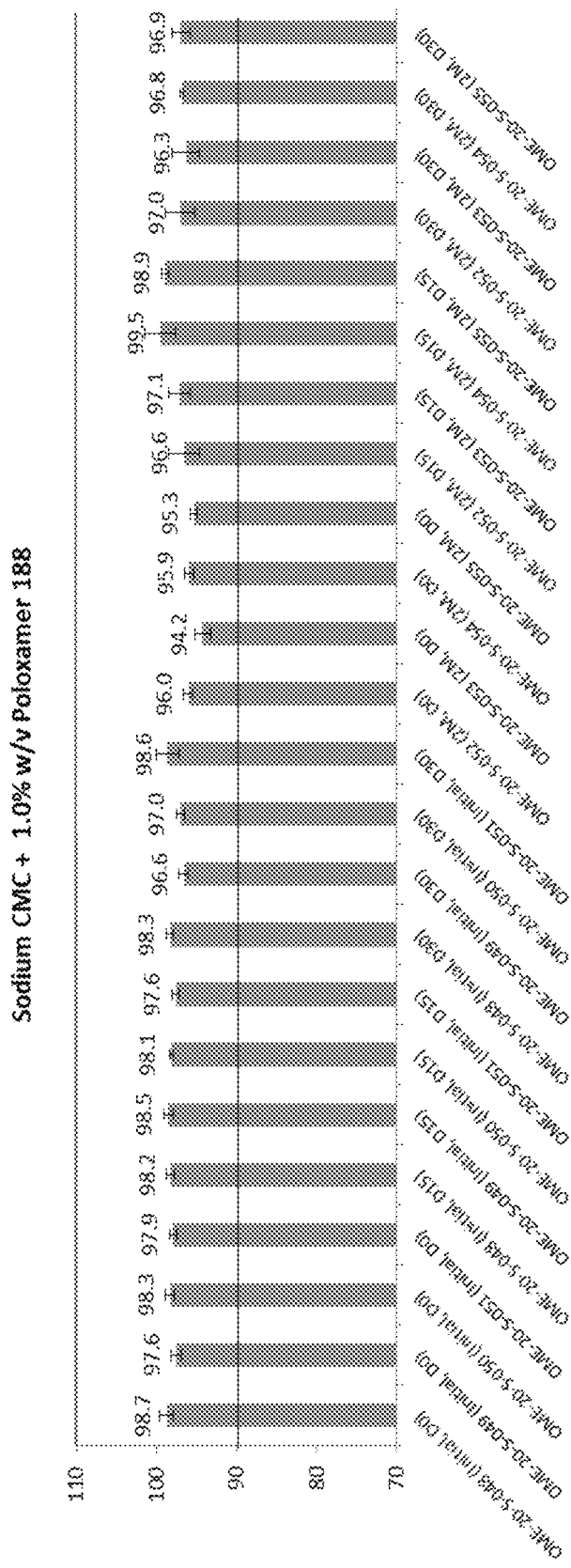
FIG. 12 includes a bar graph showing the assay comparison of the sodium CMC+1% w/v poloxamer reconstituted suspension at different stability time points.

A) Assay Comparison of sodium CMC with 1% w/v poloxamer 188 reconstituted suspension at different stability time points (FIG. 12):

| | Sodium CMC + 1.0% w/v Poloxamer 188 | | | | | | | | | | | |
|---|---|---|---|---|---|---|---|---|---|---|---|---|
| | OME-20-S-048 (Initial, D0) | OME-20-S-049 (Initial, D0) | OME-20-S-050 (Initial, D0) | OME-20-S-051 (Initial, D0) | OME-20-S-048 (Initial, D15) | OME-20-S-049 (Initial, D15) | OME-20-S-050 (Initial, D15) | OME-20-S-051 (Initial, D15) | OME-20-S-048 (Initial, D30) | OME-20-S-049 (Initial, D30) | OME-20-S-050 (Initial, D30) | OME-20-S-051 (Initial, D30) |
| Assay % | 98.7 | 97.8 | 98.3 | 97.9 | 98.2 | 98.3 | 98.1 | 97.6 | 98.3 | 96.6 | 97.0 | 98.8 |
| RSD | 0.84 | 0.64 | 0.56 | 0.46 | 0.51 | 0.56 | 0.27 | 0.47 | 0.47 | 0.57 | 0.53 | 1.44 |
| | OME-20-S-052 (2M, D0) | OME-20-S-053 (2M, D0) | OME-20-S-054 (2M, D0) | OME-20-S-055 (2M, D0) | OME-20-S-052 (2M, D15) | OME-20-S-053 (2M, D15) | OME-20-S-054 (2M, D15) | OME-20-S-055 (2M, D15) | OME-20-S-052 (2M, D30) | OME-20-S-053 (2M, D30) | OME-20-S-054 (2M, D30) | OME-20-S-055 (2M, D30) |
| Assay % | 96.0 | 94.8 | 95.9 | 95.3 | 96.6 | 97.1 | 99.5 | 98.9 | 97.0 | 96.3 | 96.8 | 96.9 |
| RSD | 0.55 | 1.02 | 0.52 | 0.44 | 1.92 | 1.40 | 1.94 | 0.40 | 1.86 | 1.67 | 0.26 | 1.17 |

Inference: The assay values of all four tested formulations were within 90-110% at all stability time-points. % RSD for assay for all four tested formulations at all stability time points was found to be less than 2%, which indicated that the suspensions were homogeneous. Overall, the assay values of all four tested formulations met the specification for the omeprazole suspension.

9.3 Dissolution

For all four tested formulations, dissolution was performed in OGD media at all stability time points.

Specification: NLT 70% (Q) of the labeled amount of omeprazole is dissolved in 30 minutes. The quantity (Q) is the amount of dissolved active ingredient specified in the individual monograph, expressed as a percentage of the labeled content of the dosage unit.

Figure 13:
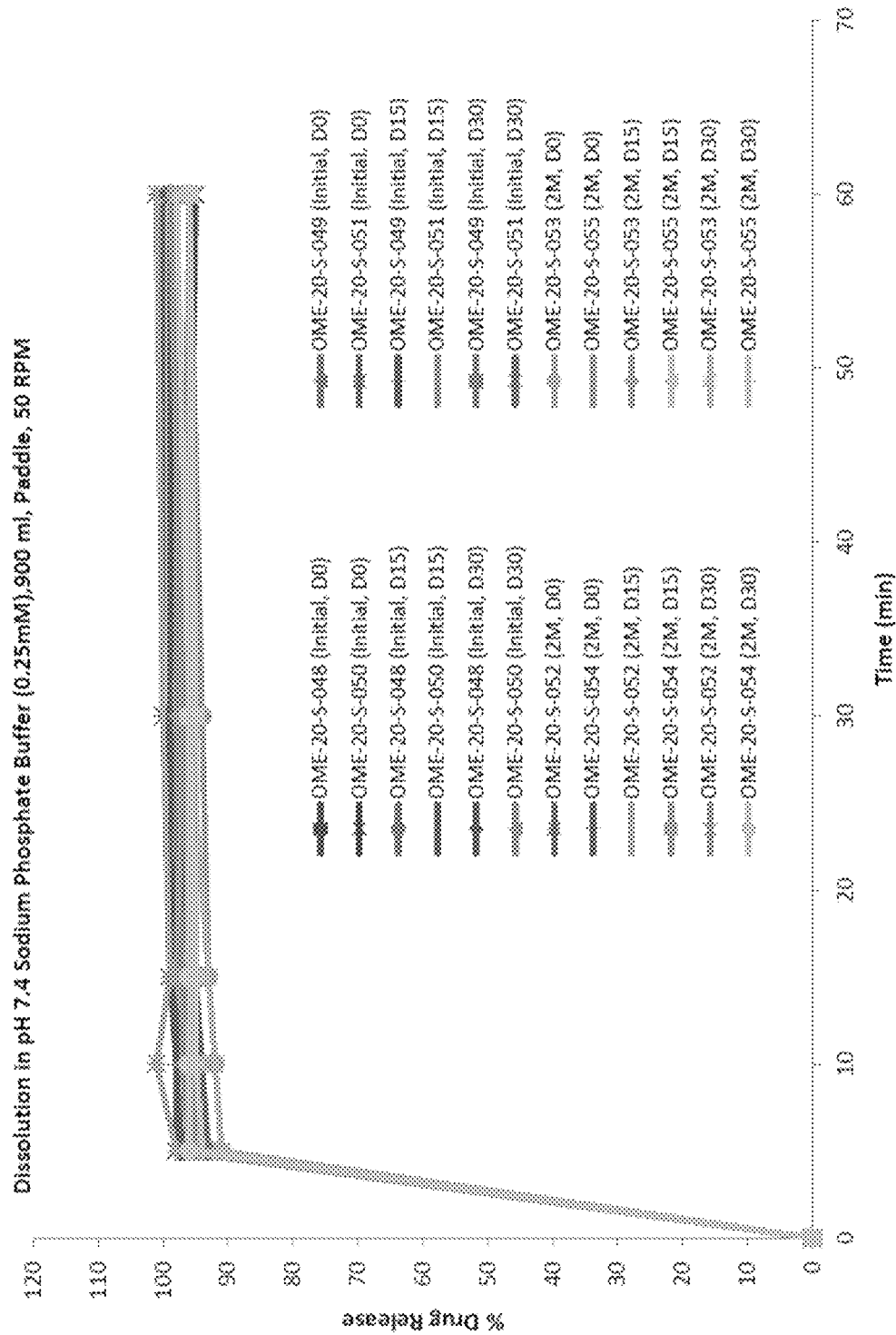
FIG. 13 includes a plot showing the dissolution profile comparison for four tested formulations of sodium CMC+1% w/v poloxamer reconstituted suspension in pH 7.4 sodium phosphate buffer media.

Dissolution Details:
USP Apparatus: II (Paddle)
Speed: 50 rpm
Media: 0.25 mM Sodium Phosphate Buffer, pH 7.4
Volume: 900 mL
Recommended Sampling Time points: 5, 10, 15, 30, 60 minutes and recovery A) Dissolution profile comparison of four tested formulations of sodium CMC with 1% w/v poloxamer 188 reconstituted suspension at different stability time points (FIG. 13):

pH 7.4 Sodium Phosphate Buffer (0.25 mM), 900 ml, Paddle, 50 RPM, Sodium CMC + 1% w/v Poloxamer % Drug release

| Time point (min) | OME-20-S-048 (Intial, D0) | % RSD | OME-20-S-049 (Intial, D0) | % RSD | OME-20-S-050 (Intial, D0) | % RSD | OME-20-S-051 (Intial, D0) | % RSD | OME-20-S-048 (Intial, D15) | % RSD | OME-20-S-049 (Intial, D15) | % RSD | OME-20-S-050 (Intial, D15) | % RSD | OME-20-S-051 (Intial, D15) | % RSD | OME-20-S-048 (Intial, D30) | % RSD | OME-20-S-049 (Intial, D30) | % RSD | OME-20-S-050 (Intial, D30) | % RSD | OME-20-S-051 (Intial, D30) | % RSD |
|---|---|---|---|---|---|---|---|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 5 | 98 | 0.6 | 96 | 0.6 | 95 | 0.6 | 93 | 0.0 | 96 | 2.7 | 97 | 1.5 | 98 | 5.6 | 95 | 0.0 | 95 | 2.6 | 94 | 1.8 | 96 | 4.7 | 94 | 1.6 |
| 10 | 97 | 0.6 | 96 | 1.0 | 95 | 0.6 | 94 | 1.1 | 96 | 2.4 | 98 | 1.5 | 98 | 5.1 | 95 | 0.6 | 96 | 3.8 | 95 | 1.3 | 97 | 4.7 | 95 | 1.6 |
| 15 | 98 | 0.6 | 97 | 0.6 | 96 | 0.6 | 95 | 1.1 | 97 | 2.4 | 98 | 0.6 | 99 | 4.5 | 96 | 0.0 | 98 | 4.2 | 95 | 1.6 | 97 | 5.5 | 95 | 1.6 |
| 30 | 98 | 0.6 | 96 | 0.6 | 96 | 0.6 | 95 | 1.1 | 99 | 1.7 | 100 | 2.9 | 99 | 4.0 | 96 | 0.0 | 98 | 4.6 | 96 | 1.8 | 98 | 5.0 | 96 | 1.6 |
| 60 | 98 | 0.6 | 96 | 1.0 | 95 | 3.7 | 96 | 1.0 | 99 | 1.5 | 100 | 1.2 | 99 | 3.5 | 96 | 0.0 | 99 | 5.6 | 96 | 1.8 | 98 | 4.7 | 96 | 2.6 |
| Recovery | 98 | 0.6 | 96 | 0.6 | 97 | 4.1 | 97 | 0.6 | 100 | 2.0 | 100 | 1.7 | 100 | 3.0 | 96 | 0.0 | 99 | 5.6 | 96 | 1.8 | 99 | 4.4 | 97 | 3.1 |

| Time point (min) | OME-20-S-052 (2M, D0) | % RSD | OME-20-S-053 (2M, D0) | % RSD | OME-20-S-054 (2M, D0) | % RSD | OME-20-S-055 (2M, D0) | % RSD | OME-20-S-052 (2M, D15) | % RSD | OME-20-S-053 (2M, D15) | % RSD | OME-20-S-054 (2M, D15) | % RSD | OME-20-S-055 (2M, D15) | % RSD | OME-20-S-052 (2M, D30) | % RSD | OME-20-S-053 (2M, D30) | % RSD | OME-20-S-054 (2M, D30) | % RSD | OME-20-S-055 (2M, D30) | % RSD |
|---|---|---|---|---|---|---|---|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 5 | 98 | 0.6 | 91 | 0.7 | 95 | 0.6 | 95 | 1.1 | 89 | 1.1 | 91 | 0.7 | 96 | 0.0 | 92 | 0.7 | 95 | 0.6 | 91 | 0.7 | 96 | 0.0 | 94 | 1.3 |
| 10 | 101 | 1.0 | 92 | 0.0 | 96 | 1.0 | 95 | 1.1 | 90 | 1.7 | 92 | 1.1 | 97 | 0.6 | 92 | 0.7 | 96 | 1.1 | 92 | 0.7 | 96 | 0.0 | 95 | 0.6 |
| 15 | 99 | 1.2 | 93 | 0.6 | 98 | 1.0 | 95 | 1.3 | 92 | 1.3 | 93 | 1.3 | 98 | 0.6 | 93 | 1.1 | 99 | 1.3 | 93 | 0.6 | 96 | 0.0 | 95 | 1.3 |
| 30 | 100 | 1.7 | 94 | 0.6 | 97 | 0.6 | 95 | 1.3 | 95 | 1.3 | 94 | 1.3 | 98 | 0.6 | 94 | 1.3 | 97 | 1.2 | 96 | 1.3 | 96 | 0.6 | 96 | 0.6 |
| 60 | 101 | 1.2 | 96 | 1.3 | 98 | 0.6 | 96 | 1.6 | 97 | 2.6 | 94 | 1.6 | 98 | 0.6 | 96 | 1.3 | 99 | 1.0 | 98 | 2.0 | 96 | 0.6 | 98 | 1.0 |
| Recovery | 100 | 1.0 | 96 | 1.0 | 98 | 0.6 | 96 | 1.0 | 98 | 2.1 | 95 | 1.8 | 99 | 0.6 | 96 | 0.6 | 100 | 1.5 | 99 | 1.7 | 96 | 0.6 | 98 | 1.0 |

Inference: The dissolution profile for all four tested formulations of sodium CMC with 1% w/v poloxamer 188 seemed to be similar. No significant difference in dissolution profile was observed throughout the stability evaluation. Overall, the dissolution Profile for all four tested formulations of sodium CMC with 1% w/v poloxamer 188 met the specification.

9.4 Related Substance

For all four tested formulations of sodium CMC with 1% w/v poloxamer 188, related substance analysis was performed at all stability time points.

Specification:
A) Omeprazole Related Compound F&G: NMT 0.50%
B) 5-Methoxy-1H-Benzimidazol-2-thiol: NMT 0.50%
C) Omeprazole sulphone N-Oxide: NMT 0.50%
D) Omeprazole N-Oxide: NMT 0.50%
E) Omeprazole Sulphone: NMT 0.50%
F) Omeprazole 4-Chloro analog (IMP-H): NMT 0.50%
G) Sulphide (Ufiprazole): NMT 0.50%
H) Desmethoxy Omeprazole: NMT 0.50%
I) Any other individual impurity: NMT 0.20%
J) Total impurities: NMT 2.0%

A) Related Substance comparison of sodium CMC with 1% w/v poloxamer 188 reconstituted suspension at different stability time points:

| | Sodium CMC + 1.0% Polaxomer | | | | | | | |
|---|---|---|---|---|---|---|---|---|
| Related Substance | OME-20-S-048 (Initial, D0) | OME-20-S-049 (Initial, D0) | OME-20-S-050 (Initial, D0) | OME-20-S-051 (Initial, D0) | OME-20-S-048 (Initial, D30) | OME-20-S-049 (Initial, D30) | OME-20-S-050 (Initial, D30) | OME-20-S-051 (Initial, D30) |
| Omeprazole F&G | 0.0079 | 0.0069 | 0.0062 | 0.0072 | 0.0551 | 0.0544 | 0.0574 | 0.0503 |
| 5-Methoxy Benzamidazole 2 thiol | 0.003 | 0.003 | 0.0038 | 0.0032 | 0.0012 | 0.0017 | 0.0018 | 0.0031 |
| Omeprazole sulphone N-Oxide | ND | ND | ND | ND | ND | ND | ND | ND |
| Omeprazole N-Oxide | 0.01 | 0.0123 | 0.0097 | 0.0174 | 0.0167 | 0.0193 | 0.0142 | 0.0186 |
| Omeprazole Sulphone (IMP-A) | 0.01 | 0.0269 | 0.0193 | 0.0419 | 0.0153 | 0.0237 | 0.018 | 0.0313 |
| Omeprazole 4-Chloro analog (IMP-H) | ND | ND | ND | ND | ND | ND | ND | ND |
| Omeprazole Sulphide | 0.0268 | 0.0194 | 0.0223 | 0.0166 | 0.0466 | 0.0552 | 0.063 | 0.0603 |
| Desmethoxy Omeprazole | ND | ND | 0.005 | 0.0064 | 0.0221 | 0.0217 | 0.023 | 0.0223 |
| unknown | 0.0116 (RRT: 0.482) | 0.011 (RRT: 0.483) | 0.0116 (RRT: 0.483) | 0.0063 (RRT: 0.484) | 0.0769 (RRT: 0.481) | 0.0831 (RRT: 0.481) | 0.0811 (RRT: 0.478) | 0.0769 (RRT: 0.482) |
| unknown | 0.0097 (RRT: 0.117) | 0.0117 (RRT: 0.116) | 0.0083 (RRT: 0.117) | 0.0062 (RRT: 0.115) | 0.0668 (RRT: 0.116) | 0.0667 (RRT: 0.115) | 0.0763 (RRT: 0.115) | 0.0703 (RRT: 0.116) |
| Total impurities | 0.1143 | 0.1367 | 0.1641 | 0.2100 | 0.3760 | 0.3981 | 0.4125 | 0.3852 |
| Related Substance | OME-20-S-052 (2M, D0) | OME-20-S-053 (2M, D0) | OME-20-S-054 (2M, D0) | OME-20-S-055 (2M, D0) | OME-20-S-052 (2M, D30) | OME-20-S-053 (2M, D30) | OME-20-S-054 (2M, D30) | OME-20-S-055 (2M, D30) |
| Omeprazole F&G | 0.0371 | 0.0375 | 0.0338 | 0.0335 | 0.0769 | 0.0731 | 0.0697 | 0.0634 |
| 5-Methoxy Benzamidazole 2 thiol | 0.0041 | 0.004 | 0.0045 | 0.0042 | ND | 0.0027 | 0.0023 | 0.0033 |
| Omeprazole sulphone N-Oxide | ND | ND | ND | ND | ND | ND | ND | ND |
| Omeprazole N-Oxide | 0.0118 | 0.0209 | 0.0135 | 0.0186 | 0.0174 | 0.0161 | 0.0105 | 0.0161 |
| Omeprazole Sulphone (IMP-A) | 0.0409 | 0.0637 | 0.0483 | 0.0722 | 0.0244 | 0.0113 | 0.029 | 0.03 |
| Omeprazole 4-Chloro analog (IMP-H) | ND | ND | ND | ND | ND | ND | ND | ND |
| Omeprazole Sulphide | 0.0525 | 0.0374 | 0.0448 | 0.0417 | 0.0419 | 0.082 | 0.045 | 0.0085 |
| Desmethoxy Omeprazole | 0.0063 | 0.008 | 0.0074 | 0.0077 | 0.0194 | 0.0232 | 0.0191 | 0.0167 |

-continued

| | Sodium CMC + 1.0% Polaxomer | | | | | | | |
|---|---|---|---|---|---|---|---|---|
| unknown | 0.0511 (RRT: 0.479) | 0.0419 (RRT: 0.480) | 0.0347 (RRT: 0.479) | 0.0245 (RRT: 0.479) | 0.0674 (RRT: 0.483) | 0.1045 (RRT: 0.482) | 0.0557 (RRT: 0.482) | 0.0942 (RRT: 0.481) |
| unknown | 0.0706 (RRT: 0.118) | 0.0683 (RRT: 0.118) | 0.0761 (RRT: 0.117) | 0.0741 (RRT: 0.117) | 0.0876 (RRT: 0.117) | 0.0936 (RRT: 0.117) | 0.0868 (RRT: 0.116) | 0.0832 (RRT: 0.166) |
| Total impurities | 0.3467 | 0.3434 | 0.3279 | 0.3302 | 0.3873 | 0.4821 | 0.3731 | 0.3815 |

Inference: Four impurities (Omeprazole F&G, Omeprazole Sulphide and Unknown impurities at RRT: 0.117 and RRT: 0.480) showed an increase in trend in stability and these impurities can be considered as degradants. However, individual known and unknown impurity levels were <0.2% in both the formulations. Overall, all four tested formulations were acceptable with respect to related substance content.

SUMMARY

Based on the stability data for all four tested formulations of the robustness study through 2M 25° C./60% RH it was concluded that the formulations are robust with respect to different omeprazole API lots and different sodium CMC lots.

The sodium CMC with 1% w/v poloxamer-finalized prototype formula is as follows:

| Ingredient | Function | % w/v |
|---|---|---|
| Poloxamer 188 (Kolliphor P188) | Surfactant | 1 |
| Sodium CMC (Cekol 700P) | Viscosity building/suspending agent | 1.2 |
| Sodium bicarbonate | Acid neutralizing agent | 8.4 |
| Simethicone emulsion | Defoamer | 0.15 |
| Strawberry Flavor CW08 | Flavoring agent | 0.15 |
| 70% sorbitol solution | Sweetener | 2.5 |
| Sodium citrate | Palatability enhancer/buffer | 1 |
| Sucralose | Sweetener | 0.4 |
| FD&C Red No. 40 | Coloring agent | 0.003 |
| Benzyl alcohol | Preservative | 0.5 |
| Water | Solvent | q.s. |

Further Embodiments

Additional, non-limiting embodiments of this disclosure are as follows:

A1. A liquid diluent for the reconstitution of a proton pump inhibitor, comprising about 0.5%-4% w/v poloxamer (e.g., poloxamer 188) and about 1.0%-2.5% w/v sodium CMC, wherein the liquid diluent is stable for at least 30 days.

A2. The liquid diluent of claim A1, wherein the liquid diluent comprises:
  about 8.0%-8.8% w/v acid neutralizing agent;
  about 0.5%-1.5% w/v buffer;
  about 0.1%-0.3% w/v defoamer;
  about 0.35%-3.5% w/v sweetener;
  about 0.4%-0.6% w/v preservative; and
  water.

A3. A liquid diluent for the reconstitution of a proton pump inhibitor, consisting essentially of:
  about 0.5%-4% w/v poloxamer (e.g., poloxamer 188);
  about 1.0%-2.5% w/v sodium CMC;
  about 8.0%-8.8% w/v acid neutralizing agent;
  about 0.5%-1.5% w/v buffer;
  about 0.1%-0.3% w/v defoamer;
  about 0.35%-3.5% w/v sweetener;
  about 0.4%-0.6% w/v preservative; and
  water,
wherein the liquid diluent is stable for at least 30 days.

A4. A liquid diluent for the reconstitution of a proton pump inhibitor, consisting of:
  about 0.5%-4% w/v poloxamer (e.g., poloxamer 188);
  about 1.0%-2.5% w/v sodium CMC;
  about 8.0%-8.8% w/v acid neutralizing agent;
  about 0.5%-1.5% w/v buffer;
  about 0.1%-0.3% w/v defoamer;
  about 0.35%-3.5% w/v sweetener;
  about 0.4%-0.6% w/v preservative;
  flavoring agent;
  coloring agent; and
  water,
wherein the liquid diluent is stable for at least 30 days.

A5. The liquid diluent of any one of claims A2-A4, wherein the acid neutralizing agent is sodium bicarbonate.

A6. The liquid diluent of any one of claims A2-A5, wherein the buffer is sodium citrate.

A7. The liquid diluent of any one of claims A2-A6, wherein the defoamer is simethicone emulsion.

A8. The liquid diluent of any one of claims A2-A7, wherein the sweetener is sorbitol solution and/or sucralose.

A9. The liquid diluent of claim A8, wherein the sweetener is about 2.0%-3.0% w/v sorbitol solution.

A10. The liquid diluent of claim A8 or A9, wherein the sweetener is about 0.35%-0.5% w/v sucralose.

A11. The liquid diluent of any one of claims A2-A10, wherein the preservative is benzyl alcohol.

A12. The liquid diluent of any one of the preceding claims, wherein the poloxamer is about 0.5% w/v.

A13. The liquid diluent of any one of claims A1-A11, wherein the poloxamer is about 1% w/v.

A14. The liquid diluent of any one of claims A1-A11, wherein the poloxamer is about 2% w/v.

A15. The liquid diluent of any one of claims A1-A11, wherein the poloxamer is about 4% w/v.

A16. The liquid diluent of any one of the preceding claims, wherein the sodium CMC is about 1.2% w/v.

A17. The liquid diluent of any one of claims A1-A15, wherein the sodium CMC is about 2% w/v.

A18. The liquid diluent of any one of the preceding claims, wherein the diluent includes about 0.002%-0.005% w/v FD&C Red No. 40.

A19. The liquid diluent of claim A18, wherein the FD&C Red No. 40 is about 0.003% w/v.

A20. The liquid diluent of any one of the preceding claims, wherein the diluent includes about 0.1%-0.2% w/v Strawberry Flavor CW08.

A21. The liquid diluent of claim A20, wherein the Strawberry Flavor CW08 is about 0.15% w/v.

A22. The liquid diluent of any one of claims A2-A21, wherein the acid neutralizing agent is sodium bicarbonate, and/or wherein the acid neutralizing agent is about 8.4% w/v.

A23. The liquid diluent of any one of claims A2-A22, wherein the buffer is sodium citrate, and/or wherein the buffer agent is about 1% w/v.

A24. The liquid diluent of any one of claims A2-A23, wherein the defoamer is simethicone emulsion, and/or wherein the defoamer agent is about 0.15% w/v.

A25. The liquid diluent of any one of claims A2-A24, wherein the sweetener is about 2.5% w/v sorbitol solution and/or about 0.4% w/v sucralose.

A26. The liquid diluent of any one of claims A2-A25, wherein the preservative is benzyl alcohol, and/or wherein the preservative is about 0.5% w/v.

A27. The liquid diluent of any one of claims A4-A26, wherein the flavoring agent is Strawberry Flavor CW08, and/or wherein the flavoring agent is about 0.15% w/v.

A28. The liquid diluent of any one of claims A4-A27, wherein the coloring agent is FD&C Red No. 40, and/or wherein the coloring agent is about 0.003% w/v.

A29. The liquid diluent of any one of the preceding claims, wherein the proton pump inhibitor is omeprazole.

B1. A suspension of omeprazole comprising:
omeprazole, a surfactant, a suspending agent, an acid neutralizing agent (optionally, sodium bicarbonate), a buffer (optionally sodium citrate), a defoamer (optionally simethicone emulsion), a preservative (optionally benzyl alcohol), a sweetener, and water;
wherein the suspension is homogenous and stable for at least 30 days at ambient conditions and at refrigerated temperature conditions.

B2. A suspension of omeprazole consisting essentially of:
omeprazole, a surfactant, a suspending agent, an acid neutralizing agent (optionally, sodium bicarbonate), a buffer (optionally sodium citrate), a defoamer (optionally simethicone emulsion), a preservative (optionally benzyl alcohol), a sweetener, and water;
wherein the suspension is homogenous and stable for at least 30 days at ambient conditions and at refrigerated temperature conditions.

B3. The suspension of claim B1 or B2, wherein the surfactant is poloxamer (e.g., poloxamer 188).

B4. The suspension of claim B3, wherein the poloxamer is about 0.5%-4.0% w/v.

B5. The suspension of claim B3, wherein the poloxamer is about 1% w/v.

B6. The suspension of any one of claims B1-B5, wherein the suspending agent is sodium CMC.

B7. The suspension of claim B6, wherein the sodium CMC is about 1.0%-2.5% w/v.

B8. The suspension of claim B6, wherein the sodium CMC is about 1.2% w/v.

B9. The suspension of any one of claims B1 and B3-B8, wherein the suspension does not comprise propylene glycol.

B10. The suspension of any one of claims B1 and B3-B9, wherein the suspension does not comprise glycerin.

C1. A suspension of omeprazole comprising:
omeprazole API, a surfactant, a suspending agent, an acid neutralizing agent (optionally, sodium bicarbonate), a buffer (optionally sodium citrate), a defoamer (optionally simethicone emulsion), a preservative (optionally benzyl alcohol), a sweetener, and water;
wherein the surfactant is poloxamer (e.g., poloxamer 188) and the suspending agent is sodium CMC;
wherein the suspension is homogenous and stable for at least 30 days at ambient and refrigerated temperature conditions; and
wherein the suspension has a concentration of omeprazole API detected by assay; and
wherein the concentration of omeprazole API is greater than 90% for up to 30 days at ambient and refrigerated temperature conditions.

C2. A suspension of omeprazole consisting essentially of:
omeprazole API, a surfactant, a suspending agent, an acid neutralizing agent (optionally, sodium bicarbonate), a buffer (optionally sodium citrate), a defoamer (optionally simethicone emulsion), a preservative (optionally benzyl alcohol), a sweetener, and water;
wherein the surfactant is poloxamer (e.g., poloxamer 188) and the suspending agent is sodium CMC;
wherein the suspension is homogenous and stable for at least 30 days at ambient and refrigerated temperature conditions; and
wherein the suspension has a concentration of omeprazole API detected by assay; and wherein the concentration of omeprazole API is greater than 90% for up to 30 days at ambient and refrigerated temperature conditions.

C3. The suspension of claim C1 or C2, wherein the poloxamer is about 1.0% w/v.

C4. The suspension of any one of claims C1-C3, wherein the sodium CMC is about 1.2% w/v.

D1. A suspension of omeprazole comprising:
omeprazole API, a surfactant, a suspending agent, an acid neutralizing agent (optionally, sodium bicarbonate), a buffer (optionally sodium citrate), a defoamer (optionally simethicone emulsion), a preservative (optionally benzyl alcohol), a sweetener, and water;
wherein the surfactant is poloxamer (e.g., poloxamer 188) and the suspending agent is sodium CMC;
wherein the suspension is homogenous and stable for at least 30 days at ambient and refrigerated temperature conditions; and
wherein the suspension has a % RSD for detection of omeprazole API by assay, and wherein % RSD is less than 2% for up to 30 days at ambient and refrigerated temperature conditions.

D1. A suspension of omeprazole consisting essentially of:
omeprazole API, a surfactant, a suspending agent, an acid neutralizing agent (optionally, sodium bicarbonate), a buffer (optionally sodium citrate), a defoamer (optionally simethicone emulsion), a preservative (optionally benzyl alcohol), a sweetener, and water;
wherein the surfactant is poloxamer (e.g., poloxamer 188) and the suspending agent is sodium CMC;
wherein the suspension is homogenous and stable for at least 30 days at ambient and refrigerated temperature conditions; and
wherein the suspension has a % RSD for detection of omeprazole API by assay, and wherein % RSD is less than 2% for up to 30 days at ambient and refrigerated temperature conditions.

D3. The suspension of claim D1 or D2, wherein the poloxamer (e.g., poloxamer 188) is about 1.0% w/v.

D4. The suspension of any one of claims D1-D3, wherein the sodium CMC is about 1.2% w/v.

E1. A freeze-thaw stable diluent for the reconstitution of omeprazole, comprising:
a surfactant, a suspending agent, an acid neutralizing agent (optionally, sodium bicarbonate), a buffer (optionally sodium citrate), a defoamer (optionally simethicone emulsion), a preservative (optionally benzyl alcohol), a sweetener, and water;

wherein the surfactant is poloxamer (e.g., poloxamer 188) and the suspending agent is sodium CMC or Avicel CL-611;

wherein the freeze-thaw stable diluent is resistant to gel formation following at least one freeze-thaw cycle.

E2. A freeze-thaw stable diluent for the reconstitution of omeprazole, consisting essentially of:

a surfactant, a suspending agent, an acid neutralizing agent (optionally, sodium bicarbonate), a buffer (optionally sodium citrate), a defoamer (optionally simethicone emulsion), a preservative (optionally benzyl alcohol), a sweetener, and water;

wherein the surfactant is poloxamer (e.g., poloxamer 188) and the suspending agent is sodium CMC or Avicel CL-611;

wherein the freeze-thaw stable diluent is resistant to gel formation following at least one freeze-thaw cycle.

E3. The freeze-thaw stable diluent of claim E1 or E2, wherein the sodium CMC is about 1.2% w/v.

E4. The freeze-thaw stable diluent of any one of claims E1-E3, wherein the poloxamer is about 1.0% w/v.

E5. The freeze-thaw stable diluent of any one of claims E1-E4, further comprising:
about 8.4% w/v sodium bicarbonate;
about 1.0% w/v sodium citrate;
about 0.15% w/v simethicone emulsion;
about 0.15% w/v Strawberry Flavor CW08;
about 2.5% w/v sorbitol solution;
about 0.4% w/v sucralose;
about 0.003% w/v FD&C Red No. 40;
about 0.5% w/v benzyl alcohol; and
water.

E6. The freeze-thaw stable diluent of claim E1, wherein the suspending agent is Avicel CL-611.

E7. The freeze-thaw stable diluent of claim E1, wherein the freeze-thaw stable diluent does not comprise glycerin or xanthan gum.

F1. A kit comprising:

a first container comprising a non-sterile omeprazole powder (e.g., 100% w/w);

a second container comprising a liquid diluent comprising a surfactant, a suspending agent, an acid neutralizing agent (optionally, sodium bicarbonate), a buffer (optionally sodium citrate), a defoamer (optionally simethicone emulsion), a preservative (optionally benzyl alcohol), a sweetener, and water;

wherein the surfactant is poloxamer (e.g., poloxamer 188) and the suspending agent is sodium CMC;

wherein the first and second containers are of a size such that the omeprazole powder and liquid diluent can be combined in either the first or second container to produce a reconstituted omeprazole suspension;

wherein the reconstituted omeprazole suspension is homogenous and stable for at least 30 days at ambient and refrigerated temperature conditions.

F2. The kit of claim F1, wherein the percent of omeprazole powder dissolved to make the reconstituted omeprazole suspension is >80% by dissolution assay after 5 minutes of mixing.

F3. The kit of claim F1, wherein the percent of omeprazole powder dissolved to make the reconstituted omeprazole suspension is >85% by dissolution assay after 5 minutes of mixing.

F4. The kit of claim F1, wherein the poloxamer is about 1% w/v.

F5. The kit of claim F1, wherein the sodium CMC is about 1.2% w/v.

F6. The kit of claim F1, wherein the liquid diluent comprises about 1% w/v poloxamer, about 1.2% w/v sodium CMC; about 8.4% w/v sodium bicarbonate; about 1.0% w/v sodium citrate; and about 0.15% w/v simethicone emulsion.

F7. The kit of claim F1, wherein the sweetener comprises about 2.5% w/v sorbitol solution and about 0.4% w/v sucralose.

F8. The kit of claim F1, wherein the preservative is about 0.5% w/v benzyl alcohol.

F9. The kit of claim F1, wherein the diluent further comprises about 0.15% w/v Strawberry Flavor CW08.

F10. The kit of claim F1, wherein the diluent further comprises about 0.003% w/v FD&C Red No. 40.

F11. A kit consisting essentially of:

a first container consisting of a non-sterile about 100% w/w omeprazole powder;

a second container consisting of the liquid diluent of any one of claims A1-A29;

wherein the first and second containers are of a size such that the omeprazole powder and liquid diluent can be combined in either the first or second container to produce a reconstituted omeprazole suspension;

wherein the reconstituted omeprazole suspension is homogenous and stable for at least 30 days at ambient and refrigerated temperature conditions.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A liquid diluent for reconstituting proton pump inhibitor (PPI), consisting essentially of:
   1.0%-4.0% w/v poloxamer;
   1.0%-5.0% w/v of a suspending agent, wherein the suspending agent is (i) sodium carboxymethylcellulose (CMC) or (ii) a combination of sodium CMC and microcrystalline cellulose;
   8.0%-8.8% w/v of an acid neutralizing agent;
   0.1%-0.3% w/v of a defoamer;
   0.2%-1.2% w/v of a preservative;
   water;
   optionally a buffer that maintains a pH of 8 to 9.5; and
   optionally one or more selected from a sweetener, a coloring agent, and a flavoring agent; and
   wherein the liquid diluent is stable for at least 30 days at 5±3° C. and is resistant to gel formation for at least one freeze-thaw cycle.

2. The liquid diluent of claim 1, wherein the poloxamer has a number average molecular weight of about 7000 to about 10,000 Da.

3. The liquid diluent of claim 1, wherein the poloxamer has an ethylene glycol content of about 80 wt % to about 85 wt %.

4. The liquid diluent of claim 1, wherein the poloxamer is poloxamer 188 and is present in the liquid diluent at 1% w/v, 2% w/v, or 4% w/v.

5. The liquid diluent of claim 1, wherein the suspending agent is sodium CMC and wherein the sodium CMC is present in the liquid diluent at 1.0% to 2.0% w/v.

6. The liquid diluent of claim 1, wherein the suspending agent is a combination of sodium CMC and microcrystalline cellulose.

7. The liquid diluent of claim 6, wherein the combination of sodium CMC and microcrystalline cellulose is present in the liquid diluent at about 4.0% w/v.

8. The liquid diluent of claim 1, wherein the liquid diluent comprises a coloring agent and a flavoring agent.

9. The liquid diluent of claim 1, wherein the acid neutralizing agent is sodium bicarbonate.

10. The liquid diluent of claim 1, wherein the buffer is present in the liquid diluent.

11. The liquid diluent of claim 10, wherein the buffer is selected from sodium citrate, sodium bicarbonate, or a combination thereof.

12. The liquid diluent of claim 10, wherein the buffer is one or more of a citrate, tartrate, acetate, carbonate, phosphate, metaphosphate, glycerophosphate, polyphosphate, and pyrophosphate.

13. The liquid diluent of claim 1, wherein the defoamer is simethicone emulsion.

14. The liquid diluent of claim 1, wherein the sweetener is present in the liquid diluent.

15. The liquid diluent of claim 14, wherein the sweetener is glucose, fructose, sucrose, xylitol, maltodextrin, polydextrose, glycerin, inulin, maltol, salts of acesulfame, alitame, aspartame, neotame, cyclamate salts, sucralose, sorbitol, saccharin and its salts, or a combination thereof.

16. The liquid diluent of claim 1, wherein the preservative is benzyl alcohol and is present at about 0.4% to about 0.6% w/v in the liquid diluent.

17. The liquid diluent of claim 1, wherein the preservative is one or more of the group consisting of: benzyl alcohol, ascorbic acid, ascorbyl palmitate or other pharmaceutically acceptable ascorbate salts, BHA, BHT, citric acid or other citrate salts, sodium benzoate, benzoic acid or other pharmaceutically acceptable benzoate salts, sodium bisulfate, sodium metabisulfite, sodium sulfite, parabens, potassium sorbate or other pharmaceutically acceptable sorbate salts, and vanillin.

18. The liquid diluent of claim 1, wherein the PPI is omeprazole.

19. The liquid diluent of claim 1, wherein the PPI is lansoprazole.

* * * * *